(12) United States Patent  
Almendinger et al.

(10) Patent No.: US 9,393,420 B2
(45) Date of Patent: Jul. 19, 2016

(54) SAFETY FEATURES FOR USE IN MEDICAL DEVICES

(71) Applicant: EnteroMedics, Inc., St. Paul, MN (US)

(72) Inventors: Al Almendinger, Bloomington, MN (US); Gregory Pat Spar, Big Lake, MN (US); Koen Jacob Weijand, Alicante (ES); Randy Maas, Chaska, MN (US); Steve Ellsworth, St. Paul, MN (US)

(73) Assignee: EnteroMedics Inc., St. Paul, MN (US)

( * ) Notice: Subject to any disclaimer, the term of this patent is extended or adjusted under 35 U.S.C. 154(b) by 0 days.

(21) Appl. No.: 13/793,715

(22) Filed: Mar. 11, 2013

(65) Prior Publication Data

US 2013/0238048 A1  Sep. 12, 2013

Related U.S. Application Data

(60) Provisional application No. 61/608,949, filed on Mar. 9, 2012.

(51) Int. Cl.
*A61N 1/378* (2006.01)
*A61N 1/36* (2006.01)
*H02J 7/00* (2006.01)
*A61N 1/05* (2006.01)

(52) U.S. Cl.
CPC .......... *A61N 1/36142* (2013.01); *A61N 1/3787* (2013.01); *H02J 7/007* (2013.01); *H02J 7/0091* (2013.01); *A61N 1/0509* (2013.01); *A61N 1/3605* (2013.01); *A61N 1/36053* (2013.01); *A61N 1/36125* (2013.01)

(58) Field of Classification Search
CPC ....... A61N 1/3787; A61N 1/08; A61N 1/378; H02J 7/007
See application file for complete search history.

(56) References Cited

U.S. PATENT DOCUMENTS

| 3,727,616 A | 4/1973 | Lenzkes |
| 4,308,466 A | 12/1981 | Cushman et al. |
| 4,498,478 A | 2/1985 | Bourgeois |
| 4,592,359 A | 6/1986 | Galbraith |
| 4,612,934 A | 9/1986 | Borkan |

(Continued)

FOREIGN PATENT DOCUMENTS

| CN | 102149345 A | 8/2011 |
| CN | 203458691 U | 3/2014 |

(Continued)

OTHER PUBLICATIONS

International Search Report for related PCT application PCT/US2013/030188 mailed Aug. 28, 2013.

(Continued)

*Primary Examiner* — Michael Kahelin
(74) *Attorney, Agent, or Firm* — Merchant & Gould P.C.

(57) ABSTRACT

A therapy system for applying an electrical signal to an internal anatomical feature of a patient includes an implantable component and an external component. The medical device can be checked for safety issues by periodically initiating a sequence of tests of an H-bridge circuit, and, during each test, monitoring a current flow through a sensing resistor electrically connected between a sensing connection of the H-bridge circuit and a ground. Current flow through the sensing resistor indicates that both series electrical switches within at least one of the two pairs of series electrical switches are active during that test.

5 Claims, 22 Drawing Sheets

(56) References Cited

U.S. PATENT DOCUMENTS

| | | | |
|---|---|---|---|
| 4,793,353 | A | 12/1988 | Borkan |
| 4,979,511 | A | 12/1990 | Terry, Jr. |
| 5,215,089 | A | 6/1993 | Baker, Jr. |
| 5,251,634 | A | 10/1993 | Weinberg |
| 5,263,480 | A | 11/1993 | Wernicke et al. |
| 5,279,292 | A | 1/1994 | Baumann et al. |
| 5,531,778 | A | 7/1996 | Maschine et al. |
| 5,702,431 | A | 12/1997 | Wang et al. |
| 5,733,313 | A | 3/1998 | Barreras, Sr. et al. |
| 5,755,747 | A | 5/1998 | Daly et al. |
| 6,175,765 | B1 | 1/2001 | Sullivan et al. |
| 6,185,458 | B1 | 2/2001 | Ochs et al. |
| 6,516,227 | B1 | 2/2003 | Meadows et al. |
| 6,600,956 | B2 | 7/2003 | Maschine et al. |
| 6,895,280 | B2 | 5/2005 | Meadows et al. |
| 7,089,057 | B2 | 8/2006 | Heathershaw et al. |
| 7,225,032 | B2 | 5/2007 | Schmeling et al. |
| 7,295,872 | B2 | 11/2007 | Kelly et al. |
| 7,317,948 | B1 | 1/2008 | King et al. |
| 7,386,342 | B1 | 6/2008 | Falkenberg et al. |
| 7,426,445 | B1 | 9/2008 | Fister |
| 7,711,426 | B2 * | 5/2010 | Armstrong et al. ............ 607/29 |
| 7,734,353 | B2 | 6/2010 | Gerber et al. |
| 8,040,110 | B2 | 10/2011 | Al-Anbuky et al. |
| 8,080,976 | B2 | 12/2011 | Manor et al. |
| 8,120,311 | B2 | 2/2012 | Baarman et al. |
| 8,125,190 | B2 | 2/2012 | Odaohhara |
| 8,190,258 | B2 | 5/2012 | Armstrong |
| 8,203,314 | B2 | 6/2012 | Odaohhara |
| 8,214,042 | B2 | 7/2012 | Ozawa et al. |
| 8,239,027 | B2 | 8/2012 | Imran |
| 8,260,426 | B2 | 9/2012 | Armstrong et al. |
| 8,706,256 | B2 | 4/2014 | Joshi |
| 9,168,083 | B2 | 10/2015 | Schall et al. |
| 2005/0107841 | A1 | 5/2005 | Meadows et al. |
| 2009/0005770 | A1 * | 1/2009 | Gerber et al. .................. 606/27 |
| 2009/0187230 | A1 | 7/2009 | Dilorenzo |
| 2010/0010582 | A1 | 1/2010 | Carbunaru et al. |
| 2010/0241183 | A1 | 9/2010 | DiLorenzo |
| 2010/0324618 | A1 | 12/2010 | Wanasek |
| 2012/0022608 | A1 | 1/2012 | Libbus et al. |
| 2012/0022617 | A1 | 1/2012 | Tockman et al. |
| 2012/0025786 | A1 | 2/2012 | Heizer et al. |
| 2012/0043934 | A1 | 2/2012 | Klein |
| 2012/0053653 | A1 | 3/2012 | Hiernaux et al. |
| 2012/0059431 | A1 | 3/2012 | Williams et al. |
| 2012/0065698 | A1 | 3/2012 | Errico et al. |
| 2012/0071946 | A1 | 3/2012 | Errico et al. |
| 2012/0078319 | A1 | 3/2012 | De Ridder |
| 2012/0083855 | A1 | 4/2012 | Gross et al. |
| 2012/0098481 | A1 | 4/2012 | Hunter et al. |
| 2012/0101874 | A1 | 4/2012 | Ben-Haim et al. |
| 2012/0109100 | A1 | 5/2012 | Estes et al. |
| 2012/0133324 | A1 | 5/2012 | Baarman et al. |
| 2012/0136408 | A1 | 5/2012 | Grill et al. |
| 2012/0139482 | A1 | 6/2012 | Zhang et al. |
| 2012/0172792 | A1 | 7/2012 | Baynham et al. |
| 2012/0191152 | A1 * | 7/2012 | Kameli ............................ 607/7 |
| 2012/0197342 | A1 | 8/2012 | Towe |
| 2012/0232610 | A1 | 9/2012 | Soffer et al. |
| 2012/0239108 | A1 | 9/2012 | Foutz et al. |
| 2012/0253378 | A1 | 10/2012 | Makower et al. |
| 2012/0259380 | A1 | 10/2012 | Pyles |
| 2013/0023943 | A1 | 1/2013 | Parramon et al. |
| 2013/0193914 | A1 * | 8/2013 | Gaddam et al. ............... 320/108 |
| 2014/0214132 | A1 | 7/2014 | Joshi |
| 2014/0277287 | A1 | 9/2014 | Carbunaru et al. |

FOREIGN PATENT DOCUMENTS

| | | | |
|---|---|---|---|
| WO | 9839059 | A1 | 9/1998 |
| WO | 2005067792 | A1 | 7/2005 |
| WO | 2012044472 | A2 | 4/2012 |
| WO | 2012060874 | A2 | 5/2012 |

OTHER PUBLICATIONS

International Search Report and Written Opinion for related PCT application PCT/US2013/030188 mailed Jan. 31, 2014.

Brancatisano, et al., "Implantation Technique of a Novel Vagal Blockade Medical Device for the Treatment of Obesity," IFSO-APC OSSANZ Conference 2008: Mar. 25-27, 2009, Hilton Cairns, Queensland Conference Program Handbook.

Brancastisano, et al., "Empower: A 12-Month Randomized, Prospective Clinical Trial: Safety and Effectiveness of VBLOC Therapy," 23rd Annual Scientific Conference of the Obesity Surgery Society of Australia and New Zealand, OSSANZ Conference 2010: The Changing Shape of Bariatrics, Nov. 10-12, Wednesday Nov. 10 10:30 am-12 noon, Tasmania Hotel Grand Chancellor, Hobart, Conference Program Handbook. (2010).

Camilleri, et al., "Vagal Blocking for Obesity control (VBLOC): Plasma Pancreatic Polypeptide (PPP) Response to a Standardized Sham Meal Challenge," The Obesity Society 2007 Annual Scientific Meeting, Oct. 20-24, 2007, New Orleans Louisiana. Supplement to Obesity, vol. 15, Program Abstract Supplement, (Sep. 2007).

Camilleri, et al., "Intra-abdominal Vagal Blocking (VBLOC therapy): Clinical Results with a New Implantable Medical Device," Surgery, vol. 143, No. 6, pp. 723-731, (Jun. 2008).

Camilleri, et al., "Selection of Electrical Algorithms to Treat Obesity with Intermittent Vagal Block Using an Implantable Medical Device," Surgery for Obesity and Related Diseases, Official Journal of the American Society for Bariatric Surgery, vol. 5, No. 2, pp. 224-229, (Mar./Apr. 2009).

Collins, et al., "Reduces Calorie Intake and Weight Loss during Vagal Block (VBLOC Therapy) in Morbidly Obese Patients with Type 2 Diabete Mellitus," 23rd Annual Scientific Conference of the Obesity Surgery Society of Australia and New Zealand, OSSANZ Conference 2010: The Changing Shape of Bariatrics, Nov. 10-12, Thursday Nov. 11, 10:30 am-12 noon, Tasmania Hotel Grand Chancellor, Hobart, Conference Program Handbook.

Hao, "A Programmable Implantable Neural Stimulation System," Space Medicine & Medical Engineering 21 (2):147-151 (Apr. 2008).

Herrera, et al., "Intermittent Vagal Blocking with an Implantable Device Reduces Maximum Tolerated Volume (MTV) During a Standardized Nutrient Drink Test in Obese Subjects," AGA Institute, AASLD, SSAT, The 110th Annual Meeting of the AGA Institute: Digestive Disease Week May 30-Jun. 4, 2009, Chicago, IL, Gastroenterology vol. 136, No. 5, Suppl. 1 (May 2009).

Herrera, et al., "Intermittent Vagal Blockade with an Implantable Device Improves Glycemic Control in Obese subjects with Type 2 Diabetes," 2009 Poster Session / Supplement to Surgery for Obesity and Related Diseases, Official Journal of the American Society for Bariatric Surgery, vol. 5, No. 3S, pp. S48-S49, (May/Jun. 2009).

Herrera, et al., "Intermittent Vagal Blocking with an Implantable Device Reduces Maximum Tolerated Volume (MTV) During a Standardized Nutrient Drink Test in Obese Subjects," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 1012 (Aug. 2009).

Herrera, et al., "VBLOC and Improvements in Co-Morbidities in Obese Subjects During Weight Loss," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 983-984, (Aug. 2009).

Herrera, et al., "Vagal Blocking Improves Glycemic Control and Blood Pressure in Subjects with Type 2 Diabetes and Hypertension," 2010 Plenary Session / Supplement to Surgery for Obesity and Related Diseases, Official Journal of the American Society for Bariatric Surgery, vol. 2, No. 3, pp. S1-S26, (May/Jun. 2010).

Herrera, et al., "Treatment of Obesity-Related Type 2 Diabetes with Vagal Blocking," Obesity 2011 Abstract Supplement / Poster Abstracts—Monday, Oct. 3, 2011, Obesity vol. 19, sup. 1:S185, (Nov. 2011), www.obsesityjournal.org.

Kow, et al., "Comparison of Food Ingestion Disorders with Three Devices for Obesity," Obesity Surgery: Including Laparoscopy and Allied Care, Program and Abstracts of the 13th World Congress of

(56) References Cited

OTHER PUBLICATIONS

IFSO, Buenos Aires, Argentina, Sep. 24-27, 2008. An International Surgical Journal for Research and Treatment of Massive Obesity, vol. 18, No. 8, pp. 914-915 (Aug. 2008).
Kow, et. al. "Selecting Vagal Blocking Electrical Algorithms for Obesity Treatment," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, p. 924, (Aug. 2008).
Kow, et al., "Comparison of Food Ingestion disorders with Three Devices for Obesity Treatment," and Wilson, Richard, et al., "Intra-abdominal Vagal Blocking Reduces Body Weight with Associated Reductions in Heart Rate and Without Adverse Effects on Electrocardiographic Parameters," TOS 2008 Abstract Supplement / Poster Session 2 Abstracts, vol. 16, Supp. 1: S222, (Oct. 2008) www.obesityjournal.org.
Kow, et al., "An Implantable Vagal Blocking System to Treat Obesity: Laparoscopic Implantation Technique and Early Results in a proof-of-Principle Clinical Study", SAGES 2008 Emerging Technology Oral Abstracts, p. 295, www.sages.org.
Kow, et al., "Vagal Blocking Improves Obesity-Related Co-Morbidities in Obese Subjects with type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Wednesday Nov. 10 3:30 pm-5:00 pm, Tasmania Hotel Grand Chancellor, Hobart, Conference Program Handbook.
Kow, et al., "Vagal Blocking for the Treatment of Obesity Delivered Using the Fully Implantable Maestro Rechargeable System: 12 Month Results," Surgery for Obesity and Related Diseases: Emerging Technologies Session 2011, 7, pp. 363-364, (2011).
Sarr, M.G., et al., "The EMPOWER Study: Randomized, Prospective, Double-Blind, Multicenter Trial of Vagal Blockade to Induce Weight Loss in Morbid Obesity," Obes. Surg. Published Sep. 8, 2012, (12pp) Springer Science+Business Media, LLC (2012).
Toouli, et al., "Vagal Blocking for Obesity Control (VBLOC): Effects on Excess Weight Loss, Calorie Intake, Satiation and Satiety," Obesity Surgery: Including Laparoscopy and Allied Care, Program Issue, World Congress, Porto, Sep. 5-8, 2007. An International Surgical Journal for Research and Treatment of Massive Obesity, vol. 17, No. 8, p. 1043 (Aug. 2007).
Toouli, et al., "Intra-Abdominal Vagal Blocking Reduces Calorie Intake, Enhances Satiation and Reduces Hunger during Significant and Sustained Weight Loss in Obese Subjects," Digestive Disease Week and the 109th Annual Meeting of the AGA Institute: May 17-22, 2008, San Diego, CA, Gastroenterology vol. 134, No. 4 (Suppl. 1) p. A-370 (Apr. 2008).
Toouli, et al., "Vagal Blocking for Obesity Control (VBLOC): Interim Six Months Results in an ongoing Trial Using a Second Generation System," 2008 Scientific Session of the Society of American Gastrointestinal and Endoscopic (SAGES), Philadelphia, Pennsylvania, USA Apr. 9-12, 2008. Poster Presentations, Surgical Endoscopy (2008) 22, p. S194, Springer Science+Business Media, LLC (2008).

Toouli, et al., "Vagal Blocking for Obesity Control (VBLOCTM): Ongoing Comparison of Weight Loss with Two Generations of an Active, Implantable Medical Device," 2008 Plenary Session II / Surgery for Obesity and Related Diseases, Official Journal of the American Society for Bariatric Surgery, et al., vol. 4, No. 3, p. 305, (May/Jun. 2008).
Toouli, et al., "Treatment of Obesity-Related Co-Morbidities with VBLOC Therapy," Obes. Surg. 21:998, Springer Science+Business Media, LLC (2011).
Toouli, et al., "Reduced Calorie Intake and Weight Loss During Vagal Bloc (VBLOC Therapy) in Morbidly Obese Patients with Type 2 Diabetes Mellitus," Gastroenterology 2011, vol. 140: S-619, AGA Institute.
Toouli, et al., "Vagal Blocking: Treatment of Obesity Related type 2 Diabetes and blood Pressure—18 Month Results," 24th Annual Scientific Conference of the Obesity Surgery Society of Australia and New Zealand, OSSANZ Conference 2012: Bariatric surgery-more than an operation, Apr. 11-13, Wednesday Nov. 11 3:30 pm-5:00 pm, Northern Territory Darwin Convention Centre, Darwin, Conference Program Handbook.
Tweden, et al., "Vagal Blocking for Obesity Control (VBLOC): Concordance of Effects of Very High Frequency Blocking Current At the Neural and Organ Levels Using Two Preclinical Models," Gastroenterology 2006, vol. 130 (suppl2 2) A-148, AGA Institute.
Tweden, et al., "Vagal Blocking Treatment of Obesity Related Type 2 Diabetes and Blood Pressure—18 Month Results," 5th Congress of the International Federation for the surgery of Obesity and Metabolic Disorders European Chapter (IFSO-EC), Barcelona '12, Apr. 26-28, 2012.
Tweden, et al., "Vagal Blocking for Obesity Control (VBLOC): Studies of Pancreatic and Gastric Function and Safety in a Porcine Model," Plenary Session 2006/2 Surgery for Obesity and Related Diseases, Official Journal of the American Society for Bariatric Surgery, vol. 2, No. 3, pp. 301-302, (May/Jun. 2006).
Tweden, et al. "Vagal Blocking for Obesity Control (VBLOC): Studies of Pancreatic Function and Safety in a Porcine Model," Obesity Surgery: Including Laparoscopy and Allied Care, Program Issue, World Congress, Australia, Aug. 30-Sep. 2, 2006. An International Surgical Journal for Research and Treatment of Massive Obesity, vol. 16, No. 8, p. 988, (Aug. 2006).
Waataja, Jonathan J., et al., "Effects of High-Frequency Alternating Current on Axonal Conduction Through the Vagus Nerve," Journal of Neural Engineering Neural Eng. 8 (2011) (1741-1747) IOP Publishing Ltd, (2011) online at stacks.iop.org.
Wilson., et al., "Intra-Abdominal Vagal Blocking Reduces body Weight with Associated Reductions in Heart Rate and Without Adverse Effects on Electrocardiographic Parameters," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, p. 923 (Aug. 2008).
Chinese Office Action for related Chinese patent application 201380023723.7 mailed Jul. 30, 2015.

* cited by examiner

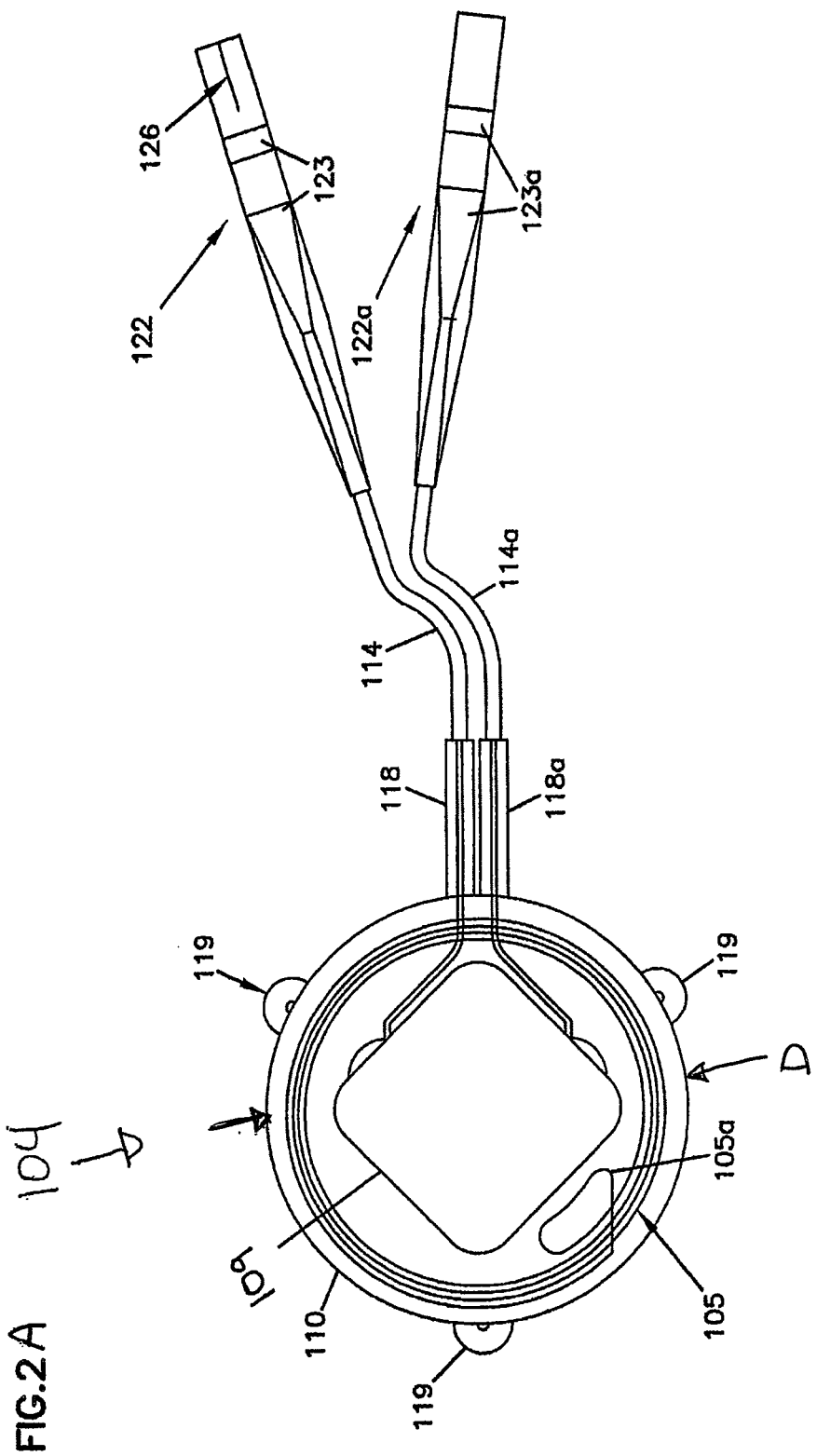

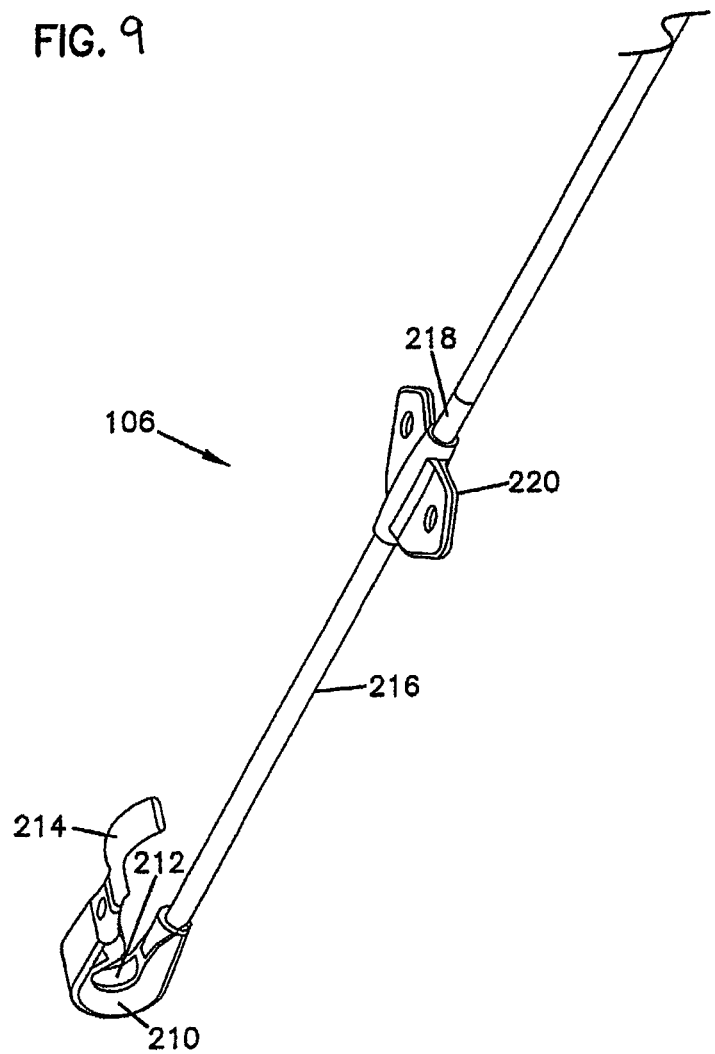

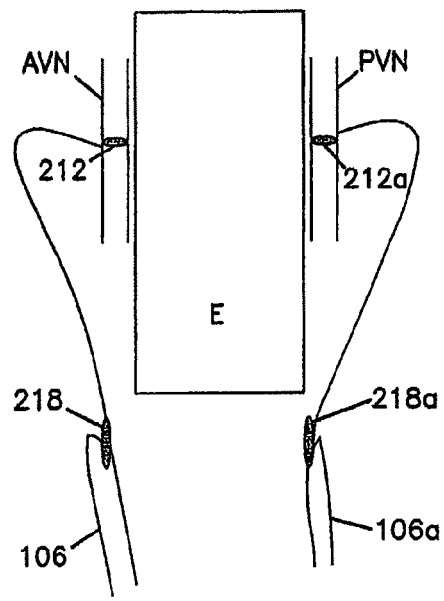
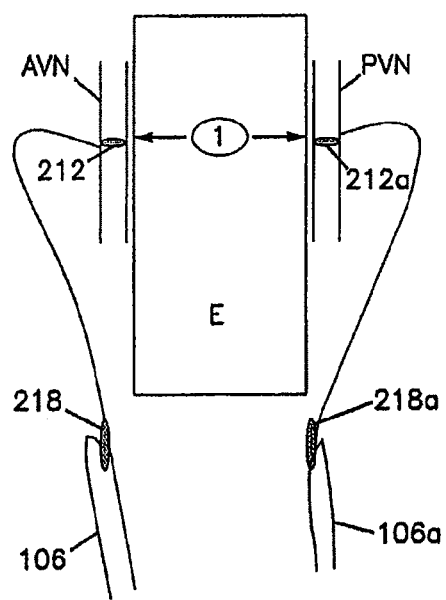
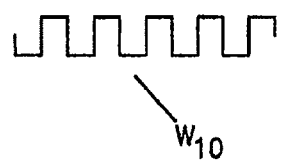

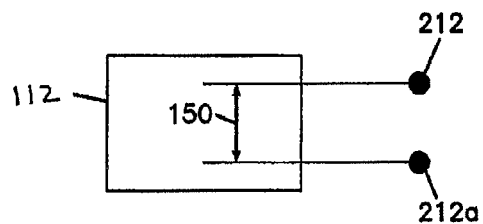
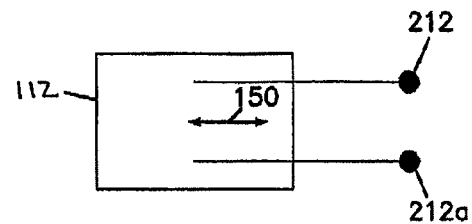
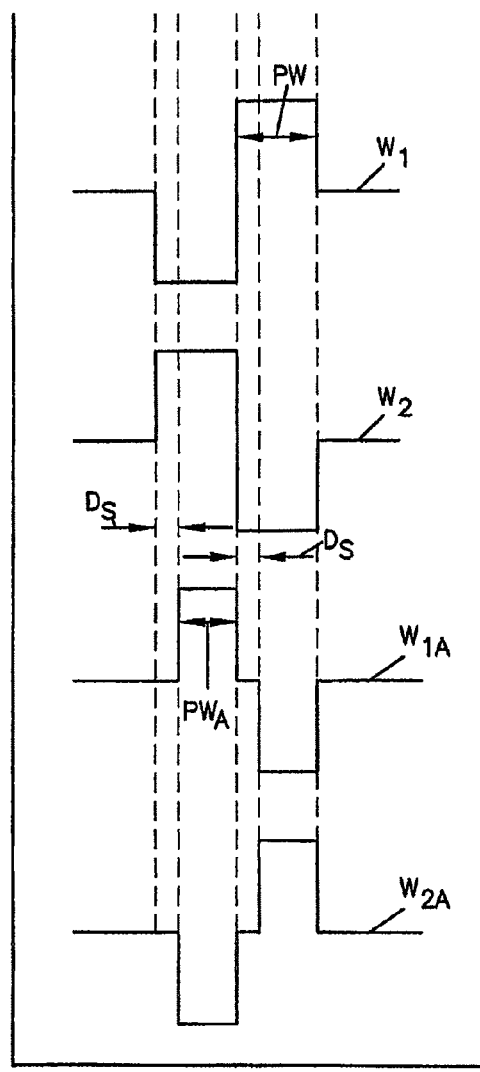

SAFETY FEATURES FOR USE IN MEDICAL DEVICES

CROSS REFERENCE

This application claims priority to U.S. Application No. 61/608,949 filed Mar. 9, 2012, which application is hereby incorporated by reference.

BACKGROUND OF THE INVENTION

1. Field of the Invention

This invention pertains to systems for applying electrical signals to an anatomical feature of a patient. While many of the disclosed concepts are applicable to a wide variety of therapies (e.g., cardiac pacing with electrodes applied to heart tissue), the invention is described in a preferred embodiment where the invention pertains to the treatment of disorders such as obesity, pancreatitis, irritable bowel syndrome, diabetes, hypertension, metabolic disease, and inflammatory disorders. In a most preferred embodiment, this invention pertains to the treatment of a gastrointestinal disorder by the application of a high frequency signal to a vagus nerve of a patient.

2. Background

A blocking therapy can be used alone or in combination with traditional electrical nerve stimulation in which impulses are created for propagation along a nerve. The disorders to be treated include, without limitation, functional gastrointestinal disorders (FGIDs) (such as functional dyspepsia (dysmotility-like) and irritable bowel syndrome (IBS)), gastroparesis, gastroesophageal reflux disease (GERD), obesity, pancreatitis, diabetes, hypertension, metabolic disease, inflammation, discomfort and other disorders.

In a blocking therapy, an electrode (or multiple electrodes) is placed on or near a vagus nerve or nerves of a patient. By "near", it is meant close enough that a field created by the electrode captures the nerve. Higher frequencies (e.g., 2,500 Hz-20,000 Hz) are believed to result in more consistent neural conduction block. Particularly, the nerve conduction block is applied with an electrical signal selected to block the entire cross-section of the nerve (e.g., both afferent and efferent signals on both myelinated and non-myelinated fibers) at the site of application of the blocking signal.

A complete system for applying a signal to a nerve may include systems for addressing the potential for charge build-up, assuring good communication between implanted and external components, recharging implantable batteries, safety of the device, physician and patient controls and programming and communication with the system.

SUMMARY OF THE INVENTION

According to an embodiment of the present invention, a therapy system is disclosed for applying therapy to an internal anatomical feature of a patient. The system includes at least one electrode for implantation within the patient and placement at the anatomical feature (e.g., a nerve) for applying the therapy signal to the feature upon application of a treatment signal to the electrode. An implantable component is placed in the patient's body beneath a skin layer and coupled to the electrode. The implantable component includes an implanted antenna. An external component has an external antenna for placement above the skin and adapted to be electrically coupled to the implanted antenna across the skin through radiofrequency transmission.

A still further aspect of the present disclosure includes a method and system for performing a safety check in an implantable medical device. In embodiments, a medical device configured to conduct a safety check comprises a first electrical lead, including a first tip connection and a first ring connection; a second electrical lead, including a second tip connection and second ring connection; a voltage supply connection; a field programmable gate array; a microprocessor electrically connected to the field programmable gate array; a first current source; a first grounding connection; a first sensing resistor electrically connected to the first current source and the first grounding connection; a digital to analog convertor electrically connected to the microprocessor and the first current source; an analog to digital convertor electrically connected to first sensing resistor and the microprocessor; and a first H-bridge circuit including first and second pairs of series electrical switches connected in parallel, and electrically connected to the field programmable gate array, the voltage supply connection, the first current source, and the first electrical lead; and wherein: the first tip connection is electrically connected between the first pair of series electrical switches of the first H-bridge circuit; the first ring connection is electrically connected between the second pairs of series electrical switches of the first H-bridge circuit.

In other embodiments, the medical device further comprises a second current source electrically connected to the digital to analog converter; a second grounding connection, a second sensing resistor electrically connected to the second current source and the second grounding connection; a second analog to digital converter electrically connected between the second current source and the microprocessor; a second digital to analog convertor electrically connected to the microprocessor and to the second current source; a second H-bridge circuit including first and second pairs of series electrical switches connected in parallel, and electrically connected to the field programmable gate array, the voltage supply connection, the second current source and the second electrical lead; and wherein: the second tip connection is electrically connected between the first of series electrical switches of the second H-bridge circuit; the second ring connection is electrically connected between the second pair of series electrical switches of the second H-bridge circuit.

The disclosure also provides a method of performing a safety check in an implantable medical device, during which electrical signals and therapy are not delivered to the patient, the method comprising: periodically initiating a sequence of tests of an H-bridge circuit of an implantable device, the implantable device comprising a H-bridge circuit, a field-programmable gate array ("FPGA"), a microprocessor, a current source, a voltage supply connection, a grounding connection, a current sensing resistor, and two pairs of series electrical switches connected in parallel between the voltage supply connection and the grounding connection, the sequence of tests selected to test each switch connection of the electrical switches in the H-bridge circuit; during each test, monitoring a current flow through a current sensing resistor electrically connected between the current source of the H-bridge circuit and a ground, wherein current flow through the current sensing resistor indicates that both series electrical switches within at least one of the two pairs of series electrical switches are active during that test. In other embodiments, the method comprises receiving signals indicative of a voltage drop across the current sensing resistor by the microprocessor, the microprocessor electrically coupled to the H-bridge circuit; processing the signals to determine the current flow through the sensing resistor by the microprocessor; and sending a resulting signal to the FPGA to continue therapy or to abort therapy, the FPGA electrically coupled to the microprocessor. In embodiments, if the current flow through the switches or lack thereof is abnormal (e.g. either present when it should not be or not present when it should be), the microprocessor will abort the therapy. In specific examples, the medical device is utilized to treat at least one of a plurality of gastrointestinal disorders of a patient.

In yet another aspect, a medical device is configured to apply an electrical stimulus to tissue of a patient. The medical device comprises, a first electrical lead, including a first tip connection and a first ring connection; a second electrical lead, including a second tip connection and second ring connection; a first H-bridge circuit, a first current source, a first voltage supply connection, a first grounding connection, and first, second, third, and fourth electrical switches, the first and second electrical switches connected in series to form a first pair and the third and fourth electrical switches connected in series to form a second pair, the first and second pairs connected in parallel with each other between the first voltage supply connection and the first grounding connection; a second H-bridge circuit, a second current source, a second voltage supply connection, a second grounding connection, and fifth, sixth, seventh, and eighth electrical switches, the fifth and sixth electrical switches connected in series to form a third pair and the seventh and eighth electrical switches connected in series to form a fourth pair, the third and fourth pairs connected in parallel with each other between the second voltage supply connection and the second grounding connection; a first electrical lead including a first tip connection electrically connected between the first and second electrical switches and a first ring connection electrically connected between the third and fourth electrical switches; a second electrical lead including a second tip connection electrically connected between the fifth and sixth electrical switches and a second ring connection electrically connected between the seventh and eight electrical switches.

Another aspect of the disclosure provides systems and methods for calibrating an output current. In embodiments, a medical device comprises a first electrical lead configured to be implanted in a patient and to introduce electrical signals at a nerve, such as the vagal nerve, the first electrical lead having electrode connections including a first tip connection and a first ring connection; a second electrical lead configured to be implanted in a patient and to introduce electrical signals at a nerve, such as the vagal nerve, the second electrical lead having electrode connections including a second tip connection and a second ring connection; a voltage source; at each of the first and second tip connections and first and second ring connections, a first capacitor and a second capacitor connected in series between the respective electrode connection and a ground; a programmable circuit electrically connected to locations between each of the first and second capacitors, the programmable circuit configured to execute program instructions which, when executed, cause the programmable circuit to: calculate initial capacitive ratios between the first capacitor and the second capacitor for each of the first and second tip connections and first and second ring connections; store each of the initial capacitive ratios in a memory associated with the programmable circuit; prior to initiating delivery of an electrical therapy to a patient via the first and second electrical leads, calculating second capacitive ratios between the first capacitor and the second capacitor for each of the first and second tip connections and first and second ring connections; compare each of the second capacitive ratios to the respective initial capacitive ratios to validate the integrity of the capacitive divider network.

In yet another aspect of the disclosure methods and systems are provided for charging a battery in an implantable device. In embodiments, a medical device comprises an implantable neuroregulator comprising a) a temperature sensor; b) a rechargeable battery; c) a microprocessor configured to obtain a baseline temperature of the implantable neuroregulator, to obtain a charge level of the battery, to ascertain the type of battery, to determine a level of charge to charge the battery, and to select between a constant rate of charge for the battery and/or a variable rate of charge for the battery, d) the microprocessor configured to send a communication indicating acceptance of charge, level of charge, a constant rate or variable rate of charge, and duration of the charge to an external component; d) the microprocessor configured to determine if the rate of rise of the temperature or if the temperature exceeds a predetermined maximum as compared to the baseline, and configured to communicate to the external charger to stop sending charge or to change the power level of the charge if the rate of temperature rise exceeds a predetermined maximum or if the temperature exceeds a predetermined maximum; and ii) an external charger configured to generate charge to charge the battery at a level selected by the implantable neuroregulator, configured to modify the charge level upon request by the implantable neuroregulator, configured to deliver charge at a constant or variable rate, and configured to stop charging upon request by the implantable neuroregulator.

In embodiments, a method of recharging an implantable module containing a rechargeable battery, in which the rate of rise of temperature of the module is measured or the rise of temperature of the module is measured over a specified time, and the charging current is adjusted to ensure that the temperature does not prematurely exceed the predetermined temperature limit established by the Cenelec European Standard EN 45502-1 (August 1997, page 18, paragraph 17.1. In other embodiments, a method comprises measuring a baseline temperature of the implantable neuroregulator; and selecting a constant or variable rate of charge of the battery based on current or voltage during a selected charge session by the implantable neuroregulator, wherein the constant or variable rate of charge is selected to not cause an increase in temperature of the implantable neuroregulator beyond a predetermined maximum safe temperature over a baseline temperature.

Another aspect of the disclosure provides systems and methods for calibrating a clock of an implantable component. In embodiments, a medical device comprises an implantable neuroregulator including a microprocessor, the microprocessor including an integrated circuit and/or a crystal oscillator, a resistive capacitor circuit clock, and a programmable circuit configured to execute program instructions which, when executed, cause the programmable circuit to: count an actual number of oscillator transitions of the integrated circuit and/or crystal oscillator during a defined period of time; compare the actual count of oscillator transitions to an expected count of oscillator transitions, determine if the count is out of range and calculate an OscValue by determining the difference between that expected count and the actual count; set an a control register to a value that indicates the change in actual oscillator transitions during the defined period of time; and adjust oscillation of the integrated circuit clock based on the value in the control register.

In other embodiments, a medical device comprises an implantable neuroregulator including a microprocessor, the microprocessor including a an integrated circuit and/or a crystal oscillator, a resistive capacitor circuit clock, and a programmable circuit configured to execute program instructions which, when executed, cause the programmable circuit to: count the number of a downlink carrier frequency oscillations in a set number of resistive capacitor circuit clock cycles to determine the need to adjust the resistive capacitor circuit clock; determine if the actual oscillation frequency of the downlink carrier frequency is different than the expected downlink carrier frequency oscillation; adjust the resistive capacitor circuit clock oscillations based on any difference between the actual downlink carrier frequency oscillations from the expected downlink carrier frequency oscillation.

BRIEF DESCRIPTION OF THE DRAWINGS

The accompanying drawings, which are incorporated in and constitute a part of the description, illustrate several aspects of the invention and together with the description, serve to explain the principles of the invention. A brief description of the drawings is as follows:

FIG. 2A is a plan view of an implantable neuroregulator for use in the therapy system of FIG. 1 according to aspects of the present disclosure;

FIG. 9 is a perspective view of a distal portion of a bipolar therapy lead according to aspects of the present disclosure;

FIG. 10 is a schematic representation of an electrode placement for a blocking therapy according to aspects of the present disclosure;

FIG. 11 is a schematic representation of a first electrode configuration according to aspects of the present disclosure;

FIG. 12 is a schematic representation of a typical waveform according to aspects of the present disclosure;

FIG. 22 is a schematic illustration of a charge balancing system shown in a shorting state according to aspects of the present disclosure;

FIG. 23 is the view of FIG. 22 in a non-shorting state according to aspects of the present disclosure; and FIG. 24 is a graphical illustration comparing waveforms in shorting and non-shorting states according to aspects of the present disclosure.

DETAILED DESCRIPTION

With reference now to the various drawing figures in which identical elements are numbered identically throughout, a description of the preferred embodiment of the present invention will now be described.

Figure 1:
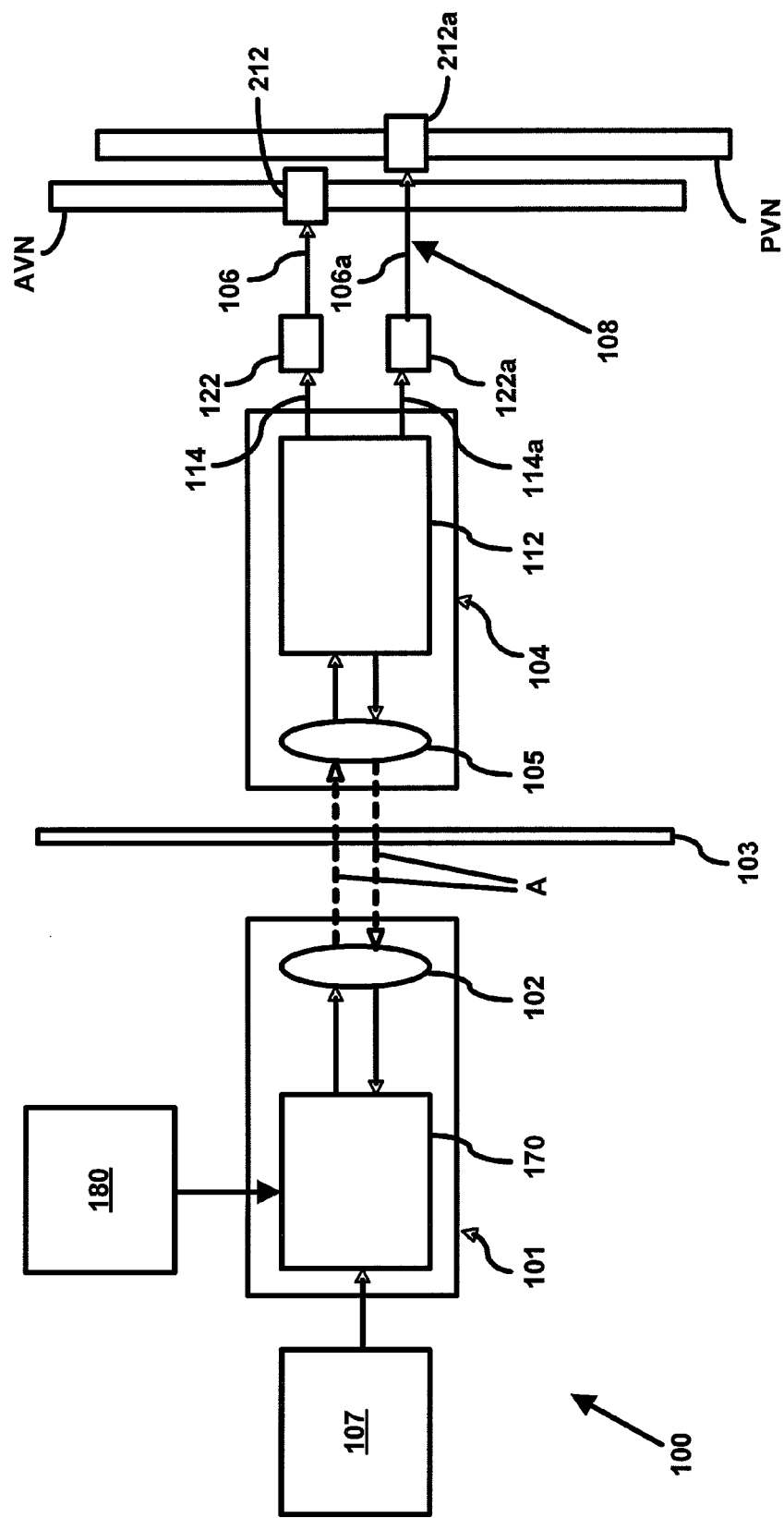
FIG. 1 is a schematic representation of a therapy system having features that are examples of inventive aspects of the principles of the present invention, the therapy system including a neuroregulator and an external charger.

FIG. 1 schematically illustrates a therapy system 100 for treating conditions or disorder such as obesity, pancreatitis, irritable bowel syndrome, diabetes, hypertension, metabolic disease, and inflammatory disorders. The therapy system 100 includes a neuroregulator 104, an electrical lead arrangement 108, and an external charger 101. The neuroregulator 104 is adapted for implantation within a patient to be treated for obesity. As will be more fully described herein, the neuroregulator 104 typically is implanted just beneath a skin layer 103.

The neuroregulator 104 is configured to connect electrically to the lead arrangement 108. In general, the lead arrangement 108 includes two or more electrical lead assemblies 106, 106a. In the example shown, the lead arrangement 108 includes two identical (bipolar) electrical lead assemblies 106, 106a. The neuroregulator 104 generates therapy signals and transmits the therapy signals to the lead assemblies 106, 106a.

The lead assemblies 106, 106a up-regulate and/or down-regulate nerves of a patient based on the therapy signals provided by the neuroregulator 104. In an embodiment, the lead assemblies 106, 106a include distal electrodes 212, 212a, which are placed on one or more nerves of a patient. For example, the electrodes 212, 212a may be individually placed on the anterior vagal nerve AVN and posterior vagal nerve PVN, respectively, of a patient. For example, the distal electrodes 212, 212a can be placed just below the patient's diaphragm. In other embodiments, however, fewer or more electrodes can be placed on or near fewer or more nerves.

The external charger 101 includes circuitry for communicating with the implanted neuroregulator 104. In general, the communication is transmitted across the skin 103 along a two-way signal path as indicated by arrows A. Example communication signals transmitted between the external charger 101 and the neuroregulator 104 include treatment instructions, patient data, and other signals as will be described herein. Energy also can be transmitted from the external charger 101 to the neuroregulator 104 as will be described herein.

In the example shown, the external charger 101 can communicate with the implanted neuroregulator 104 via bidirectional telemetry (e.g. via radiofrequency (RF) signals). The external charger 101 shown in FIG. 1 includes a coil 102, which can send and receive RF signals. A similar coil 105 can be implanted within the patient and coupled to the neuroregulator 104. In an embodiment, the coil 105 is integral with the neuroregulator 104. The coil 105 serves to receive and transmit signals from and to the coil 102 of the external charger 101.

For example, the external charger 101 can encode the information as a bit stream by amplitude modulating or frequency modulating an RF carrier wave. The signals transmitted between the coils 102, 105 preferably have a carrier frequency of about 6.78 MHz. For example, during an information communication phase, the value of a parameter can be transmitted by toggling a rectification level between half-wave rectification and no rectification. In other embodiments, however, higher or lower carrier wave frequencies may be used.

In an embodiment, the neuroregulator 104 communicates with the external charger 101 using load shifting (e.g., modification of the load induced on the external charger 101). This change in the load can be sensed by the inductively coupled external charger 101. In other embodiments, however, the neuroregulator 104 and external charger 101 can communicate using other types of signals.

In an embodiment, the neuroregulator 104 receives power to generate the therapy signals from an implantable power source 151 (see FIG. 3A), such as a battery. In a preferred embodiment, the power source 151 is a rechargeable battery. In some embodiments, the power source 151 can provide power to the implanted neuroregulator 104 when the external charger 101 is not connected. In other embodiments, the external charger 101 also can be configured to provide for periodic recharging of the internal power source 151 of the neuroregulator 104. In an alternative embodiment, however, the neuroregulator 104 can entirely depend upon power received from an external source (see FIG. 3B). For example, the external charger 101 can transmit power to the neuroregulator 104 via the RF link (e.g., between coils 102, 105).

In some embodiments, the neuroregulator 104 initiates the generation and transmission of therapy signals to the lead assemblies 106, 106a. In an embodiment, the neuroregulator 104 initiates therapy when powered by the internal battery 151. In other embodiments, however, the external charger 101 triggers the neuroregulator 104 to begin generating therapy signals. After receiving initiation signals from the external charger 101, the neuroregulator 104 generates the therapy signals (e.g., pacing signals) and transmits the therapy signals to the lead assemblies 106, 106a.

In other embodiments, the external charger 101 also can provide the instructions according to which the therapy signals are generated (e.g., pulse-width, amplitude, and other such parameters). In a preferred embodiment, the external charger 101 includes memory in which several predetermined programs/therapy schedules can be stored for transmission to the neuroregulator 104. The external charger 101 also can enable a user to select a program/therapy schedule stored in memory for transmission to the neuroregulator 104. In another embodiment, the external charger 101 can provide treatment instructions with each initiation signal.

Typically, each of the programs/therapy schedules stored on the external charger 101 can be adjusted by a physician to suit the individual needs of the patient. For example, a computing device (e.g., a notebook computer, a personal computer, etc.) 107 can be communicatively connected to the external charger 101. With such a connection established, a physician can use the computing device 107 to program therapies into the external charger 101 for either storage or transmission to the neuroregulator 104.

The neuroregulator 104 also may include memory 152 (see FIGS. 3A and 3B) in which treatment instructions and/or patient data can be stored. For example, the neuroregulator 104 can store therapy programs indicating what therapy should be delivered to the patient. The neuroregulator 104 also can store patient data indicating how the patient utilized the therapy system 100 and/or reacted to the delivered therapy.

Figure 3A:
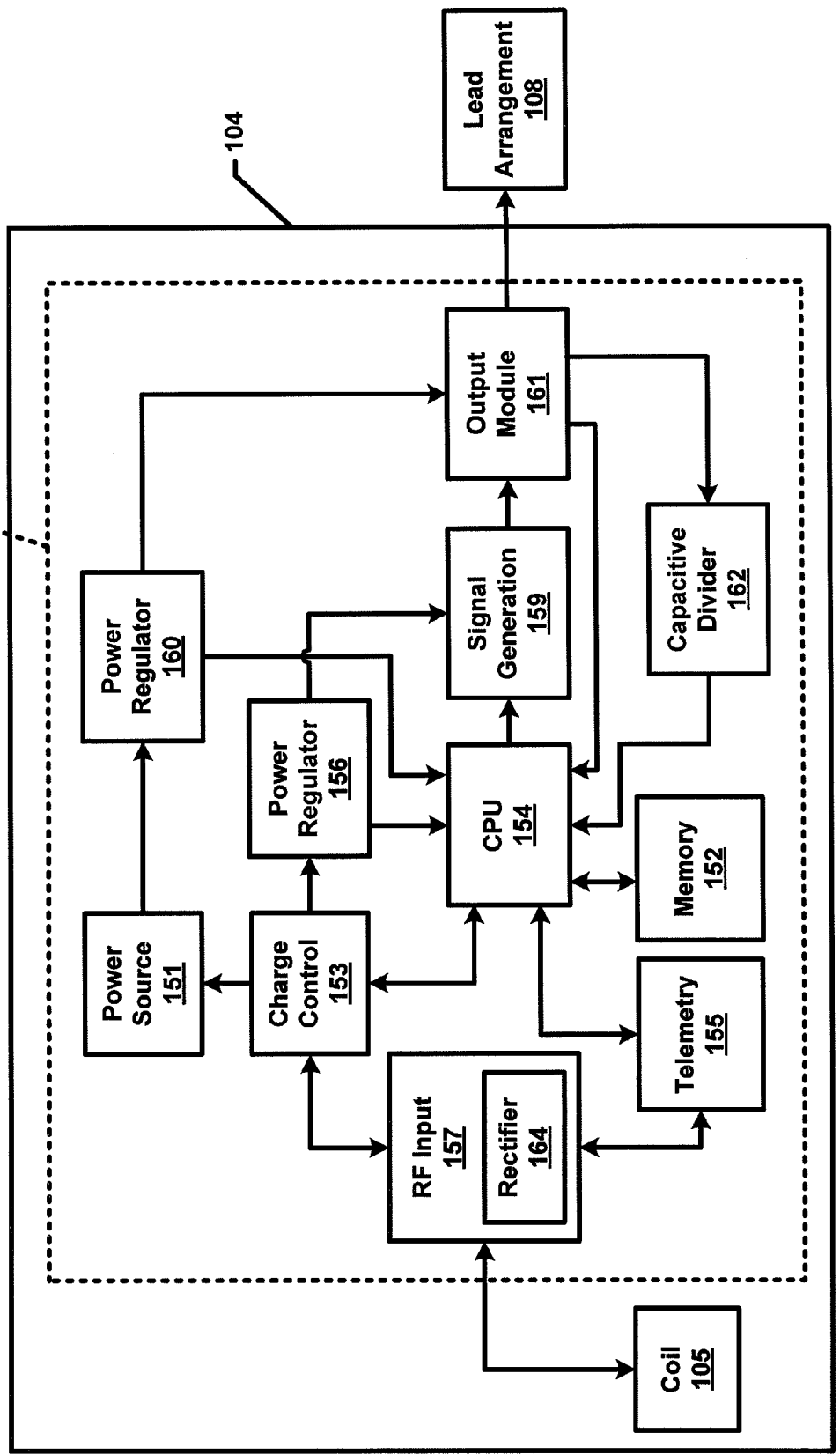
FIG. 3A is a block diagram of a representative circuit module for the neuroregulator of FIG. 2A and FIG. 2B according to aspects of the present disclosure.

In what follows, the focus of the detailed description is the preferred embodiment in which the neuroregulator 104 contains a rechargeable battery 151 from which the neuroregulator 104 may draw power (FIG. 3A).

1. System Hardware Components a. Neuroregulator

Figure 2B:
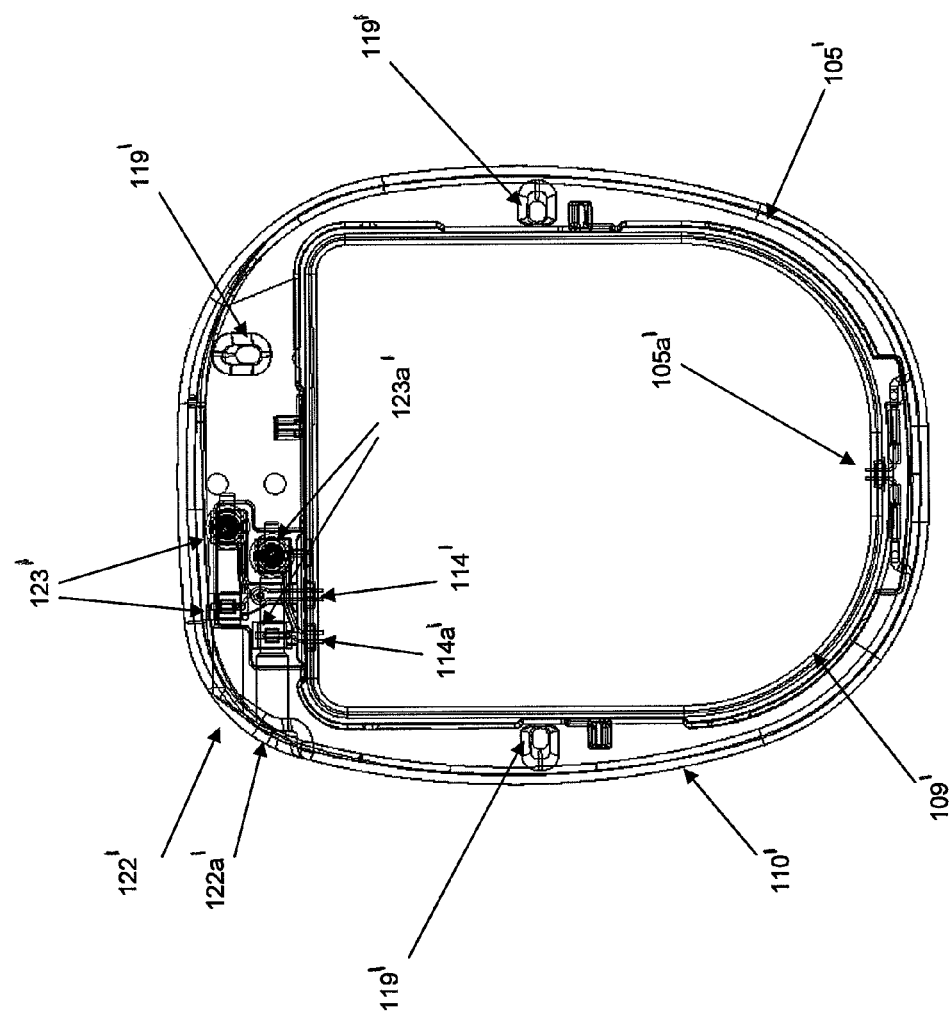
FIG. 2B is a plan view of another implantable neuroregulator for use in the therapy system of FIG. 1 according to aspects of the present disclosure.

Different embodiments of the neuroregulator 104, 104' are illustrated schematically in FIGS. 2A and 2B, respectively. The neuroregulator 104, 104' is configured to be implanted subcutaneously within the body of a patient. Preferably, the neuroregulator 104, 104' is implanted subcutaneously on the thoracic sidewall in the area slightly anterior to the axial line and caudal to the arm pit. In other embodiments, alternative implantation locations may be determined by the implanting surgeon.

The neuroregulator 104, 104' is generally sized for such implantation in the human body. By way of non-limiting example, an outer diameter D, D' of the neuroregulator 104, 104' is typically less than or equal to about sixty mm and a thickness of the neuroregulator 104, 104' is less than or equal to about fifteen mm. In a preferred embodiment, the neuroregulator 104, 104' has a maximum outer diameter D, D' of about fifty-five mm and a maximum thickness of about nine mm. In one embodiment, the neuroregulator 104, 104' weighs less than about one hundred twenty grams.

Typically, the neuroregulator 104, 104' is implanted parallel to the skin surface to maximize RF coupling efficiency with the external charger 101. In an embodiment, to facilitate optimal information and power transfer between the internal coil 105, 105' of the neuroregulator 104, 104' and the external coil 102 of the external charger 101, the patient can ascertain the position of the neuroregulator 104, 104' (e.g., through palpation or with the help of a fixed marking on the skin). In an embodiment, the external charger 101 can facilitate coil positioning as discussed herein with reference to FIGS. 7 and 8.

As shown in FIGS. 2A and 2B, the neuroregulator 104, 104' generally includes a housing 109, 109' overmolded with the internal coil 105, 105', respectively. The overmold 110, 110' of the neuroregulator 104, 104' is formed from a bio-compatible material that is transmissive to RF signals (i.e., or other such communication signals). Some such bio-compatible materials are well known in the art. For example, the overmold 110, 110' of the neuroregulator 104, 104' may be formed from silicone rubber or other suitable materials. The overmold 110, 110' also can include suture tabs or holes 119, 119' to facilitate placement within the patient's body.

The housing 109, 109' of the neuroregulator 104, 104' also may contain a circuit module, such as circuit 112 (see FIG. 1, 3A, and 3B), to which the coil 105, 105' may be electrically connected along a path 105a, 105a'. The circuit module within the housing 109 may be electrically connected to the lead assemblies 106, 106a (FIG. 1) through conductors 114, 114a. In the example shown in FIG. 2A, the conductors 114, 114a extend out of the housing 109 through strain reliefs 118, 118a. Such conductors 114, 114a are well known in the art.

The conductors 114, 114a terminate at connectors 122, 122a, which are configured to receive or otherwise connect the lead assemblies 106, 106a (FIG. 1) to the conductors 114, 114a. By providing connectors 122, 122a between the neuroregulator 104 and the lead assemblies 106, 106a, the lead assemblies 106, 106a may be implanted separately from the neuroregulator 104. Also, following implantation, the lead assemblies 106, 106a may be left in place while the originally implanted neuroregulator 104 is replaced by a different neuroregulator.

As shown in FIG. 2A, the neuroregulator connectors 122, 122a can be configured to receive connectors 126 of the lead assemblies 106, 106a. For example, the connectors 122, 122a of the neuroregulator 104 may be configured to receive pin connectors (not shown) of the lead assemblies 106, 106a. In another embodiment, the connectors 122, 122a may be configured to secure to the lead assemblies 106, 106a using set-screws 123, 123a, respectively, or other such fasteners. In a preferred embodiment, the connectors 122, 122a are well-known IS-1 connectors. As used herein, the term "IS-1" refers to a connector standard used by the cardiac pacing industry, and is governed by the international standard ISO 5841-3.

In the example shown in FIG. 2B, female connectors 122', 122a' configured to receive the leads 106, 106a are molded into a portion of the overmold 110' of the neuroregulator 104'. The leads connectors 126 are inserted into these molded connectors 122', 122a' and secured via setscrews 123', 123a', seals (e.g., Bal Seals®), and/or another fastener.

The circuit module 112 (see FIGS. 1, 3A, and 3B) is generally configured to generate therapy signals and to transmit the therapy signals to the lead assemblies 106, 106a. The circuit module 112 also may be configured to receive power and/or data transmissions from the external charger 101 via the internal coil 105. The internal coil 105 may be configured to send the power received from the external charger to the circuit module 112 for use or to the internal power source (e.g., battery) 151 of the neuroregulator 104 to recharge the power source 151.

Figure 3B:
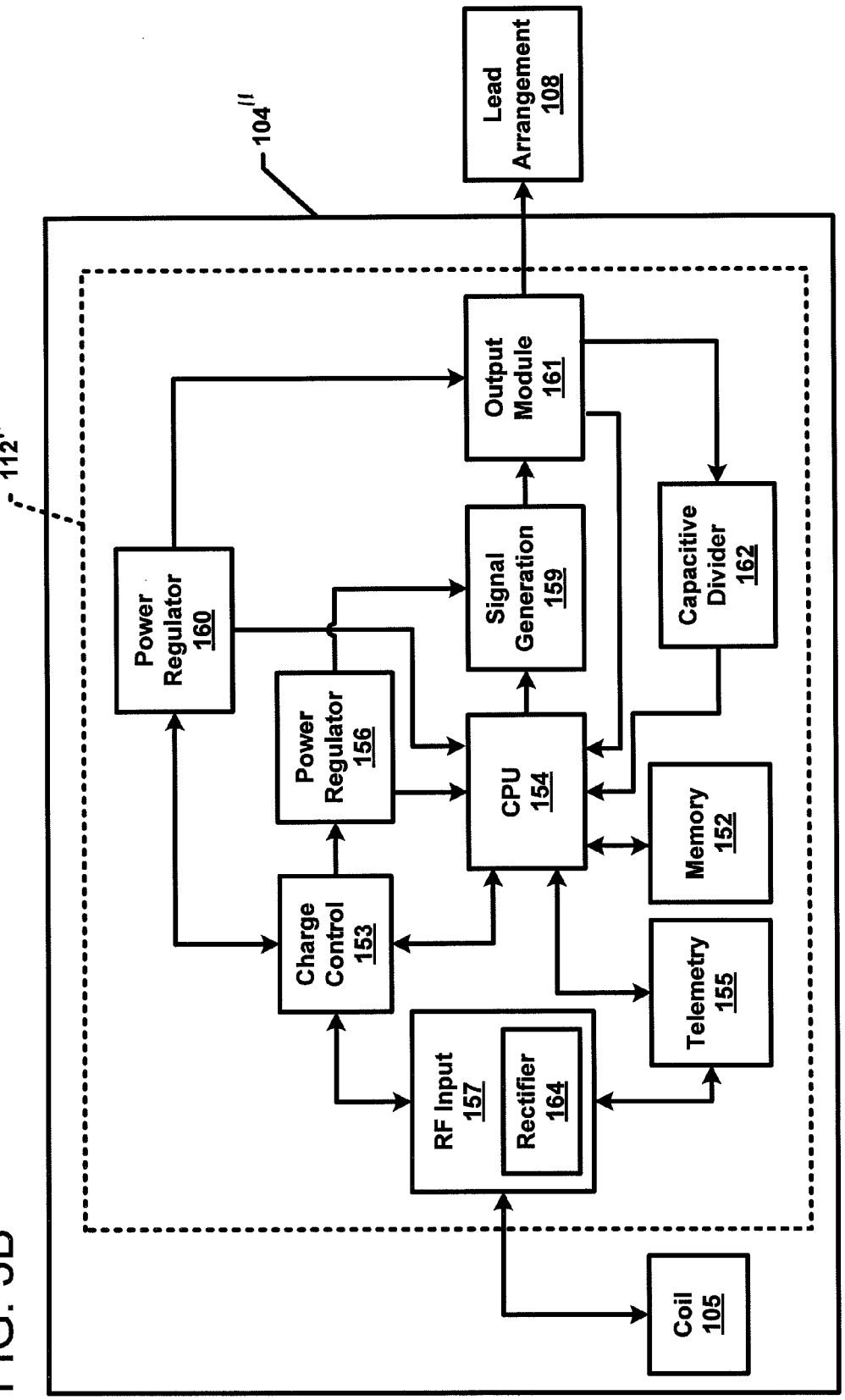
FIG. 3B is a block diagram of another representative circuit module for the neuroregulator of FIG. 2A and FIG. 2B according to aspects of the present disclosure.

Block diagrams of example circuit modules 112, 112" are shown in FIGS. 3A, 3B, respectively. Either circuit module 112, 112" can be utilized with any neuroregulator, such as neuroregulators 104, 104' described above. The circuit modules 112, 112" differ in that the circuit module 112 includes an internal power source 151 and a charge control module 153 and the circuit module 112" does not. Accordingly, power for operation of the circuit module 112" is provided entirely by the external charger 101 via the internal coil 105. Power operation for circuit module 112 may be provided by the external charger 101 or by the internal power source 151. Either circuit module 112, 112" may be used with either neuroregulator 104, 104' shown in FIGS. 2A, 2B. For ease in understanding, the following description will focus on the circuit module 112 shown in FIG. 3A.

The circuit module 112 includes an RF input 157 including a rectifier 164. The rectifier 164 converts the RF power received from the internal coil 105 into DC electric current. For example, the RF input 157 may receive the RF power from the internal coil 105, rectify the RF power to a DC power, and transmit the DC current to the internal power source 151 for storage. In one embodiment, the RF input 157 and the coil 105 may be tuned such that the natural frequency maximizes the power transferred from the external charger 101.

In an embodiment, the RF input 157 can first transmit the received power to a charge control module 153. The charge control module 153 receives power from the RF input 157 and delivers the power where needed through a power regulator 156. For example, the RF input 157 may forward the power to the battery 151 for charging or to circuitry for use in creating therapy signals as will be described below. When no power is received from the coil 105, the charge control 153 may draw power from the battery 151 and transmit the power through the power regulator 160 for use. For example, a central processing unit (CPU) 154 of the neuroregulator 104 may manage the charge control module 153 to determine whether power obtained from the coil 105 should be used to recharge the power source 151 or whether the power should be used to produce therapy signals. The CPU 154 also may determine when the power stored in the power source 151 should be used to produce therapy signals.

The transmission of energy and data via RF/inductive coupling is well known in the art. Further examples describing general requirements of recharging a battery via an RF/inductive coupling and controlling the proportion of energy obtained from the battery with energy obtained via inductive coupling can be found in the following references, all of which are hereby incorporated by reference herein: U.S. Pat. No. 3,727,616, issued Apr. 17, 1973, U.S. Pat. No. 4,612,934, issued Sep. 23, 1986, U.S. Pat. No. 4,793,353, issued Dec. 27, 1988, U.S. Pat. No. 5,279,292, issued Jan. 18, 1994, and U.S. Pat. No. 5,733,313, issued Mar. 31, 1998.

In general, the internal coil 105 may be configured to pass data transmissions between the external charger 101 and a telemetry module 155 of the neuroregulator 104. The telemetry module 155 generally converts the modulated signals received from the external charger 101 into data signals understandable to the CPU 154 of the neuroregulator 104. For example, the telemetry module 155 may demodulate an amplitude modulated carrier wave to obtain a data signal. In one embodiment, the signals received from the internal coil 105 are programming instructions from a physician (e.g., provided at the time of implant or on subsequent follow-up visits). The telemetry module 155 also may receive signals (e.g., patient data signals) from the CPU 154 and may send the data signals to the internal coil 105 for transmission to the external charger 101.

The CPU 154 may store operating parameters and data signals received at the neuroregulator 104 in an optional memory 152 of the neuroregulator 104. Typically, the memory 152 includes non-volatile memory. In other embodiments, the memory 152 also can store serial numbers and/or model numbers of the leads 106; serial number, model number, and/or firmware revision number of the external charger 101; and/or a serial number, model number, and/or firmware revision number of the neuroregulator 104.

The CPU 154 of the neuroregulator 104 also may receive input signals and produce output signals to control a signal generation module 159 of the neuroregulator 104. Signal generation timing may be communicated to the CPU 154 from the external charger 101 via the coil 105 and the telemetry module 155. In other embodiments, the signal generation timing may be provided to the CPU 154 from an oscillator module (not shown). The CPU 154 also may receive scheduling signals from a clock, such as 32 KHz real time clock (not shown).

The CPU 154 forwards the timing signals to the signal generation module 159 when therapy signals are to be produced. The CPU 154 also may forward information about the configuration of the electrode arrangement 108 to the signal generation module 159. For example, the CPU 154 can forward information obtained from the external charger 101 via the coil 105 and the telemetry module 155.

The signal generation module 159 provides control signals to an output module 161 to produce therapy signals. In an embodiment, the control signals are based at least in part on the timing signals received from the CPU 154. The control signals also can be based on the electrode configuration information received from the CPU 154.

The output module 161 produces the therapy signals based on the control signals received from the signal generation module 159. In an embodiment, the output module 161 produces the therapy signals by amplifying the control signals. The output module 161 then forwards the therapy signals to the lead arrangement 108.

In an embodiment, the signal generation module 159 receives power via a first power regulator 156. The power regulator 156 regulates the voltage of the power to a predetermined voltage appropriate for driving the signal generation module 159. For example, the power regulator 156 can regulate the voltage to about 2.5 volts.

In an embodiment, the output module 161 receives power via a second power regulator 160. The second power regulator 160 may regulate the voltage of the power in response to instructions from the CPU 154 to achieve specified constant current levels. The second power regulator 160 also may provide the voltage necessary to deliver constant current to the output module 161.

The output module 161 can measure the voltage of the therapy signals being outputted to the lead arrangement 108 and reports the measured voltage to the CPU 154. A capacitive divider 162 may be provided to scale the voltage measurement to a level compatible with the CPU 154. In another embodiment, the output module 161 can measure the impedance of the lead arrangement 108 to determine whether the leads 106, 106a are in contact with tissue. This impedance measurement also may be reported to the CPU 154.

b. External Charger

Figure 4:
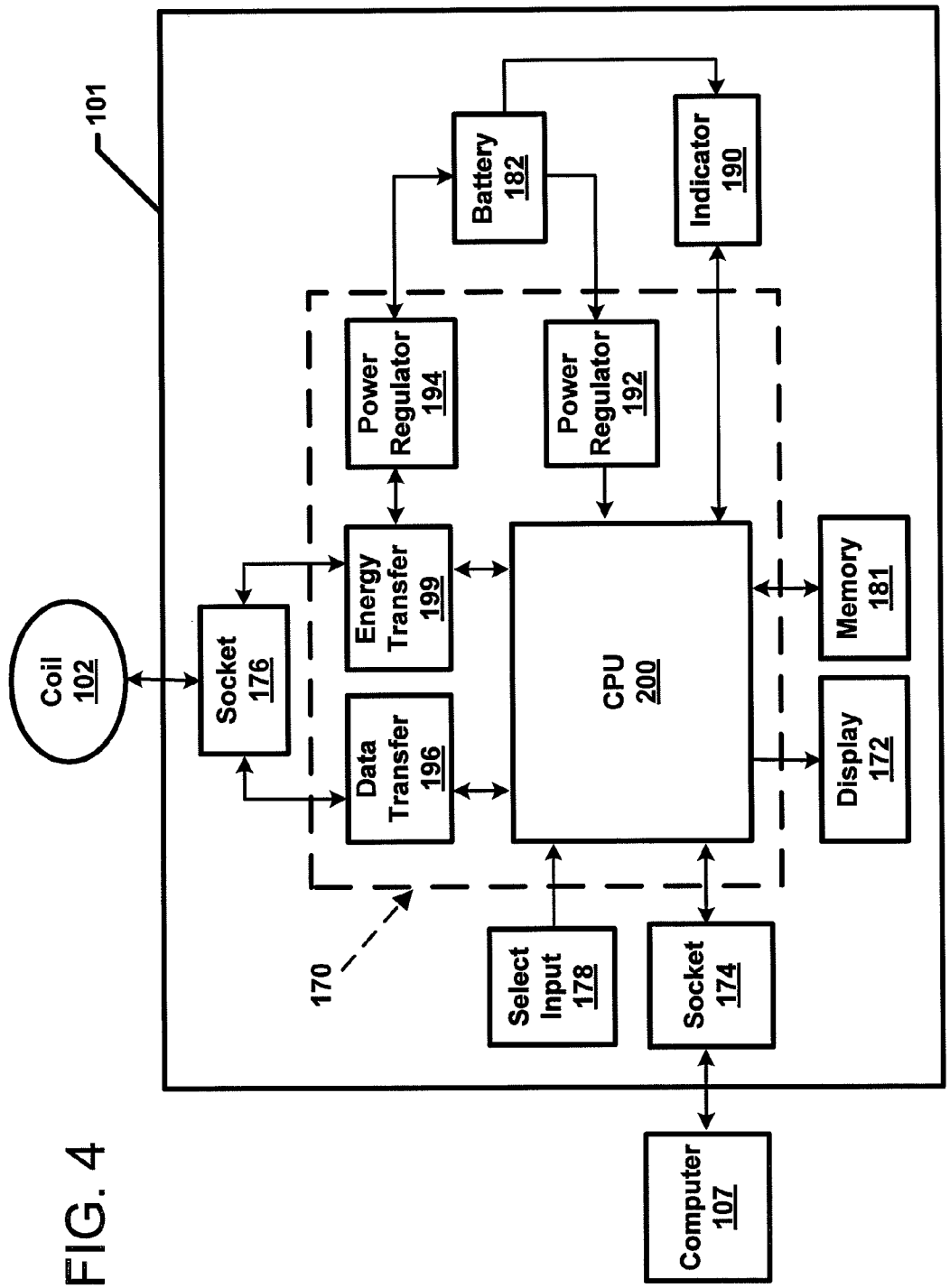
FIG. 4 is a block diagram of a circuit module for an external charger for use in the therapy system of FIG. 1 according to aspects of the present disclosure.

A block diagram view of an example external charger 101 is shown in FIG. 4. The example external charger 101 may cooperate with any of the neuroregulators 104, 104' discussed above to provide therapy to a patient. The external charger 101 is configured to transmit to the neuroregulator 104 (e.g., via an RF link) desired therapy parameters and treatment schedules and to receive data (e.g., patient data) from the neuroregulator 104. The external charger 101 also is configured to transmit energy to the neuroregulator 104 to power the generation of therapy signals and/or to recharge an internal battery 151 of the neuroregulator 104. The external charger 101 also can communicate with an external computer 107.

In general, the external charger 101 includes power and communications circuitry 170. The power and communications circuitry 170 is configured to accept input from multiple sources, to process the input at a central processing unit (CPU) 200, and to output data and/or energy (e.g., via coil 102, socket 174, or display 172). It will be appreciated that it is well within the skill of one of ordinary skill in the art (having the benefit of the teachings of the present invention) to create such circuit components with such function.

For example, the circuit power and communications circuit 170 can be electrically connected to the external coil 102 for inductive electrical coupling to the coil 105 of the neuroregulator 104. The power and communications circuit 170 also can be coupled to interface components enabling input from the patient or an external computing device (e.g., a personal computer, a laptop, a personal digital assistant, etc.) 107. For example, the external charger 101 can communicate with the computing device 107 via an electrically isolated Serial port.

The external charger 101 also includes a memory or data storage module 181 in which data received from the neuroregulator 104 (e.g., via coil 102 and socket input 176), the external computer 107 (e.g., via socket input 174), and/or the patient (e.g. via select input 178) can be stored. For example, the memory 181 can store one or more predetermined therapy programs and/or therapy schedules provided from the external computer 107. The memory 181 also can store software to operate the external charger 101 (e.g., to connect to the external computer 107, to program external operating parameters, to transmit data/energy to the neuroregulator 104, and/or to upgrades the operations of the CPU 200). Alternatively, the external charger 101 can include firmware to provide these functions. The memory 181 also can store diagnostic information, e.g., software and hardware error conditions.

An external computer or programmer 107 may connect to the communications circuit 170 through the first input 174. In an embodiment, the first input 174 is a port or socket into which a cable coupled to the external computer 107 can be plugged. In other embodiments, however, the first input 174 may include any connection mechanism capable of connecting the external computer 107 to the external charger 101. The external computer 107 provides an interface between the external charger 101 and a physician (e.g., or other medical professional) to enable the physician to program therapies into the external charger 101, to run diagnostic and system tests, and to retrieve data from the external charger 101.

The second input 176 permits the external charger 101 to couple selectively to one of either an external power source 180 or the external coil 102 (see FIG. 1). For example, the second input 176 can define a socket or port into which the power source 180 or external coil 102 can plug. In other embodiments, however, the second input 176 can be configured to couple to a cable or other coupling device via any desired connection mechanism. In one embodiment, the external charger 101 does not simultaneously connect to both the coil 102 and the external power source 180. Accordingly, in such an embodiment, the external power source 180 does not connect directly to the implanted neuroregulator 104.

The external power source 180 can provide power to the external charger 101 via the second input 176 when the external charger 101 is not coupled to the coil 102. In an embodiment, the external power source 180 enables the external charger 101 to process therapy programs and schedules. In another embodiment, the external power source 180 supplies power to enable the external charger 101 to communicate with the external computer 107 (see FIG. 1).

The external charger 101 optionally may include a battery, capacitor, or other storage device 182 (FIG. 4) enclosed within the external charger 101 that can supply power to the CPU 200 (e.g., when the external charger 101 is disconnected from the external power source 180). The power and communications circuit 170 can include a power regulator 192 configured to receive power from the battery 182, to regulate the voltage, and to direct the voltage to the CPU 200. In a preferred embodiment, the power regulator 192 sends a 2.5 volt signal to the CPU 200.

The battery 182 also can supply power to operate the external coil 102 when the coil 102 is coupled to the external charger 101. The battery 182 also can supply power to enable the external charger 101 to communicate with the external computer 107 when the external power source 180 is disconnected from the external charger 101. An indicator 190 may provide a visual or auditory indication of the remaining power in the battery 182 to the user.

In an embodiment, the battery 182 of the external charger 101 is rechargeable. For example, the external power source 180 may couple to the external charger 101 to supply a voltage to the battery 182. In such an embodiment, the external charger 101 then can be disconnected from the external power source 180 and connected to the external coil 102 to transmit power and/or data to the neuroregulator 104. Further details regarding example rechargeable systems include U.S. Pat. No. 6,516,227 to Meadows, issued Feb. 4, 2003; U.S. Pat. No. 6,895,280 to Meadows, issued May 17, 2005; and U.S. patent application Publication No. US 2005/0107841 to Meadows May 19, 2005, the disclosures of which are hereby incorporated herein by reference.

In an alternative embodiment, the battery 180 is a replaceable, rechargeable battery, which is recharged external to the external charger 101 in its own recharging stand. In yet another embodiment, the battery 182 in the external charger 101 can be a replaceable, non-rechargeable battery.

In use, energy from the external power source 180 flows through the second input 176 to an energy transfer module 199 of the power and communications circuit 170. The energy transfer module 199 directs the energy either to the CPU 200 to power the internal processing of the external charger 101 or to the battery 182. In an embodiment, the energy transfer module 199 first directs the energy to a power regulator 194, which can regulate the voltage of the energy signal before sending the energy to the battery 182.

In some embodiments, the external coil 102 of the external charger 101 can supply energy from the battery 182 to the internal coil 105 of the neuroregulator 104 (e.g., to recharge the internal power source 151 (FIG. 3) of the neuroregulator 104). In such embodiments, the energy transfer module 199 receives power from the battery 182 via the power regulator 194. For example, the power regulator 194 can provide a sufficient voltage to activate the energy transfer module 199. The energy transfer module 199 also can receive instructions from the CPU 200 regarding when to obtain power from the battery 182 and/or when to forward power to the external coil 102. The energy transfer module 199 delivers the energy received from the battery 182 to the coil 102 of the external charger 101 in accordance with the instructions provided by the CPU 200. The energy is sent from the external coil 102 to the internal coil 105 of the neuroregulator 104 via RF signals or any other desired power transfer signal. In an embodiment, therapy delivery at the neuroregulator 104 is suspended and power is delivered from the external charger 101 during recharging of the internal power source 151.

In some embodiments, the external charger 101 controls when the internal battery 151 of the implanted neuroregulator 104 is recharged. For example, the external charger 101 can determine when to recharge the battery 151. In other embodiments, however, the implanted neuroregulator 104 controls when the battery 151 is recharged as described herein. In embodiments, the external charger receives a communication from the implantable neuroregulator that it will accept charge, the level of charge requested, and the duration of charge. In embodiments, the external charger is configured to deliver charge energy at a number of different levels, for example, about 16 different levels. In embodiments, the external charger delivers charge energy until it receives a communication from the implantable neuroregulator to stop charging.

As noted above, in addition to power transmissions, the external coil 102 also can be configured to receive data from and to transmit programming instructions to the neuroregulator 104 (e.g., via an RF link). A data transfer module 196 may receive and transmit data and instructions between the CPU 200 and the internal coil 105. In an embodiment, the programming instructions include therapy schedules and parameter settings. Further examples of instructions and data transmitted between the external coil 102 and the implanted coil 105 are discussed in greater detail herein.

Figure 5:
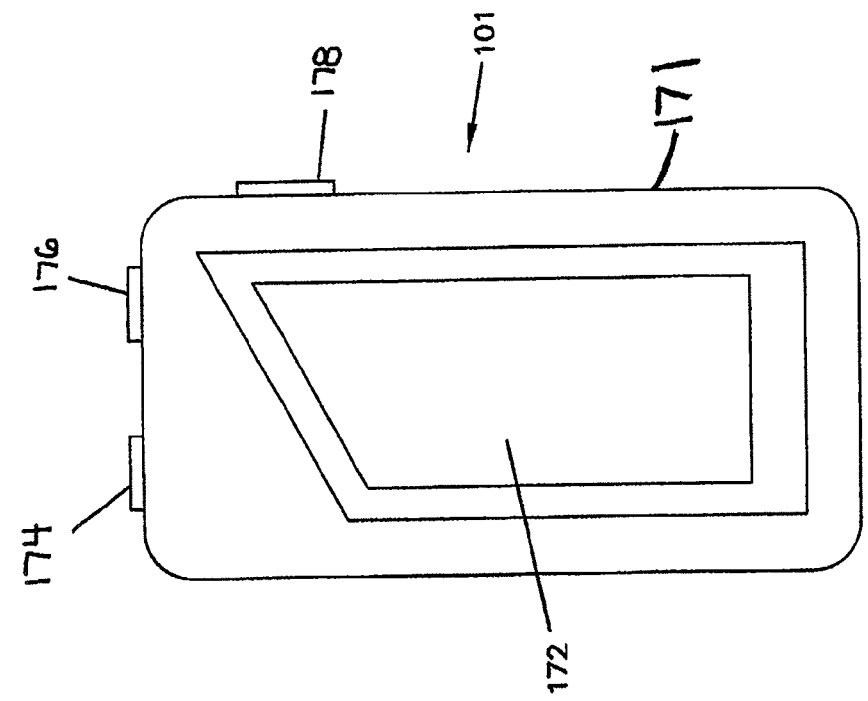
FIG. 5 is a plan schematic view of an example external charger for use in the therapy system of FIG. 1 according to aspects of the present disclosure.

FIG. 5 shows a front view of an example external charger 101. The external charger 101 includes a housing 171 defining a first input (e.g., socket input) 174, a second input (e.g., socket input) 176, and a third input (e.g., select input) 178 coupled to the communications circuit 170. In an embodiment, the housing 171 also may enclose a battery 182 configured to supply power to the external charger 101 via the power and communications circuit 170. Alternatively, the external charger 101 can receive power from an external source 180 (FIG. 1).

As shown in FIG. 5, visual display 172 also is provided on the housing 171 for presenting human readable information processed by the communications circuit 170. In an embodiment, the visual display 172 is a liquid crystal display (LCD) screen. In other embodiments, however, the visual display 172 can include any display mechanism (e.g., a light-emitting diode (LED) screen, vacuum fluorescent display (VFD) screen, etc.). Non-limiting examples of information that can be shown on the visual display 172 include the status of the battery 182 of the external charger 101, the status of the battery 151 in the implanted neuroregulator 104, coil position (as will be described), impedances between the electrodes 212, 212a and attached tissue, and error conditions.

As shown in FIG. 5, the third input 178 of the external charger 101 includes a selection input 178 with which the user can interact with the external charger 101. In an embodiment, the selection input 178 can include a button, which sequentially selects menu options for various operations performed by the external charger 101 when pressed successively. In other embodiments, however, the third input 178 includes another type of selection input (e.g., a touch screen, a toggle-switch, a microphone for accepting voice-activated commands, etc.).

Example functions capable of selection by the user include device reset, interrogation of battery status, interrogation of coil position, and/or interrogation of lead/tissue impedance. In other embodiments, a user also can select measurement of tissue/lead impedance and/or initiation of a stomach contraction test. Typically, the measurement and testing operations are performed when the patient is located in an operating room, doctor's office, or is otherwise surrounded by medical personnel.

In another embodiment, the user can select one or more programs and/or therapy schedules to submit to the memory 152 of the neuroregulator 104. For example, the user can cycle through available programs by repeatedly pressing the selection button 178 on the external charger 101. The user can indicate the user's choice by, e.g., depressing the selector button 178 for a predetermined period of time or pressing the selector button 178 in quick succession within a predetermined period of time.

In use, in some embodiments, the external charger 101 may be configured into one of multiple modes of operation. Each mode of operation can enable the external charger 101 to perform different functions with different limitations. In an embodiment, the external charger 101 can be configured into five modes of operation: an Operating Room mode; a Programming mode; a Therapy Delivery mode; a Charging mode; a Diagnostic mode and a Maintenance Mode.

When configured in the Operating Room mode, the external charger 101 can be used to determine whether the implanted neuroregulator 104 and/or the implanted lead arrangement 108 are functioning appropriately. If any component of the therapy system 100 is not functioning as desired, then the medical personnel can trouble-shoot the problem while still in the operation room or can abandon the procedure, if necessary.

For example, the external charger 101 can be used to determine whether the impedance at the electrodes 212, 212a of the lead arrangement 108 (FIG. 1) is within a prescribed range. When the impedance is within the prescribed range, a gastric contraction test can be initiated to demonstrate that the electrodes 212, 212a are appropriately positioned and can become active. If the impedance is outside an acceptable range, the system integrity can be checked (e.g. connections to the leads can be verified). Additionally, the therapy electrodes 212, 212a may be repositioned to provide better electrode-tissue contact.

In another embodiment, the external charger 101 can be used to initiate a stomach contraction test in the operating room. The stomach contraction test enables medical personnel to confirm the electrodes 212, 212a of the lead arrangement 108 (FIG. 1) are in contact with the appropriate nerves and not with some other tissue. For example, the external charger 101 can instruct the neuroregulator 104 to generate a signal tailored to cause the stomach to contract if the signal reaches the appropriate nerves.

Typically, the external charger 101 is not connected to an external computer 107 when configured in the Operating Room mode. In a preferred embodiment, the external charger is connected (e.g., via socket input 176) to a physician coil 102' (shown schematically in FIG. 6) instead of a patient coil 102 (described above). The physician coil 102' can differ from the patient coil 102 in one or more respects.

Figure 6:
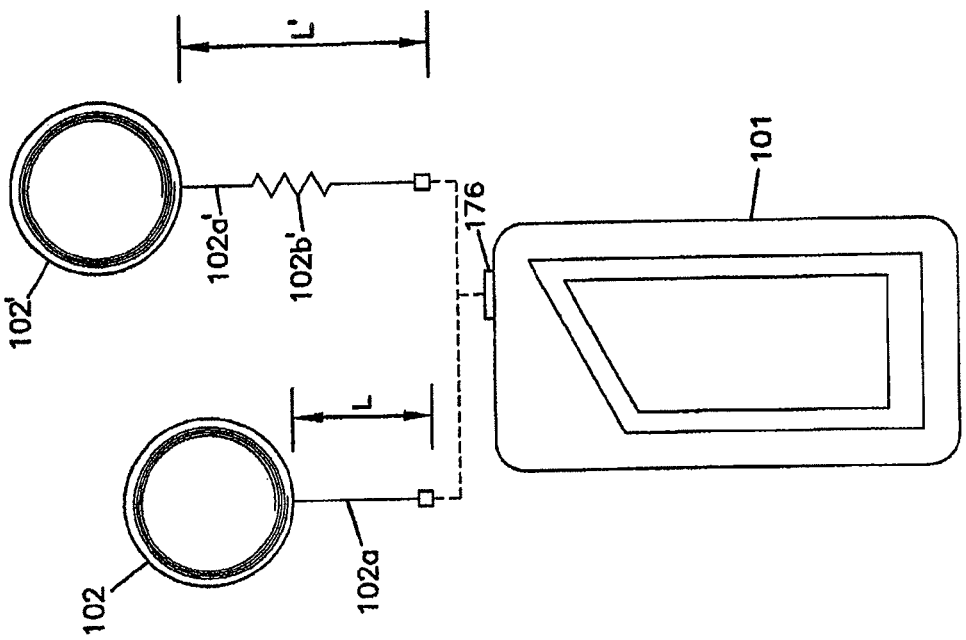
FIG. 6 is a plan, schematic view of an external charger and schematic views of a patient transmit coil and a physician transmit coil configured to couple to the external charger according to aspects of the present disclosure.

For example, as shown in FIG. 6, a length L' of the connection cable 102a' on the physician coil 102' can be longer than a length L of the cable 102a of the patient coil 102. In one example embodiment, the length L' of the connection cable 102a' of the physician coil 102' can be about 300 cm and the length L of the connection cable 102a of the patient coil 102 can be about 60 cm. The longer length L' allows the external charger 101 to be located outside the sterile field in the operating room when the physician coils 102' is connected.

In another embodiment, the physician coil 102' can include an indicator circuit to identify the coil 102' as a physician coil to the external charger 101. For example, the physician coil 102' can contain a small resistor 102b', which can be recognized by the external charger 101 when the physician coil 102' is plugged into the socket 176. When the external charger 101 detects the presence of the indicator circuit, the external charger 101 automatically configures itself into an Operating Room mode. This mode allows the physician to conduct various system and patient response tests, such as those described above, without the need for connection to a clinician computer 107.

When configured in the Programming mode, the external charger 101 is connected with the external computer 107 (FIG. 1) via which the physician manages the components of the therapy system 100. In general, the physician may select a therapy program and a therapy schedule stored on the external computer 107 to transfer to the external charger 101. In certain embodiments, the external charger 101 forwards the programs and schedule to the neuroregulator 104. In an embodiment, the external charger 101 can be coupled to the physician coil 102' during programming. In another embodiment, the external charger 101 can be coupled to the patient coil 102. In addition, in different embodiments, the external computer 107 also can assess the impedance of the electrodes 212, 212a, initiate system and/or diagnostic tests, and take corrective action when the external charger 101 is configured into the Programming mode.

After the neuroregulator 104 has been implanted and the external charger 101 and/or neuroregulator 104 have been programmed, the external charger 101 can be configured into the Therapy Delivery mode. When configured in the Therapy Delivery mode, the external charger 101 communicates with and/or powers the neuroregulator 104 as described above. Typically, the external charger 101 is coupled to the patient coil 102 and not to the external computer 107 when configured in the Therapy Delivery mode.

The external charger 101 also can interact with the user via the third input (e.g., the selector button) 178 and the display 172 to select the therapy to be provided. In an embodiment, the external charger 101 can send instructions indicating which program the neuroregulator 104 should follow while administering therapy. In another embodiment, the external charger 101 sends instructions in accordance with a selected program stored on the external charger 101.

If the neuroregulator 104 includes an internal power source 151, then the external charger 101 can enter a Charging mode in which the external charger 101 recharges the internal power source 151 of the neuroregulator 104 when the neuroregulator 104 is not delivering therapy. Typically, the external charger 101 enters the Charging mode at the request of the neuroregulator 104. In a preferred embodiment, the neuroregulator 104 controls how much power is sent by the external charger 101.

During follow-up visits between the patient and the physician, the external charger 101 may be configured into a Diagnostic mode. In this mode, the external charger 101 is coupled to the external computer 107 to provide an interface for the physician to obtain data stored on the external charger 101 and to download therapy and/or software updates. In an embodiment, the display 172 on the external charger 101 is disabled and all information is conveyed to the physician via the external computer 107 only. The external charger 101 may be coupled to either coil 102, 102' when configured in the Diagnostic mode.

In embodiments, a maintenance mode is one in which the neuroregulator delivers low energy electrical signals associated with safety checks and impedance checks for a period of time of 9 hours or less. In the interest of conserving battery power, the device may remain on but deliver the safety and impedance checks for 30 minutes to 9 hours, 1 hour to 8 hours, 1 hour to 7 hours, 1 hour to 6 hours, 1 hour to 5 hours, 1 hour to 4 hours, 1 hour to 3 hours and 1 hour to 2 hours. In embodiments, the safety checks are delivered at 50 Hz or less at least every 0.2 µs and impedance checks are delivered once every two minutes at a frequency of 1000 Hz or more. While not meant to limit the scope of the invention, it is believed that a therapeutic effect is associated with this low energy electrical single treatment if applied for at least 9 hours per day and not at shorter time periods. If the patient condition has stabilized or resolved, a health care provider may program the device for maintenance mode, leaving open the option to initiate a therapy program once again at a later date.

In an embodiment, the external charger 101 also can be configured into a Shipping mode, in which the battery 182 is disconnected from the rest of the circuitry. The Shipping mode avoids draining the battery 182 and enhances safety. In one such embodiment, pressing the selector button 172 causes the external charger 101 to change from this Shipping mode into another mode, such as the Therapy Delivery mode.

c. Alignment of External and Implanted Coils

The external charger 101 enables alignment of the relative positions of the external and implanted coils 102, 105 and optimization of the signal strength. Optimizing the alignment of the coils 102, 105 and the power of the transmission signal facilitates continuous, transcutaneous transmission of power and/or information.

i. Positioning of External Coil

In general, the external coil 102 is adapted to be placed on the patient's skin (e.g., by adhesives) overlying the implanted internal coil 105. The position and orientation of the coils 102, 105 can affect signal reliability. In addition, the strength of the transmission signals between the external coil 102 and the implanted coil 105 also is affected by the distance between the coils 102, 105. Implanting the neuroregulator 104 very close to the surface of the skin 103 typically results in a large and expanded range of signal strengths. Conversely, implanting the neuroregulator 104 at a large distance beneath the skin 103 yields a generally weak transmission link and a compressed range of signal strengths.

Figure 7:
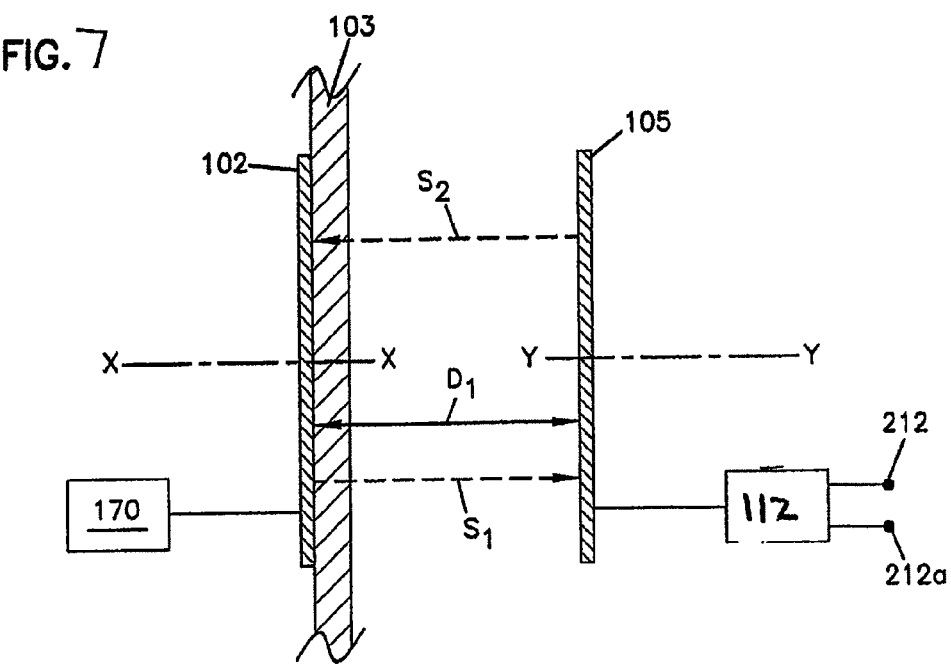
FIG. 7 is a side elevation, schematic view of an external coil in a desired alignment over an implanted coil according to aspects of the present disclosure.

FIG. 7 illustrates an external coil 102 appropriately aligned with an implanted coil 105. The coil 105 is implanted beneath the skin 103 at a preferred depth $D_1$ (e.g., about two centimeters to about three centimeters beneath the skin 103). Preferably, a plane of the coil 105 extends parallel to the surface of the skin 103. In an embodiment, each coil 102, 105 is a circular coil surrounding a central axis X-X, Y-Y, respectively. As shown in FIG. 7, in a preferred alignment configuration, the axes X-X, Y-Y are collinear so that there is no lateral offset of the axes X-X, Y-Y and the planes of the coils 102, 105 are parallel to one another. Such an alignment configuration may be attained, e.g., when the external coil 102 is applied to a patient's skin 103 when the patient is lying flat (e.g., on the patient's back).

Figure 8:
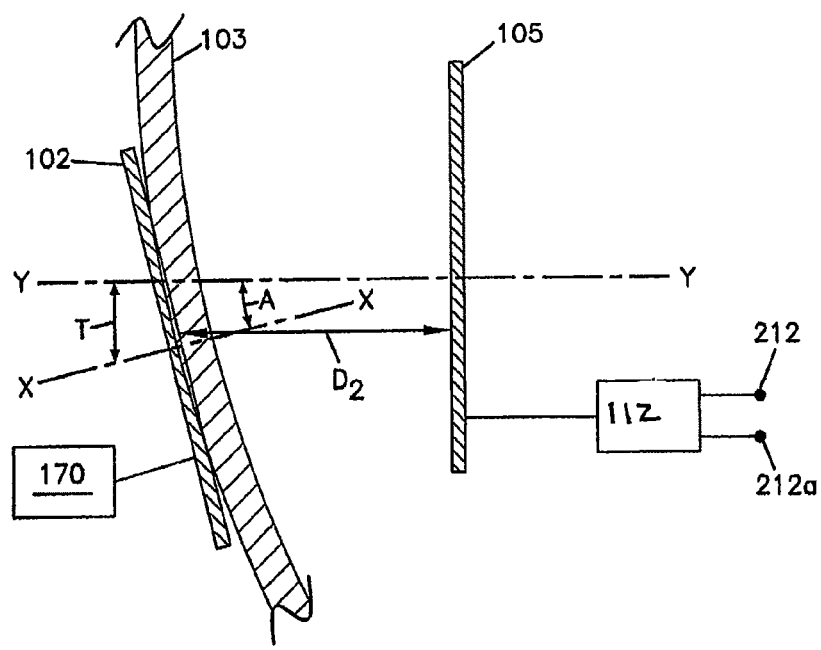
FIG. 8 illustrates the external coil and implanted coil of FIG. 7 arranged in a misaligned position according to aspects of the present disclosure.

FIG. 8 illustrates misalignment between the coils 102, 105 resulting from movement of the patient (e.g., a change in posture). For example, when the patient sits, excess fat may cause the skin 103 to roll. This rolling may cause the spacing between the coils 102, 105 to increase to a distance D2. Also, the orientation of the external coil 102 may change so that the axes X-X and Y-Y of the coils 102, 105, respectively, have a lateral offset T and an angular offset A. Such changes in spacing and orientation may be occurring constantly throughout the day.

The relative position of the coils 102, 105 may be optimized (e.g., for each use) when the external charger 101 senses the transmission link is weakened (e.g., on initial power up or when the energy transfer to the implantable neuroregulator 104 has degraded). For example, the external charger 101 can sound an alarm and invite the user to configure the external charger 101 into a Locate mode. Alternatively, the user can decide independently to enter the Locate mode (e.g., through a menu selection).

When configured in the Locate mode, the external charger 101 prompts the user to adjust the orientation of the external coil 102 to achieve an alignment (e.g., coaxial alignment) facilitating better coil interaction. The external charger 101 also provides feedback to the user indicating the current degree of alignment of the coils 102, 105. Examples of such feedback include audio signals, lit LED's, bar graphs or other textual, graphical, and/or auditory signals provided to the user.

In general, when the external charger 101 is configured in the Locate mode, the user sweeps the external coil 102 back and forth across the general location of the implanted neuroregulator 104. During the sweep, the external charger 101 sends a locator signal $S_1$ to the implanted coil 105 (see FIG. 7). The implanted coil 105 responds with a feedback signal $S_2$ (FIG. 7). The external charger 101 analyzes the feedback signal $S_2$ to determine the strength of the transmission link between the coils 102, 105.

In an embodiment, the external charger 101 keeps track of the strongest and weakest signals found during the sweep. The maximum signal strength and the minimum signal strength can be indicated to the user, e.g., via the visual display 172. These maximum and minimum values provide the user with context for judging the relative strength of a given signal at each location during the sweep. In an embodiment, the relative strength of the signal at a given position also can be displayed to the user as the user passes the external coil 102 over the position.

For example, in one embodiment, the first signal may be indicated initially as the maximum and minimum signal strength on the visual display 172. As the external coil 102 is moved about, any subsequent signals having greater signal strength replace the maximum signal shown. The strength of any subsequent, weaker signal also can be tracked by the external charger 101. The strength of the weakest signal can be indicated to the user as the minimum signal strength found. In one embodiment, if the strength of a subsequent signal falls between the currently established values for minimum and maximum, then an interpolated value representing the relative strength of the signal at the respective coil position can be displayed.

Thus the external charger 101 learns the maximum and minimum values for signal strength pertaining to external coil positions relative to the location of the implanted coil 105. By identifying the context of the signal strength measurements (i.e., the maximum and minimum signal strength found during a sweep), the external charger 101 can provide consistent and context-sensitive measurements of signal strength to the user regardless of the distance of the coil 102 from the implanted coil 105. Such measurements facilitate identification of an optimum coil position.

After the initial placement, the external coil 102 may need to be repositioned with respect to the implanted coil 105 to maintain the signal integrity. The external charger 101 can monitor whether the neuroregulator 104 is receiving signals having sufficient signal strength. If the external charger 101 determines the neuroregulator 104 is not receiving a sufficient signal, then the external charger 101 may sound an alarm (e.g., auditory and/or visual) to alert the user that coil transmission effectiveness has been lost.

In an embodiment, after indicating the loss of transmission effectiveness, the external charger 101 may invite the user to configure the external charger 101 into the Locate mode to reposition the external coil 102. Alternatively, the external charger 101 may invite the user to modify the position of the external coil 102 without entering the Locate mode. In an embodiment, when the coil transmission effectiveness is re-established, the system automatically self-corrects and resumes therapy delivery.

ii. Dynamic Signal Power Adjustment

The amount of power received at the neuroregulator 104 can vary due to relative movement of the coils 102, 105 after the initial placement of the external coil 102. For example, the signal strength may vary based on the distance between coils 102, 105, the lateral alignment of the coils 102, 105, and/or the parallel alignment of the coils 102, 105. In general, the greater the distance between the coils 102, 105, the weaker the transmission signal will be. In extreme cases, the strength of the transmission signal may decrease sufficiently to inhibit the ability of the neuroregulator 104 to provide therapy.

The coils 102, 105 may move relative to one another when the patient moves (e.g., walks, stretches, etc.) to perform everyday activities. Furthermore, even when the patient is inactive, the external coil 102 may be placed on tissue with substantial underlying fat layers. The surface contour of such tissue can vary in response to changes in patient posture (e.g., sitting, standing, or lying down). In the treatment of obesity, the distance from the top layer of skin 103 to the implanted coil 105 can vary from patient to patient. Moreover, the distance can be expected to vary with time as the patient progresses with anti-obesity therapy.

In addition, the power consumption needs of the neuroregulator 104 can change over time due to differences in activity. For example, the neuroregulator 104 will require less power to transmit data to the external charger 101 or to generate therapy signals than it will need to recharge the internal battery 151.

To overcome these and other difficulties, an embodiment of the external charger 101 can change the amplification level of the transmission signal (e.g., of power and/or data) to facilitate effective transmission at different distances between, and for different relative orientations of the coils 102, 105. If the level of power received from the external charger 101 varies, or if the power needs of the neuroregulator 104 change, then the neuroregulator sends a communication to the external charger 101 to adjust the power level of the transmitted signal dynamically to meet the desired target level for the implanted neuroregulator 104.

Adjustments to the power amplification level can be made either manually or automatically. In an embodiment, the neuroregulator 104 may determine a target strength of the transmission signal (e.g., a predetermined strength selected to provide sufficient power to the neuroregulator 104), assess the effectiveness of the transmission signals currently being sent to the implanted coil 105, and send a communication to the external charger to automatically adjust the amplification levels of the transmitted signals to enhance the effectiveness of the transmissions between the external coil 102 and the implanted coil 105.

For example, if the neuroregulator 104 indicates its battery 151 is ready for recharging 151, then the external charger 101 may establish a transmission link having a first power level appropriate for the task. At the conclusion of recharging, and when the neuroregulator 104 subsequently indicates it will begin therapy delivery, then the external charger 101 may change the power of the transmission link to a second power level sufficient to initiate therapy generation and delivery.

The neuroregulator may also communicate to the external charger 101 to increase the power level of the signal if the signal is lost due to separation and/or misalignment of the coils. If the external charger 101 is unable to sufficiently increase the power level of the transmitted signal, however, then the external charger 101 may issue an alarm and/or an invitation to the user to reposition the external coil 102 as described above.

The neuroregulator may also send a communication to the external charger 101 to decrease the strength of the signal (i.e., the amount of power) being sent to the neuroregulator 104. For example, due to safety concerns, the amount of power that can be transmitted across skin via RF signals is limited. Receiving excessive amounts of power could cause the neuroregulator 104 to heat up and potentially burn the patient.

In an embodiment, the neuroregulator 104 includes a temperature sensor (not shown) configured to monitor the temperature of the neuroregulator 104. The neuroregulator 104 can communicate the temperature to the external charger 101. Alternatively, the neuroregulator 104 can issue a warning to the external charger 101 if the neuroregulator 104 becomes too warm. When the temperature of the neuroregulator 104 is too high, the external charger 101 may lower the power transmitted to the implanted coil 105 of the neuroregulator 104 to bring the temperature down to an acceptable level or may stop charging. Alternatively, the neuroregulator 104 may detune its receiving RF input circuit 157 to reduce power and temperature.

In some cases, the maximum allowable temperature of the battery or PC board can be reached very quickly, thus truncating the charging procedure prematurely, the implanted neuroregulator battery then not achieving significant recharging. In an embodiment, the rate of rise of temperature is measured, and the charging current amplitude adjusted to achieve a lower rate of temperature rise, to allow charging to proceed without exceeding the temperature limit prematurely.

In embodiments, methods allow different implants that use different battery types (with different battery chemistries and/or voltage/charge capacities) and have different safety requirements with regard to maximum resulting temperature due to charging, to utilize a single device (an external charger) to safely and effectively charge their internal batteries. This is accomplished by having the charging control managed by the implanted device (e.g. neuroregulator), and the charge delivery managed by the external charger.

In embodiments, a system and method for recharging a battery in an implantable device involves control of the duration and power level of the charge energy by the implantable neuroregulator. In embodiments, the implantable neuroregulator obtains a baseline temperature of the implantable neuroregulator, typically about one hour or more after a previous charging session. The baseline temperature is typically around 37° C. The baseline temperature is used to determine a predetermined maximum safe temperature, for example, no more than 2° C. above the baseline temperature. The microprocessor of the implantable neuroregulator is configured to also measure a rate of temperature rise over a specific period of time, typically over a charging session. A charging session is usually at least about one hour but may be more or less depending on patient preference and status of the battery and temperature of the implantable component. In embodiments, the implantable component continuously monitors the temperature of the implant and the rate of rise of the temperature. If the temperature of the implantable device reaches certain defined limits, it sends a communication to the external charger to stop charging. In embodiments, those temperatures include a temperature about 2° C. or greater than the baseline temperature, a temperature of 45° C. indicating error, and a temperature of 16° C. indicating error. In other embodiments, the implantable neuroregulator communicates to the external charger to stop charging if the rate of rise of the temperature exceeds a predetermined unsafe rate, for example, 2° C. rise per hour or greater.

In embodiments, the implantable neuroregulator is configured to obtain information on the battery charge level, and the type of battery. The implantable neuroregulator is configured to store the battery charge curves for the type of battery employed in the implantable device. The implantable neuroregulator is configured to communicate to the external charger the power level for a charging session The power level in a typical case is selected based on the charging curve for the type of battery and for the time of charging session. If the battery charge level is below a predetermined level as defined by the battery manufacturer, for example 50% or less, the implantable neuroregulator will communicate to the external charger to start at a very low charging power level. In embodiments, the implantable device continuously monitors the power level of charging and sends a communication to the external charger to adjust the power level of the charging depending on the level of charge in the battery, the time of the charging session, and the temperature or rate of rise of the temperature. In embodiments, the external charger has at least 16 different power levels for charging.

In embodiments, charging the battery can use one of multiple (typically two) control loop algorithms:
1. Use a regulated (constant) charge rate chosen to allow unrestricted length of charge interval without exceeding a maximum safe temperature rise over a baseline temperature; or
2. Use an adaptive (variable throughout the charge session) charge rate that is chosen to maximize charge efficiency over a finite (fixed, but programmable) charge interval (typically 1 hour in length) without exceeding a maximum safe temperature rise over a baseline temperature.

The implantable neuroregulator is configured to select one or the other control loop algorithm. In embodiments, the implantable neuroregulator selects the regulated constant charge rate when the battery has a charge level as defined by the battery manufacturer, and the charging session used by the patient is typically one hour or less. In embodiments, the variable rate of charging is utilized when the charge level of the battery is at a lower predetermined level of the battery manufacturer requiring a low energy charging. The charging history of the patient can be used to determine if the patient is charging when the battery has been depleted to less than 50% and the time of a charging session. A default algorithm can be set at the factory or by the physician. In an embodiment, the default is the variable charge rate.

For the above, charge rate can be based on current or voltage delivered to the device battery. The "safe temperature rise" is programmable based on use case scenario, typically 2 degrees C. The baseline temperature is established by the implant prior to, or at the start of charge using temperature measurements of the environment made by the implant, restricted to a programmable maximum and/or minimum limit (typically 37 degrees C.).

The control algorithm in use is chosen and managed by the receiving implantable device. In some embodiments, the implantable device determines it's battery condition (charge level), and based on its charge level, battery chemistry, charge control algorithm, and programmed charging safety parameters (baseline temperature and max temp rise) the implantable device sends at least the following information to the external charger:
a) The implantable device will accept application of battery charge energy
b) The level of energy to send using a multiple level scale from a minimum level to a maximum level (typically 16 levels)
c) A duration of how long to apply the energy (typically in units of seconds).

In embodiments, charge energy is created and delivered to the receiving implantable device by the external charger under the following conditions:
1. The external charger will only deliver charge energy to the receiving implantable device if it indicates that it will accept application of battery charge energy.
2. The external charger will only deliver the level of energy requested by the receiving implantable device based on a multiple level scale from a minimum to a maximum level, programmed into the charger (typically 16 levels).
3. The external charger will only deliver charge energy for the duration of time requested by the implantable device (typically in units of milliseconds). It then stops and waits for another request from the receiving device.

Charging is managed through means of a "charging session" that is collaboration between the receiving device and the charging device. In embodiments, a charging session can begin when a user places the external charger in proximity to the implantable device and a charging session is requested by the implantable device. A charging session comprises a set of charging intervals, that continue until 1) the receiving implantable device no longer will accept application of battery charge energy, or 2) the external charger is moved out of proximity of the implantable device for a period of time (programmable, typically 5 minutes). If the external charger is moved back into proximity of the implantable device within the allowed period of time, the charging session is continued.

In other embodiments, the methods described above can be combined to facilitate recovery of some batteries with chemistries that are unsafe to be charged when their battery voltages drop below an established level.

Operational parameters, such as current, frequency, surface area, and duty cycle, also can be limited to ensure safe operation within the temperature limit. Further details regarding safety concerns pertaining to transdermal power transmission can be found, e.g., in The Cenelec European Standard, EN 45502-1 (August 1997), page 18, paragraph 17.1, the disclosure of which is hereby incorporated by reference herein.

In an embodiment, the external charger 101 also can decrease the target power level based on a "split threshold" power delivery concept. In such an embodiment, the external charger 101 initially provides a stronger signal than necessary to the neuroregulator 104 to ensure sufficient power is available. The external charger 101 then reduces the strength of the transmissions to a level just above the necessary signal strength when the actual requirements have been established. This subsequent reduction in power saves drain on the external battery 182 or power source 180.

For example, the external charger 101 can provide a low level of power capable of sustaining basic operation of the neuroregulator 104 when the neuroregulator 104 indicates it is not actively providing therapy or recharging its battery 151. When the neuroregulator 104 indicates it is about to initiate therapy, however, the external charger 101 can increase the power level of the transmission signal to a first threshold level, which is comfortably in excess of the power required to provide basic operation of the neuroregulator 104 as well as provide therapy. When the actual power requirements for therapy delivery become apparent, the external charger 101 may decrease the power level of the signal to a second threshold level, which is closer to the minimum power level required to provide basic functionality and maintain therapy delivery.

To perform this dynamic adjustment of signal strength, the external charger 101 analyzes a feedback signal (e.g., signal $S_2$ of FIG. 7) received from the implanted neuroregulator 104 indicating the amount of power required by the neuroregulator 104. The signal $S_2$ also may provide information to the external charger 101 indicating the power level of the signal $S_1$ being received by the implanted coil 105 of the neuroregulator 104. Such signal analysis would be within the skill of one of ordinary skill in the art (having the benefit of the teachings of the present invention). In an embodiment, the external charger 101 sets the signal power level based on a predetermined target power level for the transmission signal $S_1$. In response to the feedback signal $S_2$, the external charger 101 modifies the power level of the transmission signal $S_1$ to be within a tolerance range of the target power level. In an embodiment, the external charger 101 iteratively modifies the power level of the transmission signal $S_1$ until the feedback signal $S_2$ indicates the power level is within the tolerance range.

In addition to the dynamic adjustment of transmitted signal power described above, the neuroregulator 104 can be configured to optimize the power received from the external charger 101 when the neuroregulator 104 is recharging its battery 151. For example, the neuroregulator 104 may tune (e.g., using a combination of hardware and software) the natural resonant frequency of a recharging circuit (not shown) to maximize the power delivered to a load resistance for a given set of input parameters such as voltage, current and impedance at the implanted coil 105.

Transmission of power and/or information between the external charger 101 and the implanted neuroregulator 104 is typically performed using a carrier frequency of 6.78 MHz. Emission requirements of industrial, scientific and medical equipment are governed by Federal Communications Commission requirements described in FCC Title 47, Parts 15 and 18, and in EN 55011. The FCC requirements in the vicinity of this frequency are more restrictive than those of EN 55011.

A preferred method for managing the temperature and carrier frequency of the neuroregulator 104 during the recharging process includes passing a high power unmodulated transmission between the external charger 101 and the implantable neuroregulator 104 for a finite time (e.g., from about half of a minute to about five minutes), during which time no informational communication takes place between the external charger 101 and the implantable neuroregulator 104 (i.e., no information is passed between the charger 101 and the neuroregulator 104). At the conclusion of this finite time period, the unmodulated transmission ceases.

An informational, modulated communicational transmission then is passed at low power (e.g., within the requirements of FCC Title 47 Part 15) during which the temperature of the implantable neuroregulator 104 is communicated periodically to the external charger 101. If the temperature rises within certain restrictions (e.g., within the restrictions of The Cenelec European Standard, EN 45502-1 (August 1997), page 18, paragraph 17.1), then the communications transmission may be terminated, and the whole cycle may be repeated beginning with the initiation of the high power, unmodulated, recharging transmission.

In an additional preferred embodiment, when the informational, modulated communicational transmission is performed, the requisite signal power is reduced by using only externally transmitted power for the telemetered communications, and by simultaneously using internal battery power to operate the rest of the implanted circuitry 112 (FIGS. 3A and 3B), such as a microcontroller and/or peripherals. In such embodiments, the transmitted power may be less than if implant components (microcontroller and/or peripherals) also were receiving power from the RF transmission. Accordingly, the transmitted power may be limited to the power required for communications at short distances of six centimeters or less. Advantageously, such a power reduction reduces the total power required to below FCC Part 15 limits for telemetry communications.

During the phase in which the battery 151 of the implantable neuromodulator 104 is being recharged by a high powered, unmodulated transmission (e.g., under the requirements of FCC Title 47 Part 18), the temperature of the implanted neuroregulator 104 may be monitored and, if necessary, steps taken to inhibit the temperature from exceeding certain requirements (e.g., the requirements of *The Cenelec European Standard*, EN 45502-1 (August 1997), page 18, paragraph 17.1). For example, the temperature may be reduced by terminating the high powered, unmodulated transmission. In an alternative embodiment, the power level of the high powered, unmodulated transmission may be reduced in later cycles to limit the increase in temperature. In another embodiment, a control loop is established between the temperature rise and the power level of the unmodulated transmission to ensure the increase in temperature always remains within the identified requirements.

d. Implanted Leads

FIG. 9 shows an example distal end of a bipolar lead, such as lead 106 (see FIG. 1). The lead 106 includes a lead body 210 curved to receive a nerve (e.g., a vagus nerve). The lead body 210 contains an exposed tip electrode 212 configured to contact with the nerve received within the lead body 210. The tip electrode 212 is capable of delivering an electrical charge to nerves having a diameter ranging from about one millimeter to about four millimeters.

The lead body 210 also can have a suture tab 214 to attach the lead body 210 to the patient's anatomy to stabilize the position of the lead body 210. A first end of a flexible lead extension 216, which encloses a conductor from the electrode 212, couples with the lead body 210. A second, opposite end of the lead extension 216 terminates at a pin connector (not shown) for attachment to a connector (e.g., an IS-1 connector) 122 (shown in FIG. 1).

The lead 106 shown in FIG. 9 also includes a ring electrode 218 surrounding the lead extension 216 at a position spaced from the tip electrode 212. In an embodiment, the surface area of each electrode 212, 218 is greater than or equal to about thirteen square millimeters. A suture tab 220 may be provided for placement of the ring electrode 218 on the patient's anatomy in general proximity to the placement of the tip electrode 212 on the nerve.

In an alternative embodiment, a monopolar lead (not shown) may be implanted instead of the bipolar lead 106. Typically, the monopolar lead is the same as the bipolar lead 106, except the monopolar lead lacks a ring electrode 218. Such a monopolar lead is described in commonly assigned and co-pending U.S. patent application Ser. No. 11/205,962, to Foster et al, filed Aug. 17, 2005, the disclosure of which is hereby incorporated by reference.

Further details pertaining to example electrode placement and application of treatment can be found, e.g., in U.S. Pat. No. 4,979,511 to Terry, Jr., issued Dec. 25, 1990; U.S. Pat. No. 5,215,089 to Baker, Jr., issued Jun. 1, 1993; U.S. Pat. No. 5,251,634 to Weinberg, issued Oct. 12, 1993; U.S. Pat. No. 5,531,778 to Maschino et al., issued Jul. 2, 1996; and U.S. Pat.

No. 6,600,956 to Maschino et al., issued Jul. 29, 2003, the disclosures of which are hereby incorporated by reference herein.

2. Placement of Electrodes and Electrode Configuration Options

The electrodes can be placed on any number of nerves including, for example, of vagus nerve, renal artery, renal nerve, celiac plexus, a splanchnic nerve, cardiac sympathetic nerves, spinal nerves originating between T10 to L5, glossopharyngeal nerve, and tissue containing baroreceptors. For illustrative purposes, placement of the electrode is described with respect to the vagus nerve. FIG. 10 shows a posterior vagus nerve PVN and an anterior vagus nerve AVN extending along a length of a patient's esophagus E. The posterior nerve PVN and the anterior AVN are generally on diametrically opposite sides of the esophagus E just below the patient's diaphragm (not shown). A first tip electrode 212 of a lead arrangement 108 (FIG. 1) is placed on the anterior vagus nerve AVN. A second electrode 212a of the lead arrangement 108 is placed on the posterior vagus nerve PVN. The electrodes 212, 212a are connected by leads 106, 106a to a neuroregulator 104 (FIG. 1).

At the time of placement of the leads 106, 106a, it may be advantageous for the tip electrodes 212, 212a to be individually energized with a stimulation signal selected to impart a neural impulse to cause a detectable physiological response (e.g., the generation of antropyloric waves). The absence of a physiological response may indicate the absence of an overlying relation of the tested electrode 212, 212a to a vagus nerve PVN, AVN. Conversely, the presence of a physiological response may indicate an overlying relation (e.g., correct placement) of the tested electrode 212, 212a to a vagus nerve. After determining the leads 106, 106a create a physiologic response, the electrodes 212, 212a can be attached to the nerves PVN, AVN.

A preferred embodiment of the leads 106, 106a for treating obesity is shown in FIG. 10. The lead arrangement 108 includes bipolar leads 106, 106a. The bipolar leads 106, 106a each include one tip (i.e., or cathode) electrode 212, 212a that can be placed directly on the nerve PVN, AVN and one ring (i.e., or anode) electrode 218, 218a that is not placed on the nerve PVN, AVN, but rather may be attached to another structure (e.g., the stomach). In other embodiments, however, the lead arrangement 108 may include monopolar leads (i.e., each lead 106, 106a having only a tip electrode 212, 212a).

Electrical connection between the neuroregulator 104 and the therapy leads 106, 106a is made through bipolar IS-1 compatible lead adapters 122, 122a attached to the neuroregulator 104. If the bipolar lead design is used, two bipolar electrode pairs—one for the anterior vagus and one for the posterior vagus—are provided. One bipolar lead feeds a bipolar electrode pair. If the monopolar lead design is used, only the conductor connected to the distal tip electrode of each bipolar IS-1 connector is used.

The therapies as previously described could be employed by using blocking electrodes or stimulation electrodes or both in order to down-regulate and/or up-regulate the vagus nerve. A blocking signal down-regulates a level of vagal activity and simulates, at least partially, a reversible vagotomy.

Referring to FIGS. 11-18, the signals to the electrodes 212, 212a can be selected to create different types of signals and signal paths (referred to herein as "configurations"). FIGS. 11-18 illustrate four different electrode configurations.

a. Blocking Electrode Configuration (1)

A first blocking electrode configuration is shown in FIG. 11 and could be applied to any type of nerve as described herein. With respect to the vagus nerve, this configuration creates a current path (see arrow 1 in FIG. 11) with current flowing between the anterior and posterior nerves AVN, PVN. The tip electrodes 212, 212a, which are located directly on the anterior and posterior vagal nerves AVN, PVN, respectively, are electrically active. The anodic ring electrodes 218, 218a are not energized.

A continuous waveform (e.g., the square waveform $W_{10}$ shown in FIG. 12) propagates along the current path (see arrow 1) extending across the esophagus E. Such an electrode configuration is generally monopolar (i.e., only one location on each nerve PVN, AVN is subject to the treatment) and could be accomplished with monopolar leads (i.e., leads without ring electrodes 218, 218a).

b. Blocking Electrode Configuration (2)

Figure 13:
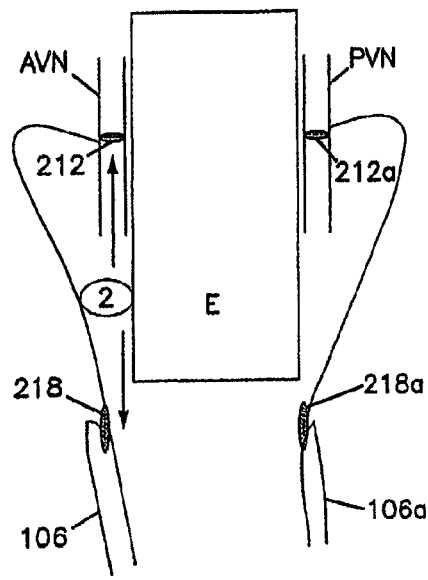
FIG. 13 is a schematic representation of a second electrode configuration according to aspects of the present disclosure.

FIG. 13 illustrates a second blocking electrode configuration in which each of the tip electrodes 212, 212a is associated with an anode electrode 218, 218a, respectively. With respect to the vagus nerve, therapy signals are applied only to the anterior vagus nerve AVN between the distal electrode 212 and the anode electrode 218. Advantageously, current (see arrow 2 in FIG. 13) does not flow through the esophagus E, thereby decreasing the likelihood of the patient sensing the treatment (e.g., feeling discomfort or pain).

In general, the anode electrodes 218, 218a can be positioned on any anatomical structure. In a preferred embodiment, the anode electrodes 218, 218a are placed on structures in generally close proximity (e.g., within about five centimeters) of the tip electrodes 212, 212a. For example, the anode electrodes 218, 218a can be placed on the same vagal nerve PVN, AVN as the anode electrode's associated electrode 212, 212a.

Figure 14:
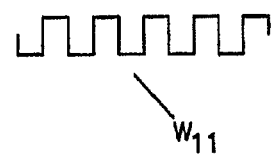
FIG. 14 is a schematic representation of a typical waveform according to aspects of the present disclosure.

In other embodiments, however, the anode electrodes 218, 218a can be placed on the stomach, the esophagus, or other anatomical structure in the general vicinity of the electrodes 212, 212a. In an embodiment, the anode electrodes 218, 218a can be placed on the stomach to permit monitoring of stomach contractions (e.g., by strain receptors associated with the anode electrodes 218, 218a). The arrangement of FIG. 13 results in a pacing waveform $W_{11}$ (FIG. 14).

c. Blocking Electrode Configuration (3)

Figure 15:
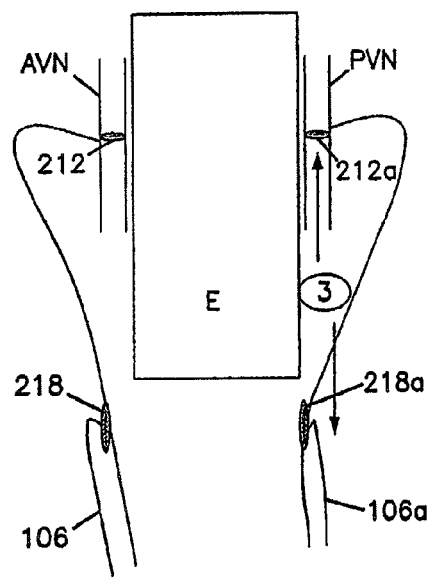
FIG. 15 is a schematic representation of a third electrode configuration according to aspects of the present disclosure.
Figure 16:
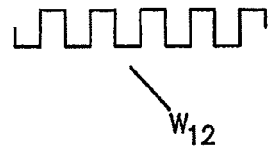
FIG. 16 is a schematic representation of a typical waveform according to aspects of the present disclosure.

FIG. 15 illustrates the same electrode configuration shown in FIG. 13, except the signals are applied only to the posterior vagus nerve PVN between the tip electrode 212a and the anode electrode 218a. The corresponding current path is shown by arrow 3 in FIG. 15. In an embodiment, the example signal waveform $W_{12}$ (see FIG. 16) propagating across the current path is the same as the waveform $W_{11}$ in FIG. 14. In other embodiments, however, any desired waveform can be utilized.

d. Blocking Electrode Configuration (4)

Figure 17:
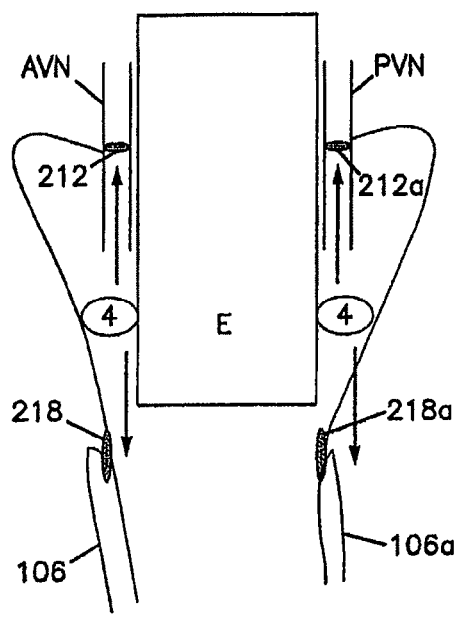
FIG. 17 is a schematic representation of a fourth electrode configuration according to aspects of the present disclosure.
Figure 18:
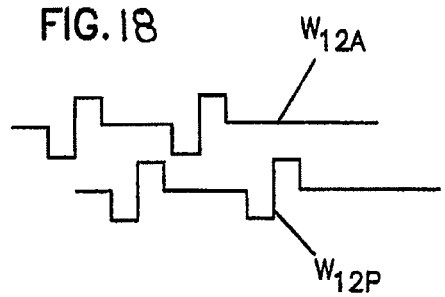
FIG. 18 is a schematic representation of a typical waveform according to aspects of the present disclosure.

The electrode configuration of FIG. 17 is generally the same as the electrode configurations of FIGS. 11, 13 and 15. In FIG. 17, however, an electrically active anode (e.g., ring electrode 218, 218a) and cathode (e.g., tip electrode 212, 212a) are associated with each nerve to provide a dual channel system. With respect to the vagus nerve, such an electrode arrangement routes current flow through both nerves PVN, AVN as indicated by arrows 4.

In an embodiment, a first electrode (e.g., the tip electrode 212, 212a) is placed directly on each of the nerve trunks and a second electrode (e.g., ring electrode 218, 218a) is located in proximity to the first electrode. Two waveforms (e.g., an anterior nerve waveform $W_{12A}$ and a posterior nerve waveform $W_{12P}$ shown in FIG. 18) are generated. In the example shown, the pulses of one of the waveforms occur during no-pulse periods of the other waveform. In such a configuration, a complete charging and rebalancing cycle can occur on one channel before the second channel is charged and rebalanced. Accordingly, only one channel is electrically paced at a time. Typically, the electrodes on the nerve are energized cathodically first.

3. Post-Operative Testing of Electrodes

After completing implantation, assembly, and positioning of the neuroregulator 104 and the electrode arrangement 108, a physician can determine the lead integrity by measuring the lead impedance and assessing whether the lead impedance is within an acceptable range. If the lead impedance is within range, the physician can connect an external computer 107 (e.g., a clinician computer) to the external charger 101 (see FIG. 1).

The clinician computer 107 can transmit treatment therapy settings and treatment data to the neuroregulator 104 via the external charger 101. The clinician computer 107 also can retrieve data from the external charger 101 or neuroregulator 104. For example, in one embodiment, the clinician computer 107 detects serial numbers of the external charger 101 and neuroregulator 104 automatically. After adjustment of blocking parameters and retrieval of data, the clinician computer 107 may be disconnected from the external charger 101.

After the patient has adequately recovered from the surgery (e.g., approximately fourteen days after the implantation surgery), the physician may program initial treatment parameters into the external charger 101. For example, the physician can couple the clinician computer 107 to the external charger 101 and follow menu commands on the computer 107 to upload select therapy programs to the external charger 101. In certain embodiments, the uploaded programs can then be transferred to the implanted neuroregulator 104.

Additionally, the physician can use the clinician computer 107 to select treatment start times for the patient. In an embodiment, treatment start times are selected based on the individual patient's anticipated waking and initial meal times. The start times can be set differently for each day of the week. Further details regarding scheduling treatment will be discussed herein with respect to FIG. 19.

4. System Software

The external charger 101 and the neuroregulator 104 contain software to permit use of the therapy system 100 in a variety of treatment schedules, operational modes, system monitoring and interfaces as will be described herein.

a. Treatment Schedule

To initiate the treatment regimen, the clinician downloads a treatment specification and a therapy schedule from an external computer 107 to the external charger 101. In general, the treatment specification indicates configuration values for the neuroregulator 104. For example, in the case of vagal nerve treatment for obesity, the treatment specification may define the amplitude, frequency, and pulse width for the electrical signals emitted by the implanted neuroregulator 104. In another embodiment, "ramp up" time (i.e., the time period during which the electrical signals builds up to a target amplitude) and "ramp down" time (i.e., the time period during which the signals decrease from the target amplitude to about zero) can be specified.

In general, the therapy schedule indicates an episode start time and an episode duration for at least one day of the week. An episode refers to the administration of therapy over a discrete period of time. Preferably, the clinician programs an episode start time and duration for each day of the week. In an embodiment, multiple episodes can be scheduled within a single day. Therapy also can be withheld for one or more days at the determination of the clinician.

During a therapy episode, the neuroregulator 104 completes one or more treatment cycles in which the neuroregulator 104 sequences between an "on" state and an "off" state. For the purposes of this disclosure, a treatment cycle includes a time period during which the neuroregulator 104 continuously emits treatment (i.e., the "on" state) and a time period during which the neuroregulator 104 does not emit treatment (i.e., the "off" state). Typically, each therapy episode includes multiple treatment cycles. The clinician can program the duration of each treatment cycle (e.g., via the clinician computer 107).

When configured in the "on" state, the neuroregulator 104 continuously applies treatment (e.g., emits an electrical signal). The neuroregulator 104 is cycled to an "off" state, in which no signal is emitted by the neuroregulator 104, at intermittent periods to mitigate the chances of triggering a compensatory mechanism by the body. For example, if a continuous signal is applied to a patient's nerve for a sufficient duration, the patient's digestive system eventually can learn to operate autonomously.

Figure 19:
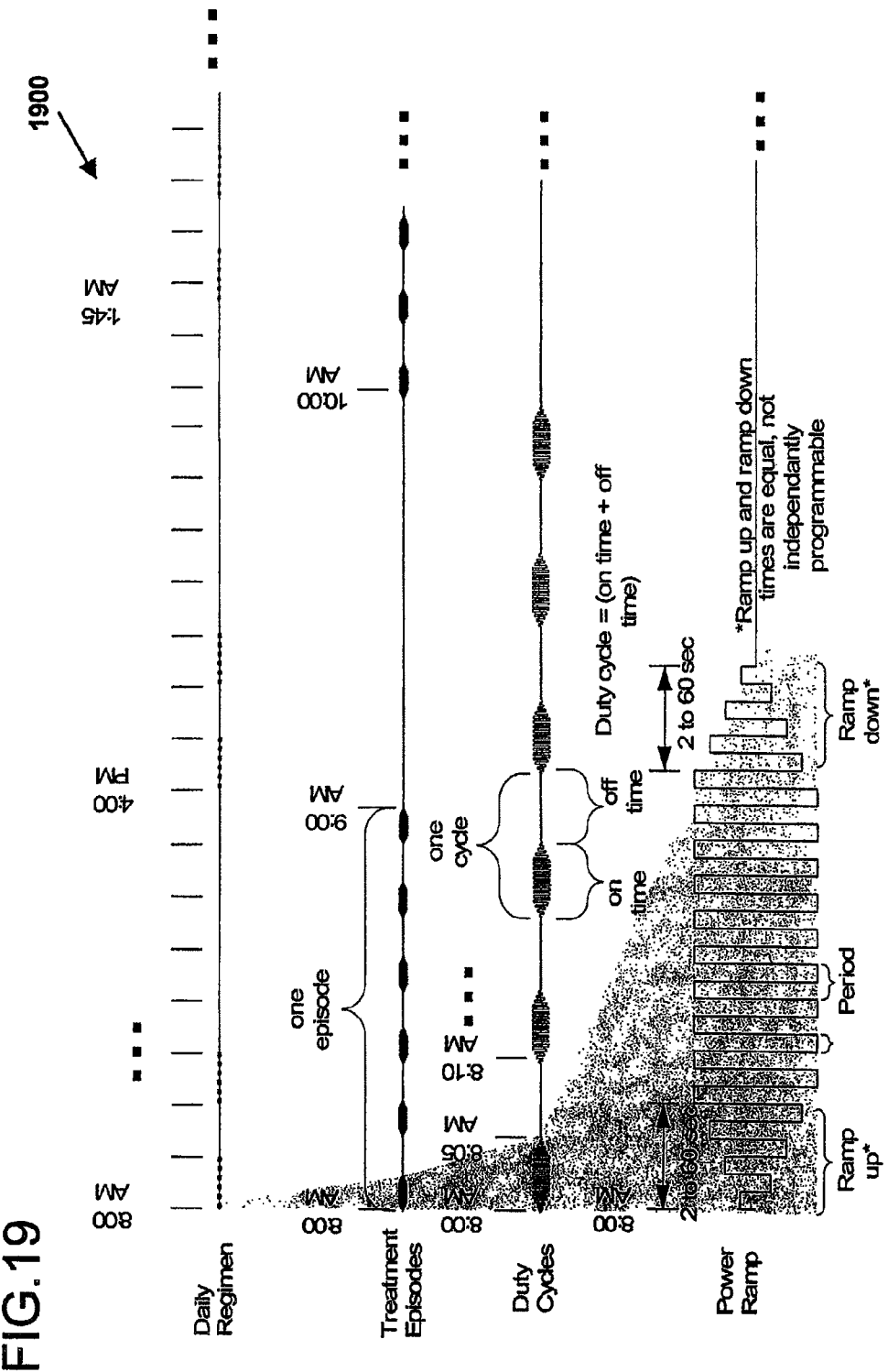
FIG. 19 is a graphical illustration of a treatment schedule according to aspects of the present disclosure.

An example daily treatment schedule 1900 is schematically shown in FIG. 19. The daily schedule 1900 includes a timeline indicating the times during the day when the treatment is scheduled to be applied to a patient. Duty cycle lines (dashed lines) extend along the time periods during which treatment is scheduled. For example, a first episode is scheduled between 8 AM and 9 AM. In certain embodiments, treatment schedules 1900 address other details as well. For example, the daily schedule 1900 of FIG. 19 indicates details of the waveform (e.g., ramp-up/ramp-down characteristics) and details of the treatment cycles.

b. System Operational Modes

The therapy system 100 can be configured into two basic operational modes—a training mode and a treatment mode—as will be described herein. In an embodiment, the therapy system 100 also can be configured into a placebo mode for use in clinical trials.

i. Training Mode

The training mode is used post-operatively to train the patient on using the therapy system 100. In this mode, electrical signals are not delivered to the nerves for the purpose of creating blocking action potentials. In a preferred embodiment, the neuroregulator 104 does not generate any electrical signals. In some embodiments, the training therapy setting can be preset by the therapy system manufacturer and are unavailable to the treating physician.

The training mode allows the physician to familiarize the patient with the positioning of the external charger 101 relative to the implanted neuroregulator 104. The physician also instructs the patient in how to respond to the feedback parameters within the therapy system 100. Training also can cover information and menus which can be displayed on the external charger 101, for example: the status of the battery 182 of the external charger 101, the status of the battery 151 of the implanted neuroregulator 104, coil position, lead/tissue impedances, and error conditions.

The physician also can train the patient in how to interact with the external charger 101. In an embodiment, the patient interacts with the external charger 101 using the selection input button 174. For example, by successively pressing the button 174, the patient can select one of multiple device operations, such as: device reset, selective interrogation of battery status, and coil position status.

ii. Treatment Mode

The treatment mode is the normal operating mode of the neuroregulator 104 in which the neuroregulator 104 applies a blocking signal to the nerves using blocking therapy settings. In general, the therapy settings are specified by the physician based on the specific needs of the patient and timing of the patient's meals. In some embodiments, the neuroregulator 104 controls the therapy being provided according to therapy programs and schedules stored on the neuroregulator 104. In other embodiments, the neuroregulator 104 follows the instructions of the external charger 101 to deliver therapy.

iii. Placebo or Maintenance Mode

This mode may be used for patients randomized to a placebo treatment in a randomized, double-blind clinical trial or for patients who have achieved their goals for electrical signal therapy. In this mode, the neuroregulator 104 does not apply therapy signals to the lead arrangement 108. Rather, in different embodiments, therapy signals can be supplied to a dummy resistor to drain the internal power source 151 (FIG. 3) of the neuroregulator 104.

The external charger 101 interacts with the patient and the physician as if therapy was being applied. For example, the patient and/or physician can view system status messages and a battery drain rate of the external charger 101 and neuroregulator 104. Because the external charger 101 functions as normal, the physician and the patient are blind to the fact that no significant therapy is being applied.

To give the patient the sensation that therapy is being applied, current pulses may be applied to the vagal nerve trunks during impedance measurements at the start of therapy. However, no therapy is delivered during the remainder of the blocking cycle. These sensations are felt by the patient and provide a misleading indication of activity. These sensations, therefore, help in maintaining the double blindness of the study.

In embodiments, a maintenance mode is one in which the neuroregulator delivers low energy electrical signals associated with safety checks and impedance checks for a period of time of 9 hours or less. In the interest of conserving battery power, the device may remain on but deliver the safety and impedance checks for 30 minutes to 9 hours, 1 hour to 8 hours, 1 hour to 7 hours, 1 hour to 6 hours, 1 hour to 5 hours, 1 hour to 4 hours, 1 hour to 3 hours and 1 hour to 2 hours. In embodiments, the safety checks are delivered at 50 Hz or less at least every 0.2 μs and impedance checks are delivered once every two minutes at a frequency of 1000 Hz or more. While not meant to limit the scope of the invention, it is believed that a therapeutic effect is associated with this low energy electrical single treatment if applied for at least 9 hours per day and not at shorter time periods. If the patient condition has stabilized or resolved, a health care provider may program the device for maintenance mode, leaving open the option to initiate a therapy program once again at a later date.

c. Treatment Therapy Settings

The neuroregulator 104 is configured to provide therapy signals to the electrode arrangement 108. In general, the therapy signals can induce stimulation of the nerves, blocking of nerve impulses, or some combination of the two.

i. Blocking Treatment

During treatment, the neuroregulator 104 provides blocking signals to the nerves of a patient. Blocking signals include high frequency waveforms that inhibit the transmission of signals along the nerves. In general, the physician selects and sets therapy settings (e.g., waveform characteristics and treatment schedule) based on meal times and a patient's eating pattern. In an embodiment, the therapy system 100 can provide a choice of at least three unique blocking therapy settings which can be applied as part of a daily treatment schedule.

ii. Low Frequency Mode

The low frequency mode provides low frequency stimulating signals along the patient's nerves to create a brief, potentially observable, physiological response as an intra-operative screen. Such a physiologic response could be, for example, the twitching of a muscle or organ, such as the stomach. Alternatively, for some nerve types, such as glossopharyngeal and/or baroreceptors a low frequency upregulating signal is utilized.

This therapy setting may be used by the physician to confirm correct electrode placement. The system operates in this mode for short time periods and, typically, only when the patient is under physician care. This mode may be accessed through the programmer interface. In an embodiment, this mode can be enabled/disabled (e.g., by the manufacturer) through the programming interface.

iii. Temporary Test Therapy Setting Mode

The therapy system 100 has the ability to program special treatment/testing therapy settings to support "one-time" physiological evaluations. Special testing therapy parameters can be preset (e.g., by the manufacturer) to be made available for use by the physician.

d. System Monitoring

In some embodiments, therapy system 100 facilitates monitoring the operation of the therapy system 100 and its components. By monitoring the operation of the therapy system 100, faults and malfunctions can be caught early and dealt with before becoming problematic. The therapy system 100 can record the operation and/or the fault conditions for later analysis. The therapy system 100 also can notify the patient and/or physician of the system operating status and non-compliant conditions. For example, an error message can be displayed on screen 172 (see FIG. 5) of the external charger 101 or on a display screen (not shown) of the external computing device 107 (see FIG. 1).

Embodiments of the therapy system 100 can confirm proper functioning of and communication between the components of the therapy system 100. For example, the therapy system 100 can monitor the link strength between the external charger 101 and the neuroregulator 104. In an embodiment, immediate feedback indicating the link strength can be provided to the patient (e.g., through the display 172 of the external charger 101) and/or to the physician (e.g., through the external computing device 107).

The therapy system 100 also can determine one or both of the coils 102, 105 are broken, shorted, or disconnected. In an embodiment, the therapy system 100 determines whether the coils 102, 105 are operational by measuring the impedance between the coils and determining whether the measured impedance falls within an acceptable range.

The therapy system 100 also can measure the impedance between the electrodes 212, 212a of the lead arrangement 108 and determine whether the impedance is out of range (e.g., due to inadequate electrode-nerve contact, or shorted electrodes). Details regarding the measurement of lead impedance are discussed later herein. Impedance measurements also can be used to verify proper lead placement, verify nerve capture, and monitor stomach contraction during the implant procedure.

The therapy system 100 also can communicate other types of system errors, component failures, and software malfunctions to the patient and/or physician. For example, the therapy system 100 can monitor the battery status (e.g., low battery, no charge, battery disconnected, etc.) of the neuroregulator 104 and/or the external charger 101 and warn the patient and/or physician when the battery should be recharged and/or replaced.

The therapy system 100 can indicate an inability to deliver a signal having the specified current (e.g., due to the impedance being out of range or due to internal component failure) to the lead arrangement 108 during treatment delivery. The therapy system 100 also can indicate whether the external charger 101 and/or the neuroregulator 104 have sufficient power to transmit and/or receive signals (e.g., based on antenna alignment, battery power, etc.).

i. Lead Impedance Measurement

Embodiments of the therapy system 100 have the ability to independently measure and record lead impedance values. Lead impedance values outside a predefined range may indicate problems or malfunctions within the therapy system 100. High impedance, for example, could mean that the electrodes 212, 212a are not properly coupled to the nerves of the patient. Low impedance could mean inappropriate shorting of the electrodes 212, 212a.

These embodiments of the therapy system 100 allow the physician to measure lead impedance on-demand. The therapy system 100 also can enable the physician to periodically measure impedance (e.g., during the Training Mode) without initiating a blocking therapy setting. Generally, impedance is measured and stored separately for each channel of each electrode configuration. These measurements may be used to establish a nominal impedance value for each patient by calculating a moving average. The nominal impedance and impedance tolerance range can be used for system non-compliance monitoring, as will be described below.

ii. Device Safety Check a. H Bridge Safety Check

As explained above, where a therapy system 100 including an electrical circuit is utilized to apply an electrical stimulus to a patient, it is desirable to implement safety checks to ensure proper operation of electrical stimulators. Specifically, it is important to protect damage to patient nerves, muscles, tissue, and the like through methods and systems intended to increase safer application of various stimulation therapies.

Embodiments of the present disclosure can be designed to perform safety checks within medical devices, both prior to operation and periodically during operation. The safety checks disclosed herein provide continued, safe operation of such devices. In the following paragraphs, reference is made to the accompanying drawings that form a part hereof, and in which it is shown by way of illustration, specific embodiments in which the invention may be practiced. It is to be understood that other embodiments may be utilized and structural changes may be made without departing from the scope of the present invention. Such safety checks represent checks that can be performed relative to circuitry included within the system, as well as relating to the electrical signal delivered to the patient.

In an embodiment, a safety check of the functioning of an H bridge circuit is performed periodically but not while therapy is being delivered. In embodiments, during a therapy cycle, the therapy is stopped for a time interval and the function of the H bridge is checked and then therapy is resumed in a therapy cycle. In embodiments, that interval is about once every 4 seconds. In embodiments, the function of the H bridge is checked to determine if it is functioning to supply current when needed and functioning to turn off current (e.g. that none of the switches are stuck on). In embodiments, if any of the switches indicate that they are not functioning, the microprocessor terminates therapy.

Figure 25:
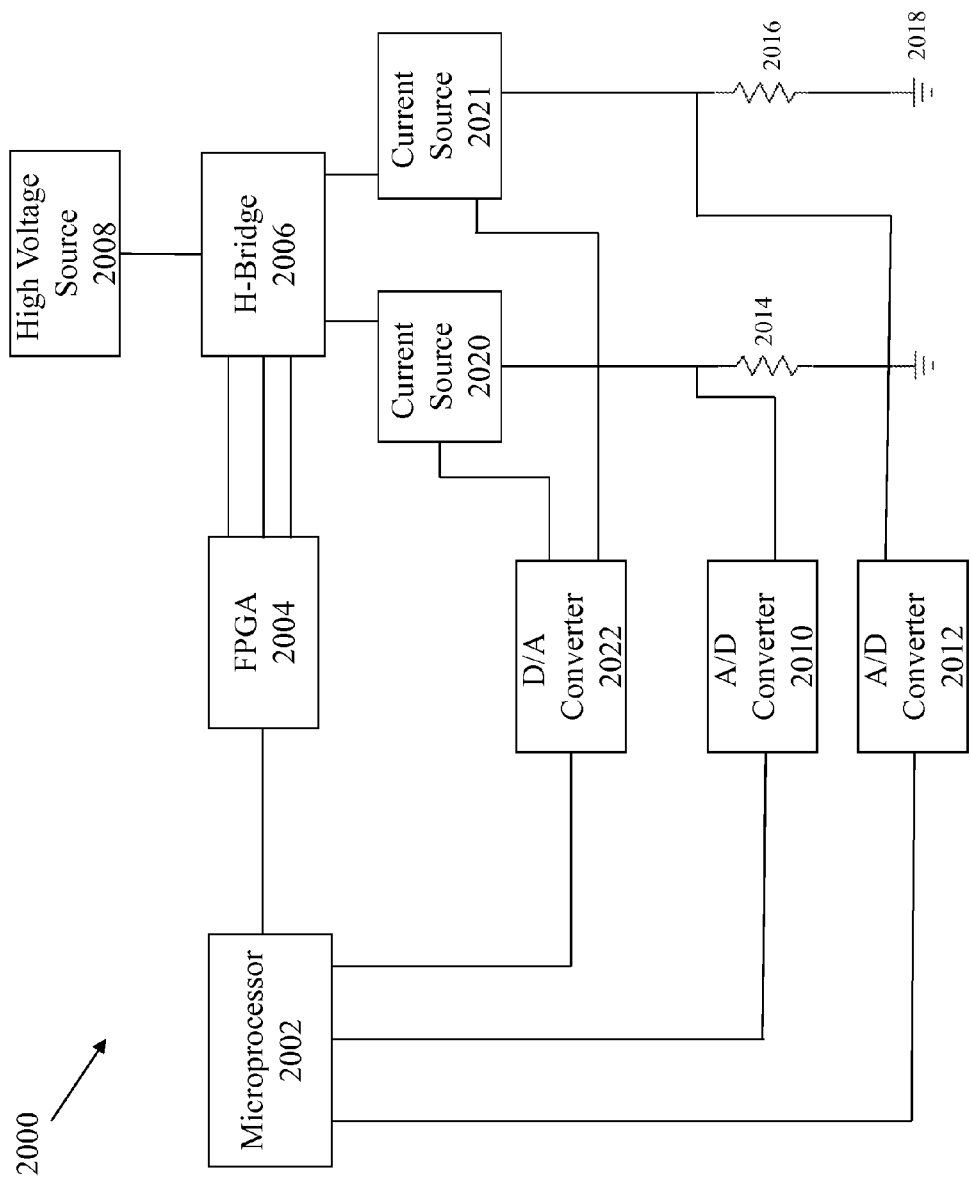
FIG. 25 is a schematic representation of a medical device configured to apply an electrical stimulus to a patient having an H-bridge circuit according to an embodiment of the present disclosure.

FIG. 25 is a schematic representation of a medical device 2000 which is configured to apply an electrical stimulus to nerves, tissue, muscle, or the like, of a patient. The medical device 2000 can be configured to deliver any of the therapies discussed above. In some embodiments, the medical device 2000 represents a portion of the therapy system 100 illustrated and described above (i.e., a portion of that therapy system delivering an electrical signal to a patient).

In the embodiment shown, a microprocessor 2002 is communicatively connected to an H-bridge circuit 2006 via a field-programmable gate array ("FPGA") 2004. The microprocessor 2002 can be, for example, electrically coupled to the FPGA 2004, which is in turn electrically connected to the H-bridge circuit 2006. The microprocessor 2002 is also directly connected to the H-bridge circuit 2006 by way of analog-to-digital converters ("ADCs") 2010, 2012 and one or more digital to analog converters 2022. The A/D convertors can have single or multiple channels, for example, two A/D convertors are shown here but other configurations may be utilized depending on the number of channels in each A/D convertor. The H-Bridge circuit is connected to current sources 2020 and 2021. The D/A Converter 2022 is controlled by the microprocessor 2002, and provides voltage signals to the current sources 2020 and 2021 to establish the current flowing through 2020 and 2021. A D/A convertor can be a single unit or can be multiple D/A units, for example, a single unit with 4 different channels can be utilized or 4 different single channel D/A convertors can be utilized. The purpose of the A/D converters 2010 and 2012 is to measure the voltage at the top of the current sense resistors and verify that the programmed current is correct. The microprocessor 2002 is configured to monitor and control the activity of the H-bridge circuit 2006. Specifically, the microprocessor 2002 is configured to send and receive signals for directing and monitoring activity in the H-bridge circuit 2006, including delivering a therapy, as well as directing and monitoring tests of the circuit. An example therapy to be delivered via the lead arrangement 108, via the H-bridge circuit 2006 is discussed in further detail herein.

In some embodiments, the microprocessor is electrically coupled to each H-bridge circuit through an analog-to-digital converter and a digital-to-analog converter, wherein: the first digital-to-analog converter is electrically connected to a first current source located between the first H-bridge circuit and the first sensing resistor and a second digital-to-analog converter is electrically connected to a second current source located between the second H-bridge circuit and the second sensing resistor; the first analog-to-digital converter is electrically connected to the first current sensing resistor; the second analog-to-digital converter is electrically connected to the second current sensing resistor and wherein the first digital-to-analog converter and the second digital-to-analog converters receive signals from the microprocessor to control the first and second current sources and the first analog-to-digital converter and the second analog-to-digital converter send signals to the microprocessor indicative of voltage drops across each of the first and second sensing resistors.

In some embodiments, microprocessor 2002 corresponds to CPU 154 of FIGS. 3A-3B; in such embodiments, the microprocessor 2002 can execute instructions stored in the memory 152 for monitoring and managing signal levels at the lead arrangement 108.

In some embodiments, the H-bridge circuit 2006 provides an interface to electrodes, such as the lead arrangement 108. The H-bridge circuit 2006 provides a structure by which various signals can be delivered to a vagus nerve of a patient. Specifically, the H-bridge circuit 2006 controls the amount of electrical stimulation applied at the electrodes by controlling the output voltage (i.e., potential difference) between those electrodes. To do this, the H-bridge circuit 2006 controls the flow of electricity though one or both of the lead(s) by selectively activating and deactivating electrical switches (not shown) in the H-bridge circuit 2006, so that the output voltage between the lead(s), or across contacts of a particular lead, maintain a waveform-shape. For example, the H-bridge circuit 2006 can correspond to or be included in the output module 161 of FIGS. 3A-3B.

In one possible embodiment, the H-bridge circuit 2006 includes dual H-bridge circuits (See FIG. 26), each separately coupled to the high voltage source 2008. Additional details of the H-bridge circuit 2006 are discussed below.

In the embodiment shown, a high voltage source 2008 is electrically coupled to the H-bridge circuit 2006 to drive the device 2000. The high voltage source 2008 can be, in various embodiments, an adjustable voltage source configured to deliver a desired voltage (and associated current) for use in delivering a therapy to a patient, for example through use in connection with the H-bridge circuit 2006. In some embodiments, the high voltage source 2008 is programmable or otherwise adjustable by the microprocessor and/or FPGA. For example, in some embodiments, the high voltage source 2008 corresponds to the power source 161 and associated charge control module 153, and power regulator modules 156, 160, of FIGS. 3A-3B, such that the high voltage source 2008 receives feedback from the processor 2002 (e.g., the CPU 154), and delivers an adjustable signal to the H-bridge circuit 2006 (e.g., the output module 161). In some embodiments, the high voltage source includes a 12 volt battery and associated circuitry useable to control and/or adjust output voltage; in alternative embodiments, other voltage levels or types of voltage sources could be used.

Due to the sensitive nature of therapy delivery using the device 2000, the device can be configured to perform tests to ensure safe operation of the H-bridge circuit 2006 and associated electrodes, as well as many other features of the device 2000. For example, in some instances, the switches in the H-bridge circuit 2006 may fail to activate or deactivate as required, thereby creating one or more types of malfunction effects. For example, a DC offset could be generated, which can adversely affect the electrical stimulation applied to the patient. In certain instances, moderate to severe damage to a patient's nerves, tissue, muscle, or the like may occur as a result of such DC offset. To ensure that the switches are activating and deactivating as intended, the device 2000 periodically performs an H-bridge safety check prior to and during therapy of a patient, details of which are discussed below.

In some embodiments, the microprocessor 2002 is configured to periodically perform a sequence of tests on the H-bridge circuit 2006 during operation of the device 2000 to ensure proper operation of the H-bridge circuit 2006 but not while therapy is being delivered to the patient. In one embodiment, the sequence of tests occurs once every four seconds; in alternative embodiments, the microprocessor 2002 can be programmed to perform H-bridge tests at various times, such as prior to delivery of a therapy, every 30 seconds, or upon receiving a signal from remote from the device 2000 (e.g., from a remote system, or based on an interrupt from the FPGA 2004). In alternative embodiments, testing time intervals may vary depending on the circumstances surrounding use of the medical device.

According to some embodiments the microprocessor 2002 is configured to receive signals indicative of a voltage drop across each of a first sensing resistor 2014 and a second sensing resistor 2016 (FIG. 25). Both sensing resistors 2014, 2016 are electrically connected between the H-bridge circuit 2006 and a ground 2018. Further, the microprocessor 2002 is configured to generate signals indicative of current flow through each of the sensing resistors 2014, 2016. Upon generation of signals indicating current flow above or below a predetermined threshold current (or otherwise outside of an expected threshold current), the microprocessor 2002 aborts use of the device 2000. The microprocessor 2002 may accomplish sending and receiving of signals either independently or through the interconnectivity of the ADCs 2010, 2012.

In embodiments, receiving signals further comprise receiving a signal from an analog-to-digital converter; the analog-to-digital converter is electrically connected between the sensing resistor and the ground; and wherein, the digital-to-analog converter and the analog-to-digital converter are electrically connected between the H-bridge circuit and the microprocessor. In embodiments, the microprocessor sends a signal to the one or more digital to analog converters to control the current source.

In some embodiments, the FPGA 2004 is configured to drive control inputs provided to the H-bridge circuit 2006, and accordingly to manage delivery of voltage to the lead arrangement 108. As such, in some embodiments the FPGA 2004 can perform one or more functions described above as associated with the signal generation module 159 (FIG. 3B). Specifically, the FPGA 2004 is configured to receive the signals sent by the microprocessor 2002, indicating a particular state of the H-bridge 2006 (e.g., as determined from a current detected through each of the sensing resistors 2014, 2016), and a current state or signal to deliver to the H-bridge. In response to the signals, the FPGA 2004 generates a set of control outputs that are connected to various switches in the H-bridge 2006 (as illustrated, for example, in FIG. 26) that control the current flow from the high voltage source 2008 and through the H-bridge circuit 2006. Further, the FPGA 2004 may be configured to, in connection with the microprocessor 2002, drive H-bridge inputs to perform intermittent testing of the H-bridge circuit 2006 through a sequence of tests. Based upon these tests, the microprocessor may abort use of the device 2000 if the tests indicate current flow above or below a predetermined threshold current.

Figure 26:
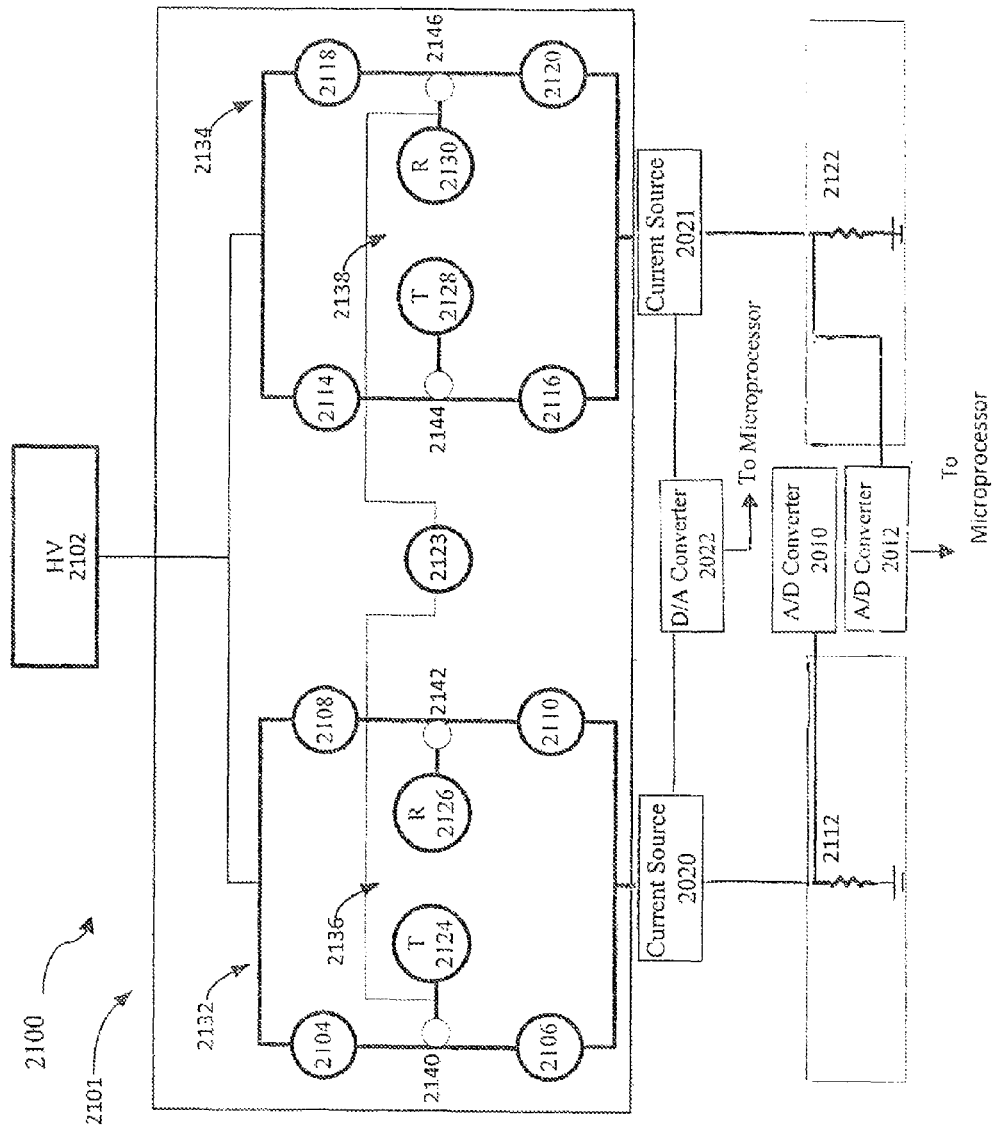
FIG. 26 is a schematic representation of dual H-bridge circuits providing electrical connection to the pacing electrodes of FIGS. 10-17.

Referring now to FIG. 26, a schematic representation is shown of one embodiment of a system 2100 including H-bridge circuitry 2101. The H-bridge circuitry 2101 includes a first H-bridge circuit 2132 and a second H-bridge circuit 2134, which are electrically coupled to a high voltage source 2102. More specifically, circuitry 2101 is one embodiment of the H-bridge circuit 2106 of the device 2000 illustrated in FIG. 25; analogously, high voltage source 2102 is an example embodiment of the high voltage source 2008 of FIG. 25, and as such, an embodiment of the power source 151, charge control module 153, and power regulator modules 156, 160 of FIGS. 3A-3B. As in FIG. 25, the H-Bridge circuit is connected to current sources 2020 and 2021. The D/A Converter 2022 is controlled by the microprocessor 2002, and provides voltage signals to the current sources 2020 and 2021 to establish the current flowing through 2020 and 2021. Additionally, the first H-bridge circuit 2132 and second H-bridge circuit 2134 are electrically connected to a ground by sensing resistors 2112, 2122, analogously to resistors 2014, 2016 of FIG. 25.

As shown in system 2100, dual H-bridge circuits 2132, 2134 are illustrated which include first and second electrical leads 2136, 2138. Each H-bridge circuit 2132, 2134 includes connections to the high voltage source 2102, sensing resistors 2112, 2122, and two pairs of series electrical switches connected in parallel between the voltage supply connections and sensing resistors 2112, 2122. In certain embodiments, the leads 2136, 2138 are connected to tissues, muscles, nerves, or the like of a patient and are utilized to apply an electrical stimulation thereupon. The H-bridge circuits 2132, 2134 control flow of electricity to the leads 2136, 2138 by reversing the flow of electricity through the leads 2136, 2138, thereby, creating a steady waveform-shaped output voltage between the leads 2136, 2138.

More specifically, the first electrical lead 2136 forms a first electrode, and includes a first tip connection 2124 and a first ring connection 2126. The second electrical lead 2138 forms a second electrode, and includes a second tip connection 2128 and a second ring connection 2130. In embodiments, at least one of the first and second tip and ring connections include a pad and hook shaped arrangement. Such tip and ring connections can, in some embodiments, correspond to the anterior and posterior tip and ring connections described above in connection with FIGS. 10-17. In certain embodiments of the present invention, the first lead 2136 is an anterior lead and the second lead 2138 is a posterior lead. Thus, the first lead 2136 is connected to the anterior trunk of the patient's vagal nerve, while the second lead 2138 is connected to the posterior trunk of the patient's vagal nerve. In alternative embodiments, this arrangement may be reversed such that the first lead is a posterior lead and the second lead is an anterior lead.

To ensure appropriate electrical stimulation, the first H-bridge circuit 2132 controls electrical flow of the first lead 2136, and the second H-bridge circuit 2134 controls electrical flow of the second lead 2138. In particular, each of the tip and ring connections 2124-2130 can be tied either to a high voltage or to ground by activating a switch to electrically connect the respective tip and/or ring to the high voltage source 2102 or to a ground. In particular, the first tip connection 2124 is tied to the high voltage source 2102 by a first switch 2104 and to ground by a second switch 2106. The first ring connection 2126 is tied to the high voltage source 2102 by a third switch 2108 and to ground by a fourth switch 2110. Similarly, the second tip connection 2128 is tied to the high voltage source 2102 by a fifth switch 2114 and to ground by a sixth switch 2116. The second ring connection 2130 is tied to the high voltage source 2102 by a seventh switch 2118 and to ground by a eighth switch 2120.

In general, in this embodiment, differential signals can be applied from the first tip connection 2124 to the first ring connection 2126, and from the second tip connection 2128 to the second ring connection 2130. As such, signals are applied at local areas, the exact location depending upon placement of the first and/or second electrodes. In some embodiments, a ninth switch 2123 connects across the H-bridge circuits 2132, 2134, for example from the first tip connection 2124 to the second ring connection 2130, or otherwise across the circuits. The ninth switch 2123 allows a further control input to activate a differential tip-to-tip or ring-to-ring activation configuration, allowing for activation of only a portion of the overall circuitry, as described in some of the configurations described above. In various embodiments, the electrical switches 2104, 2106, 2108, 2110, 2114, 2116, 2118, 2120, 2123 may be transistors, such as, a field-effect transistor, bipolar junction transistor, or any other similarly functioning electrical switch.

During the course of controlling the electrical flow to the leads 2136, 2138, one or more of electrical switches 2104, 2106, 2108, 2110, 2114, 2116, 2118, 2120, 2123 may fail to activate or deactivate, thereby creating a potential DC offset which could damage the patient's nerve, muscle, tissue, or the like. In an effort to protect against potential DC offset difficulties, the device 2000 performs periodic safety checks on the H-bridge circuits 2132, 2134. During each test, the device 2000 monitors a current flow through the sensing resistors 2112, 2122, wherein the current flow indicates that various switches are operational within the H-bridge circuits 2132, 2134. More specifically, the H-bridge safety check is performed by individually turning on each vertical leg and each horizontal leg of the H-bridge circuits 2132, 2134 and determining current flow through the sensing resistors 2112, 2122, for example by receiving at the microprocessor 2002 a voltage reading (via A/D converters 2010, 2012, on either side of each resistor.

For example, in one embodiment of the testing sequence, the first and second switches 2104, 2106 are activated. At this point, the current flow through the sensing resistor 2112 is determined. Because activation of switches 2104, 2106 closes a circuit between the high voltage source 2102 and the sensing resistor 2112, the voltage drop over the resistor will be nearly a full voltage drop from the high voltage source 2102 to ground, and the current will equivalently be high. Next, the first and second switches 2104, 2106 are deactivated, and the third and fourth switches 2108, 2110 are activated. Again, the current flow through the sensing resistor 2112 is measured, and the same result is expected. Thereafter, the third and fourth switches 2108, 2110 are deactivated, and the fifth and sixth switches 2114, 2116 are activated and the current flow through the sensing resistor 2122 is determined. Finally, the fifth and sixth switches 2114, 2116 are deactivated, and the seventh and eighth switches 2118, 2120 are activated. Once again, the current flow through the sensing resistor 2122 is measured. At this point, the seventh and eighth switches 2118, 2120 are deactivated. If the current flow measurements are outside an expected current flow range at any time during the testing sequence, this indicates that one or more of the switches cannot activate, and therefore a connection between the voltages source 2102 and the ground may fail (resulting in a lower than expected current across one of the resistors 2112, 2122). In this case, the device 2000 (and in particular the microprocessor 202) alarms an error and therapy is aborted.

In another embodiment of the testing sequence, the above series of tests is followed by a second series of tests. Specifically, the first and third switches 2104, 2108 are activated, with switches 2106, 2110 maintained as deactivated. Next, the current flow through sensing resistor 2112 is determined. In this case, minimal current flow through the resistor 2112 is expected, because no direct path to voltage source 2102 should be available. Then, the first and third switches 2104, 2108 are deactivated, and the second and fourth switches 2106, 2110 are activated. Again, the current flow through the sensing resistor 2112 is measured. Next, the second and fourth switches 2106, 2110 are deactivated, and the fifth and seventh switches 2114, 2118 are activated. The current flow through the sensing resistor 2122 is then determined. Finally, the fifth and seventh switches 2114, 2118 are deactivated, and the sixth and eighth switches 2116, 2120 are activated. Next, the current through the sensing resistor 2122 is calculated. Again, if the current flow measurements are outside an expected current flow range (in this case, unexpectedly high) at any time during the testing sequences, the device 2000, and in particular the microprocessor 2002, alarms and therapy is aborted. In yet another embodiment, the second series of tests is not preceded by the first series of tests.

b. Voltage Output Safety Check

In another embodiment, a medical device comprises a first electrical lead comprising a first tip connection and a first ring connection; a second electrical lead comprising a second tip connection and a second ring connection; and an impedance measurement device configured to monitor an output voltage applied to the nerve to detect a direct current offset. In embodiments, the use of the medical device is halted if a direct current is detected. In embodiments, the impedance measurement device is configured to monitor the output voltage for symmetry between positive and negative voltages applied to the nerve. In other embodiments, the impedance measurement device monitors a cumulative additive effect of the output voltage over a predetermined period.

In some embodiments, the impedance measurement device includes a programmable circuit electrically connected to the first and second electrical leads and configured to execute program instructions, which, when executed, cause the impedance measurement device to detect a first positive voltage peak applied across electrical connections of one or both first and second electrical leads; to detect a first negative voltage peak applied across electrical connections of one or both first and second electrical leads; compare the first positive voltage peak and the first negative voltage peak to determine at least a portion of an impedance; and upon detecting that the impedance is outside a predetermined range, generate an alarm indicating the presence of a direct current signal applied to the nerve. In some cases, the first positive voltage peak and the first negative voltage peak are applied across the first tip connection and the second tip connection.

In yet other embodiments, the programmable circuit is further configured to cause the impedance measurement device to detect a second positive voltage peak applied across electrical connections of one or both first and second electrical leads; to detect a second negative voltage peak applied across electrical connections of one or both first and second electrical leads; compare the second positive voltage peak and the second negative voltage peak to determine at least a portion of an impedance; and upon detecting that the impedance is outside a predetermined range, generate an alarm indicating the presence of a direct current signal applied to the nerve.

In some embodiments, the system 2100 also includes capacitive dividers 2140, 2142, 2144, 2146. In the current embodiment, the capacitive dividers 2140, 2142, 2144, 2146 are positioned on each ring and tip connection of the H-bridge circuits, and are used by the device as a part of an impedance measurement device useable to calculate portions of the impedance of the circuitry.

An example of such a capacitive divider circuit is illustrated in FIG. 26, described in further detail below. The capacitive dividers 2140, 2142, 2144, and 2146 are configured to monitor an output voltage between various connections of the H-bridge circuits to determine a portion of an impedance between those connections. For example, in one embodiment, the capacitive dividers 2140, 2142 monitor an output voltage between the first tip connection 2124 and the first ring connection 2126. In an alternative embodiment, the capacitive dividers 2140, 2144 monitor an output voltage between the first tip connection 2124 and the second tip connection 2128 and/or the first ring connection 2126 and the second ring connection 2130. Varying combinations of capacitive dividers 2140, 2142, 2144, 2146 may be used depending on which of the connections 2124, 2126, 2128, 2130 are being used by the device to apply an electrical stimulus. If the determined impedance is outside a predetermined range, the device generates an alarm indicating the presence of a direct current signal applied to the patient.

In still some further embodiments, additional tests can be performed using different combinations of switches, including switch 2123, useable for alternative tip-to-tip configurations. Various testing arrangements relative to the H-bridge are discussed below in connection with FIG. 29.

Figure 27:
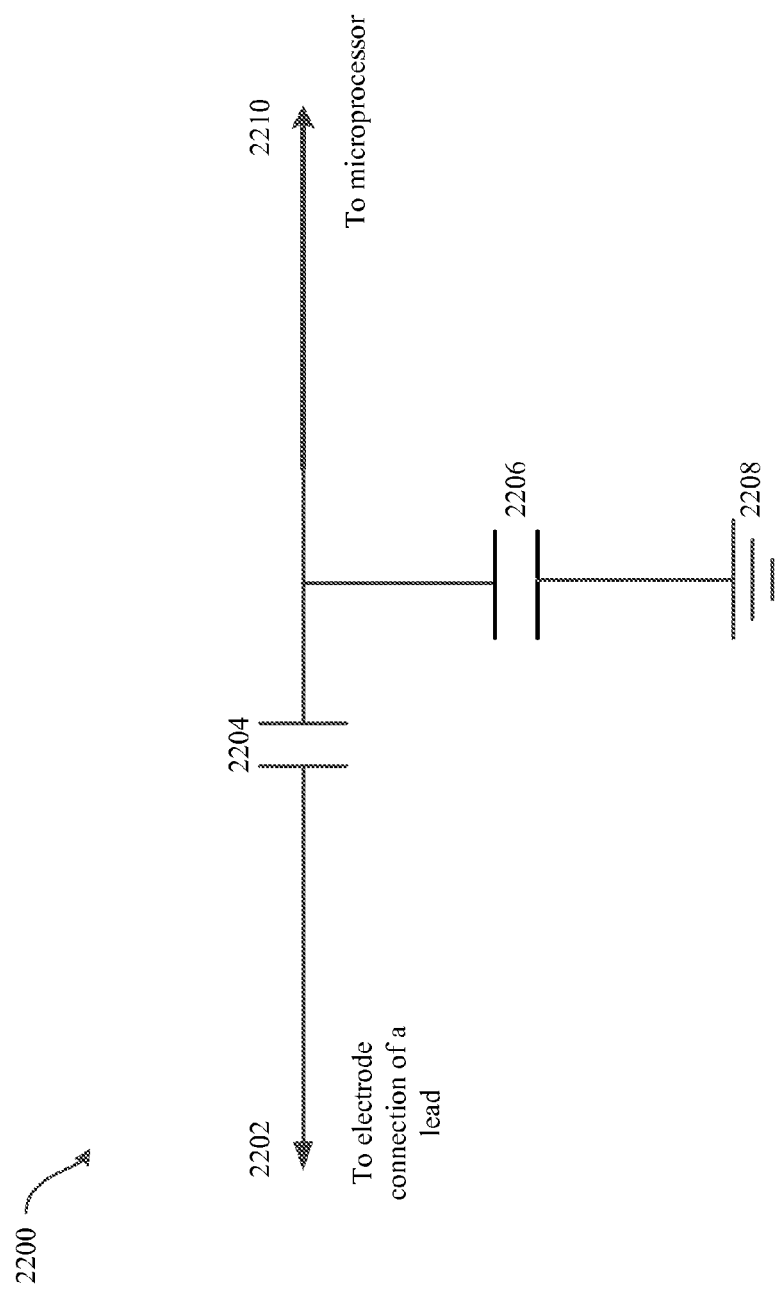
FIG. 27 is a schematic diagram of a capacitive divider of an impedance measurement device.

Now referring to FIG. 27, a schematic diagram of a capacitive divider 2200 is illustrated, according to an example embodiment of the present disclosure. The capacitive divider 2200 is useable within an overall device, such as those described herein, as an embodiment of the capacitive dividers 2140, 2142, 2144, 2146 of FIG. 26, and can represent the capacitive divider module 162 of FIGS. 3A-3B. The capacitive divider 2200 can be used, for example, to allow a microprocessor to monitor a state of a particular electrode connection at one of the leads of an implantable medical device, without directing current onto the lead. This can be used, for example, to calibrate the electrodes to ensure consistent voltage levels delivered by each electrode, despite possible manufacturing tolerances in capacitors used in such a system.

As illustrated, the capacitive divider 2200 includes first and second capacitors 2204, 2206 electrically connected in series between an electrode connection of a lead of the implantable medical device and a ground 2208. The capacitive divider 2200 can be used to monitor for possible DC offset effects present in the medical device. For example, in some embodiments, the capacitive divider 2200 can be used to detect peak positive and negative voltages generated by the device (e.g., as illustrated in waveform 2300, discussed below), to determine uniformity of positive and negative signal generation. Non-uniform positive and negative signals (or signal duration) can result in an overall DC offset across a patient's tissue, which, over time, can potentially have detrimental effects to the patient.

Furthermore, due to manufacturing variances in capacitive values among various capacitors, a voltage output received at the microprocessor from the capacitive divider may vary among devices, despite the fact that the same voltage value may be present at the electrode. In some embodiments, the capacitive divider therefore generates a voltage measurement that can be passed to the microprocessor, to calculate a capacitive ratio, based on the voltage observed by the microprocessor and the known voltage output from a high voltage source. The capacitive ratio can be used to ensure that the correct (and consistent) current level is delivered to the lead arrangement 108, for example by allowing the microprocessor to adjust the output of the high voltage source. For continued monitoring, the microprocessor is configured to calculate an initial ratio of capacitances and periodically calculate a second ratio of capacitances based on the first and second capacitors 2204, 2206. The microprocessor then compares the second ratio to the first ratio to calibrate a voltage or current output by the medical device.

In various embodiments of the devices discussed herein, the capacitors 2204, 2206 can have a number of different values, depending upon the particular electrical characteristics of the therapy to be delivered, as well. For example, in some embodiments, capacitor 2204 can be a 47 pF capacitor, and capacitor 2206 can be a 220 pF capacitor. It is understood that additional capacitance, such as a parasitic capacitance present in the circuit, may be present as well. Furthermore, the capacitors, due to manufacturing variances, may depart from desired or expected values, either initially or over time. For example, the voltage exposed to the microprocessor may vary among the various tip and ring connections, and may vary over time as capacitors fail. In some embodiments of the medical device disclosed herein, a capacitive calibration process can be integrated into operation of the device, to control current flow across tip and ring connections and to guard against capacitor failure. An example of such a test is discussed below in connection with FIG. 31.

Figure 28:
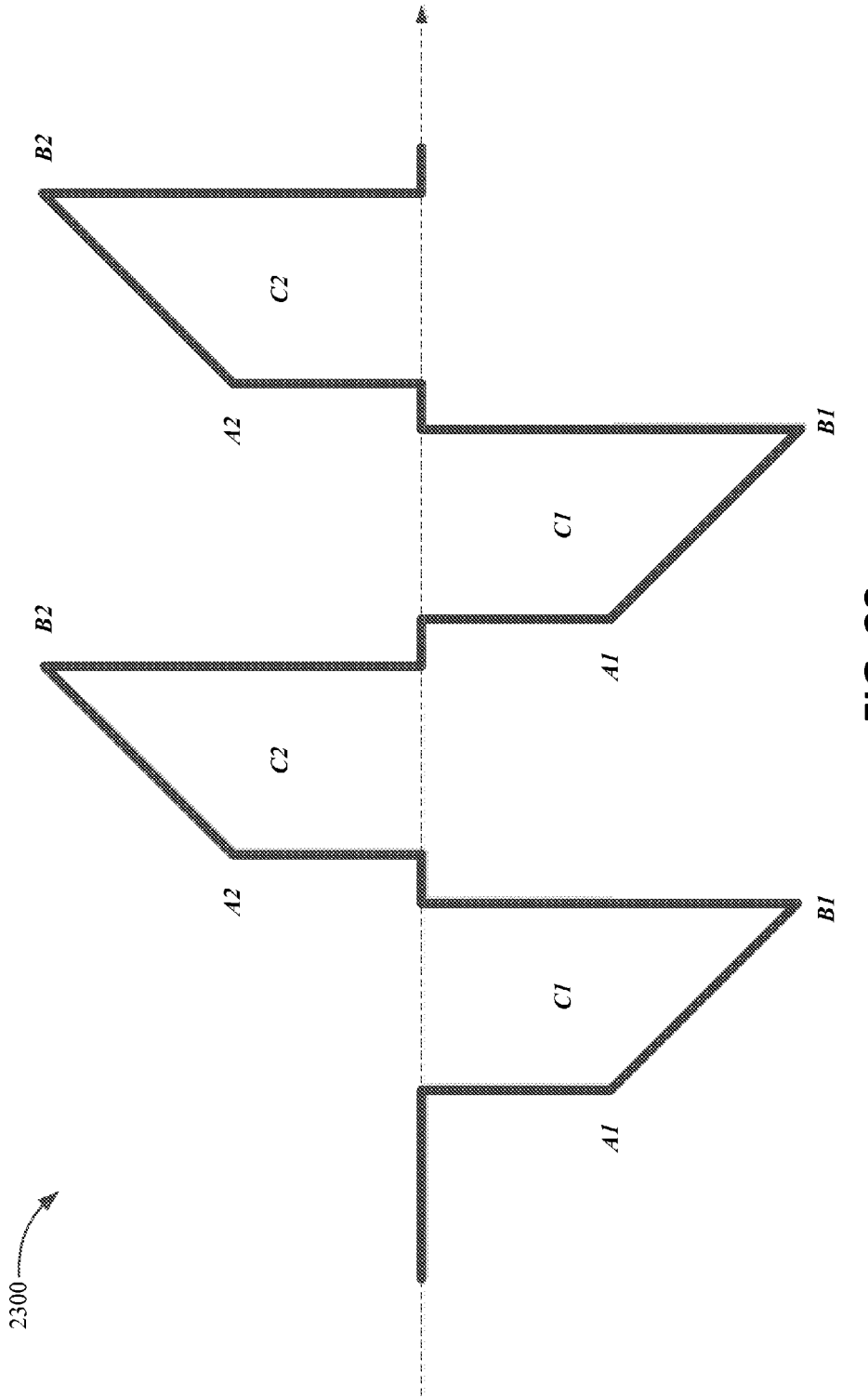
FIG. 28 is a graphical representation of an example voltage output of electrical leads of a medical device.

Now referring to FIG. 28, a graph illustrating an ideal output voltage waveform 2300 produced between two electrical contacts of a medical device is shown. In various embodiments, the waveform 2300 can represent a therapy applied from a tip connection to a ring connection at one or both electrodes of a medical device, such as are illustrated above in connection with FIGS. 25-26. Alternatively, the waveform 2300 can be applied in a tip-to-tip arrangement across two electrodes.

In preferred embodiments, the waveform is symmetric, as shown. In the embodiment shown, each symmetric positive and negative signal portion of the waveform includes first and second peaks, e.g., A1 and B1, or A2 and B2, respectively.

These peaks represent voltage difference variations between tip and ring connections, respectively. For example, the A1 and B1 peaks can represent connection of a tip connection to a ground (at A1), and subsequent connection of the ring connection to a positive voltage (at B1), thereby creating a negative potential from tip to ring. The A2 and B2 peaks can, correspondingly, represent connection of the tip connection to a positive voltage (at A2), and subsequent connection of the ring connection to ground (at B2).

To attempt to maintain symmetry between positive and negative signal portions of a pulse, the magnitudes of peaks A1 and A2, B1 and B2, and areas C1 and C2 are approximately equal, respectively. In some embodiments, the waveform 2300 as illustrated is executed at a 5 kHz frequency, with each pulse width being approximately 90 microseconds long. In alternative embodiments, the waveform can be executed at a 2.5 kHz frequency, effectively doubling the distance between adjacent sets of positive and negative pulses. Furthermore, in some embodiments, the current delivered using the therapy can be approximately 1-8 milliamps. In one example embodiment, a 4 milliamp signal is delivered, within 5% of a known value. Still other variations to the waveform are possible as well. In general, changes in symmetry among the various peaks and areas defined by the waveform 2300 can, due to greater positive or negative current time (i.e., areas C1 and C2), result in an overall DC current passing between the two electrodes or tip/ring arrangements, depending upon the specific configuration used. As such, it is desirable to limit such DC current, for example to less than one microamp.

c. Clock Accuracy Adjustment Circuit

Another aspect of the disclosure provides a clock accuracy adjustment circuit. Implantable neuroregulators include a microprocessor as exemplified in FIG. 3A-3B and as identified as CPU 154. Activities of the microprocessor are synchronized by a clock signal. Typically, quartz piezo-electric oscillators are used to generate clock signals for microprocessors. In some instances Resistor-Capacitor (RC) circuits are used to generate clock signals for microprocessors. Quartz oscillators are generally more accurate than RC circuit because RC Circuits may drift over time. Drift may cause a therapy to be applied at the wrong time, or a therapy to be applied incorrectly. Quartz oscillators consume more power than RC circuits. These types of oscillators cannot be used in a low-power system intended to have a long-lasting battery. The battery's life can be extended by minimizing the power consumption of the medical device.

In embodiments, to help minimize the power consumption of the medical device, an RC circuit generates the clock signal instead of a quartz oscillator. Because the RC circuit is less accurate than a quartz oscillator, the RC circuit needs to be fine-tuned in order to ensure that the RC circuit generates a clock signal at an appropriate frequency. Tuning the RC circuit is necessary to get optimum communications performance and to get accurate delay timing. In an embodiment, a method for adjusting RC Circuit accuracy involves usage of integrated circuit and/or crystal oscillator for resynchronization of RC Circuit.

In embodiments, a method for tuning an RC circuit clock comprises activating an integrated circuit and/or crystal oscillator, initiating instructions in the microprocessor to count an actual number of oscillator transitions of the integrated circuit and/or crystal oscillator during a defined period of time; comparing the actual count of oscillator transitions to an expected count of oscillator transitions, determining if the count is out of range and calculating an OscValue by determining the difference between that expected count and the actual count; setting an a control register to a value that indicates the change in actual oscillator transitions during the defined period of time; and adjusting oscillation of the RC circuit clock based on the value in the control register. In embodiments, the integrated circuit is a real time clock such as a real time clock having a frequency of 32 KHz. In other embodiments, any type of crystal oscillator can be utilized. In embodiments, the crystal oscillator and/or integrated circuit are activated for a defined period of time and then turned off in order to conserve power. In embodiments, the RC circuit clock signal has a frequency of about 8 MHz. In embodiments, the count of oscillator transitions occurs during one or more defined time periods of at least 4 msec intervals. In embodiments, the RC circuit clock adjustment is scheduled at least once daily. In other embodiments, the RC circuit is tuned at least once daily and at any time the device is powered up.

In an embodiment, a system comprises a neuroregulator comprising a microprocessor comprising a RC circuit; and an integrated circuit and/or crystal oscillator that functions as a real time clock. In embodiments, the microprocessor contains instructions for implementing a method for tuning a RC circuit as described above. The microprocessor comprises an activate module to activate the integrated circuit and/or crystal oscillator for a period of time and then to deactivate the integrated circuit and/or crystal oscillator after tuning is completed. The microprocessor further comprises a counting module to count the actual oscillator transitions of the integrated circuit and/or crystal oscillator over a defined period of time; a compare module to determine if the count is out of range and calculating an OscValue by determining the difference between that expected count and the actual count; and an adjustment module to set a control register to a value that indicates the change in actual oscillator transitions during the defined period of time and to adjust oscillation of the RC circuit based on the value in the control register. An example of a control register is an OSCTUNE register.

In other embodiments, a method of tuning an RC circuit involves a downlink carrier frequency. In an embodiment, a method comprises counting the number of carrier frequency oscillations in a set number of RC clock cycles to determine the need to adjust the RC clock; determining if the actual oscillation frequency of the carrier frequency is different than the expected carrier frequency oscillation; adjusting the RC clock oscillations based on any difference between the actual carrier frequency oscillations from the expected carrier frequency oscillation. In embodiments the RC circuit clock signal has a frequency of about 8 MHz. In embodiments, the downlink carrier frequency is the carrier frequency of a data signal communicated from an external device to the neuroregulator. In embodiments, the downlink carrier frequency is about 19.2 MHz. In embodiments, the count of oscillator transitions during a defined time periods of at least 4 msec intervals. In embodiments, the RC circuit clock adjustment is scheduled at least once daily. In other embodiments, the RC circuit is tuned at least once daily and/or at any time the neuroregulator receives a downlink carrier signal. In embodiments, a microprocessor comprises a counting module to count the number of carrier frequency oscillations in a set number of RC clock cycles, a compare module to determine if the actual oscillation frequency of the carrier frequency is different than the expected carrier frequency oscillation, and an adjustment module to adjusting the RC clock oscillations based on any difference between the actual carrier frequency oscillations from the expected carrier frequency oscillation In other embodiments, a method of tuning an RC circuit involves bit mapping. In an embodiment, a method comprises determining bit timing in a set number of RC clock cycles to determine the need to adjust the RC clock; determining if the bit timing is different than the expected bit timing; adjusting the RC clock oscillations based on any difference between the actual bit timing from the expected bit timing. In embodiments the RC circuit clock signal has a frequency of about 8 MHz. In embodiments, the bit timing is determined by using bit edges to detect signals (e.g. sending alternating 1's and 0's or other pattern). In embodiments, the bit timing is measured during a defined time periods of at least 4 msec intervals. In embodiments, the RC circuit clock adjustment is scheduled at least once daily. In other embodiments, the RC circuit is tuned at least once daily and/or at any time the neuroregulator receives a downlink carrier signal.

5. External Computer Interface

Programmer software, with which the physician can program treatment configurations and schedules, resides on and is compatible with an external computing device 107 (FIG. 1) that communicates with the external charger 101. In general, application software for the computing device 107 is capable of generating treatment programs stored in a commonly accepted data file format upon demand.

The programming interface of the computing device 107 is designed to enable the physician to interact with the components of the therapy system 100. For example, the programming interface can enable the physician to modify the operational modes (e.g., training mode, treatment mode) of the external charger 101. The programming interface also can facilitate downloading treatment parameters to the external charger 101. The programming interface enables the physician to alter the treatment parameters of the neuroregulator 104, and to schedule treatment episodes via the external charger 101.

The programming interface also enables the physician to conduct intra-operative testing amongst the components of the therapy system 100. For example, the physician can initiate a lead impedance test via the programming interface. The physician also can program temporary treatment settings for special physiologic testing. The programming interface also can facilitate conducting diagnostic stimulation at follow-up visits between the patient and the physician.

The programming interface of the computing device 107 also enables the physician to access patient data (e.g., treatments delivered and noted physiological effects of the treatment). For example, the programming interface can enable the physician to access and analyze patient data recorded by the therapy system 100 (e.g., stored in the memory 152 of the neuroregulator 104 and/or the memory 181 of the external charger 101). The physician also can upload the patient data to the external computing device 107 for storage and analysis.

The programming interface also can enable the physician to view system operation information such as non-compliant conditions, system faults, and other operational information (e.g., lead impedance) of the therapy system 100. This operational data also can be uploaded to the external computing device 107 for storage and analysis.

i. Programming Access Level

In certain embodiments, the programming interface defines at least two levels of access, one for the physician and one for the system manufacturer. The programming interface can provide different types of information to a requestor depending on what level of access the requestor has. For example, the programming interface may enable the system manufacturer to program system settings (e.g., default values for treatment parameters, acceptable ranges for treatment parameters and/or system settings, system tolerances, etc.) that cannot be adjusted by the physician.

In an embodiment, a user with a high level of access can select, for each system setting, the level of access required before the programming interface will enable a user to modify the system setting. For example, the system manufacturer may wish to prevent treating physicians from modifying default treatment settings. It will be appreciated that generating software implementing the above-described features of the programming interface is within the skill of one of ordinary skill in the art having the benefits of the teachings of the present application.

6. Charge Balancing

Nerves may be damaged when exposed to direct current (e.g., net current from electrical stimulation) over extended periods of time. Such damage may result from very small net currents acting over a long time, e.g. microamperes of current over minutes. For example, direct current can be caused by a voltage buildup at the electrodes 212, 212*a* (FIG. 1) due to inherent differences in electrode component values.

Charge-balancing advantageously mitigates (and may eliminate) damage to the nerve due to charge build-up during treatment. However, conventional processes for achieving a current/charge balance to within (for example) 1 μA in a current of about 6 mA place inordinate requirements on the implantable device of providing consistent power at a consistent frequency. Below are descriptions of two processes for balancing charge, a timing process and a shorting process, that do not require such inordinate consistency.

i. Timing Correction

Figure 20:
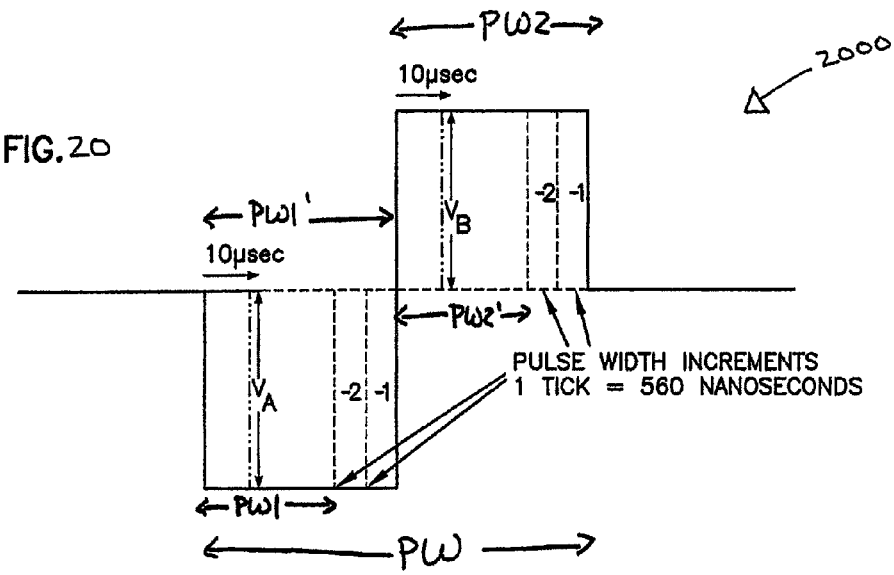
FIG. 20 is a schematic representation of a signal pulse illustrating charge balancing according to aspects of the present disclosure.

Referring to FIGS. 20-24, charge or current on the patient's nerves can be balanced by applying a correction to a pulse-width PW of a treatment signal pulse 2000 over a number of cycles (see FIG. 20). A cycle refers to a single iteration of the pulse. The correction includes adding or subtracting a "timer tick" to the pulse-width PW of at least one phase of the treatment signal pulse 2000 to increase or decrease the pulse-width for a period of time. In an embodiment, an example timer tick can equate to the minimum resolution of the applied clock frequency (e.g., about 560 nanoseconds).

Typically, the treatment signal pulse 2000 is a bi-phasic (e.g., having a negative phase and a positive phase) pulse signal having a pulse-width PW. In general, the negative charge provided by the first phase of the signal pulse 2000 is balanced by the positive charge provided by the second phase of the signal pulse 2000. One or more timer ticks can be added to one or both phases of the pulse 2000 to correct a charge imbalance.

In the example shown in FIG. 20, the first phase of the signal pulse 2000 has a first pulse-width PW1 and the second phase of the signal pulse 2000 has a second pulse-width PW2. One or more timer ticks can be added to the pulse-width PW1, PW2 of one or both phases of the signal pulse 2000. For example, the pulse-width PW1 of the first phase can be increased by two timer ticks to a pulse-width of PW1'. Alternatively, the pulse-width PW2 of the second phase can be decreased by two timer tick to a pulse-width of PW2'.

To determine the number of timer ticks to add or subtract from each pulse-width, the neuroregulator 104 periodically can measure the voltage of the signal applied to each lead electrode 212, 212*a* of lead arrangement 108. The combination of charge buildup sensing and pulse width control creates a feedback loop to minimize the resulting voltage offset. Advantageously, this sense and control process is effective in the presence of physiologic variations, circuit tolerances, differences in electrode size, and temperature changes.

For example, as shown in FIGS. 3A and 3B, the electrodes of each lead (e.g., the tip electrodes 212, 212*a* in contact with the anterior and posterior vagal nerves AVN, PVN, respectively) are coupled to the CPU 154 of the neuroregulator 104 via a capacitive divider 162. The CPU 154 provides timed instructions to the output module 161 for controlling the voltage measurements $V_A$, $V_B$ of the signals applied by the electrodes 212, 212a (FIG. 1).

Between pulses, the microprocessor CPU 154 can zero the capacitive divider 162, release the capacitive divider 162 at a predetermined time relative to the signal cycle, and measure the voltages $V_A$, $V_B$ of the electrodes 212, 212a. For example, the CPU 154 can zero the capacitive divider 162, release the capacitive divider 162 approximately ten microseconds into a negative phase of the pulse, and measure the voltages $V_A$, $V_B$ (see FIG. 20). The CPU 154 can subsequently measure the voltages $V_A$, $V_B$ at approximately 10 microseconds into a positive phase of the pulse. If the voltage measurement $V_A$ of the electrode 212 is greater than the voltage measurement $V_B$ of the second electrode 212a, then the CPU 154 delivers instructions to decrease the pulse width (e.g., by about 560 nanoseconds) of the negative phase of the pulse of the next/subsequent cycle.

The above process may be repeated at a sampling frequency (e.g., typically about 40 Hz). Gradually, the number of pulse width corrective increments ("timer ticks") applied to the signal can be adjusted. For example, the pulse width PW1 of the positive phase of the pulse can be increased or decreased every sample period until the voltage measurement $V_A$ of the first electrode 212 is less than the voltage measurement $V_B$ of the second electrode 212a. In such a case, the pulse width PW2 of the negative pulse then can be increased to achieve balance. When the maximum pulse width PW2 of the negative phase of the pulse is reached, then the pulse width PW1 of the positive phase of the biphasic pulse may be decreased to maintain balance. In a preferred embodiment, the corrective increment is applied to a series of signals until the net offset current is well below a target current (e.g., about 1 μA).

In an embodiment, the amplitudes of the positive and negative phases of the pulse are compared very early in the cycle, and a relatively large correction is initially applied to the pulse width of the signal. Subsequently, the balancing correction is refined by changing the pulse width by only the one or two ticks as described above.

Advantageously, the charge-balancing goal can be achieved over a number of these cycles using the above described processes without requiring a high clock frequency. Because the charge buildup tends to be a slow process, correcting the charge buildup can be done less frequently than delivering therapy signals. For example, in an embodiment, therapy signals can be delivered at about 5 kHz and correction pulses can be delivered at about 40 Hertz.

Figure 21:
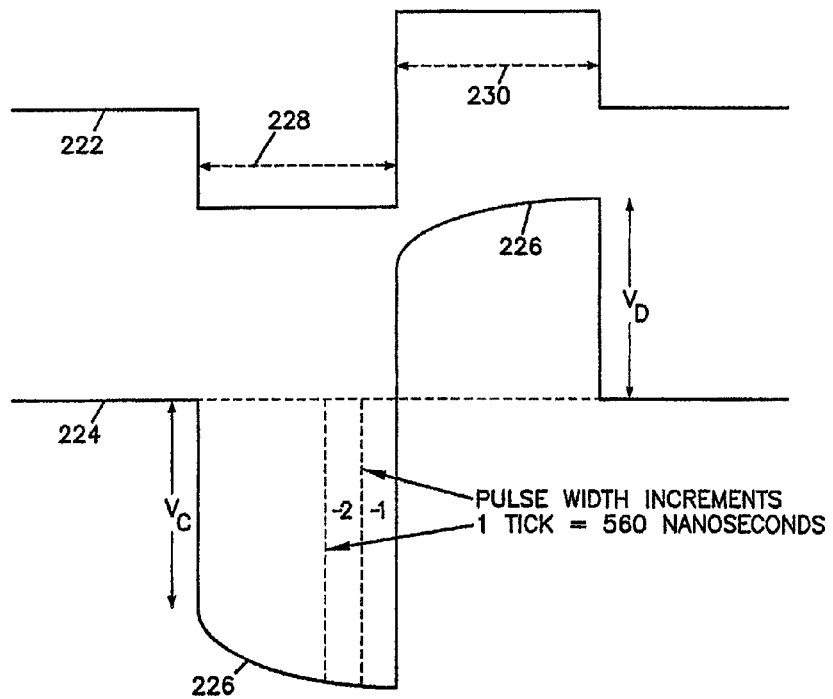
FIG. 21 is a schematic representation of an alternative means of charge balancing according to aspects of the present disclosure.

FIG. 21 illustrates an example application of charge balancing through timing corrections. FIG. 21 illustrates a blocking waveform 222 (e.g., a biphasic, symmetric current waveform), which results in a voltage waveform 224 at the electrode-tissue interface. The voltage waveform 224 includes an exponential voltage component 226 which reflects the fact that the electrode-tissue interface has capacitive elements, resulting in charging and discharging of this capacitance.

In one cycle of the current waveform 222, the charge applied to the electrode-tissue interface is balanced when the voltages $V_C$ and $V_D$ are equal. Accordingly, in such a case, the net potential of the electrode-tissue interface is zero. As described above, however, there are a number of reasons why, in practice, voltages $V_C$ and $V_D$ may not be equal, resulting in a charge imbalance.

Typically, in practical operation, the voltage values of $V_C$ and $V_D$ are measured periodically (e.g., about every 25 milliseconds). If the voltage $V_C$ is greater than the voltage $V_D$, then the pulse width 228 of the first phase of the current waveform 222 is reduced by one "timer tick," and applied for about 1 millisecond. At the end of subsequent measurement periods (e.g., about every 25 milliseconds), the values of voltages $V_C$ and $V_D$ are measured again. When the voltage $V_C$ is greater than the voltage $V_D$, the pulse width 228 of the first phase is reduced by an additional timer tick. The current waveform 222 having the phase with the reduced pulse-width 228 is applied for an additional 1 millisecond.

When the value of the voltage $V_C$ is eventually less than the value of the voltage $V_D$, then the pulse width 228 of the first phase can be increased by one timer tick for 1 millisecond for each measurement period. In this situation, it may be that the maximum pulse width (as determined by the applied frequency of the therapy) 228, is reached while the voltage $V_C$ is still less than the voltage $V_D$. If this occurs, then the pulse width 230 of the second phase of the current pulse 222 is decreased one timer tick at a time, as described above, until equilibrium is established (i.e., $V_C = V_D$).

Additionally, in the methods represented by FIGS. 20 and 21, the microprocessor CPU 154 can short out the electrodes 212, 212a at the beginning, midpoint and/or end of the biphasic, square-wave, current pulse, as described in more detail herein. Over a series of such sampling cycles, it has been demonstrated that the net offset current is well below the design goal of 1 μA.

During a feedback cycle, software stored in the microprocessor CPU 154 can initiate a therapy shut down if the sensed voltage offset exceeds safe values. This is an advantageous feature in actual use, where electrode configurations and other parameters could vary.

By using a combination of both hardware (i.e., electrode shorting) and closed-loop software techniques, the average charge imbalance may be lower than with either method individually.

At the end of therapy delivery, it is useful to have the hardware briefly drain any residual charge. Subsequently, the circuitry may be made safe until the next therapy delivery and the software loop turned off.

ii. Shorting Correction

Some processing for achieving charge balance have involved the use of biphasic pulses in which, for example, the negative charge provided by the first part of the waveform is balanced by the positive charge provided by the second part of the waveform. Further details describing the use of electrode shorting to achieve charge balancing can be found in U.S. Pat. No. 4,498,478 to Bourgeois, issued Feb. 12, 1985; U.S. Pat. No. 4,592,359 to Galbraith, issued Jun. 3, 1986; and U.S. Pat. No. 5,755,747 to Daly et al, issued May 26, 1998, the disclosures of which are hereby incorporated by reference herein.

FIGS. 22-24 illustrate a preferred charge balancing process. FIGS. 22 and 23 schematically illustrate an implanted circuit 112 of a neuroregulator 104 connected to nerve electrodes 212, 212a. The circuit 112 has components schematically illustrated as a switch 150 for selectively creating an electrical short between the electrodes 212, 212a. In FIG. 22, the switch 150 is arranged in a short state to create an electrical short between electrodes 212, 212a. In FIG. 23, the switch 150 is arranged in a non-short state with no short being created between the electrodes 212, 212a.

FIG. 24 schematically illustrates signal waveforms $W_1$, $W_2$, $W_{1A}$, $W_{2A}$ produced at the electrodes 212, 212a under various conditions of operation of the switch 150. The waveforms $W_1$ and $W_2$ show the signals produced at electrodes 212, 212a, respectively, when the switch 150 is arranged in the non-short state. Each waveform $W_1$ and $W_2$ has a negative pulse and a positive pulse of equal pulse width PW. The waveforms $W_1$, $W_2$ are out of phase so that the negative pulses of the waveform $W_1$ occur during the positive pulses of the waveform $W_2$.

It will be appreciated, these waveforms are illustrative only. Any other waveform (e.g., the time offset waveform $W_{12A}$ of FIG. 18 could be used). In addition, while the short is shown between electrodes 212, 212a, the short alternatively or additionally could be created between cathode and anode pairs 212, 218 and 212a, 218a, previously described.

In the example shown, the switch 150 is operated to create a short between electrodes 212, 212a at the start of each pulse and for a duration $D_S$. The waveforms at electrodes 212, 212a resulting from such shorting are shown in FIG. 24 as $W_{1A}$, $W_{2A}$. As a result of the short, any charge build-up at an electrode (e.g., electrode 212) is distributed to the oppositely charged electrode (e.g., electrode 212a). The pulse width PW of each pulse is reduced to a pulse width $PW_A$. Advantageously, repeating this process throughout the therapy maintains any net charge build-up below tolerable levels.

The example given shows the short state occurring at the beginning of each signal pulse. This is illustrative only. The short state can occur at the beginning, end or any intermediate time of a signal pulse. Furthermore, the short state need not be applied to every pulse, but rather can occur intermittently throughout the pulse cycles or even during time delays between pulses. When applied during a pulse cycle, the duration $D_S$ of the short is preferable not greater than about 10% of the pulse width PW. For example, the duration $D_S$ can range from about 10 μs to about 20 μs.

iii. Therapy Calibration, Safety Limits and Safety Checks

The design of the neuroregulator 104 (FIG. 3) includes a capacitive divider 162 and an output module 161 to measure the voltage present at the lead arrangement 108 (e.g., the tip electrodes 212, 212a and/or ring electrodes 218 and 218a of both anterior and posterior leads 106, 106a). The output module 161 can measure the current flow through the electrodes arranged in any of the four electrode configurations (see FIGS. 11, 13, 15, and 17). A programmable current source (not shown) can enable a physician to select how current is delivered through the electrodes 212, 212a, 218, and 218a to the nerve.

Before therapy is delivered, the physician can calibrate the neuroregulator 104 to ensure the desired current can be delivered to the nerves. For example, this calibration can be accomplished by connecting the programmable current source from a power source to ground and adjusting the current to the desired level. Current does not flow through the leads 106 during this calibration procedure. If the desired current cannot be delivered, or if the DC voltage offset is greater than a programmed limit, then the therapy can be terminated (e.g., such conditions trigger a flag or error alert).

Advantageously, calibrating the therapy system 100 significantly reduces the effect of component tolerance, drift, and aging on the amount of current delivered. In addition, the capacitive divider 162 can be calibrated before therapy is delivered. Advantageously, calibrating the divider 162 can enhance the accuracy of the safety checks from a 20% worst case value to approximately 2%.

During therapy, the current between the active electrodes is measured during each signal pulse to ensure that the delivered current is within the programmed tolerance (e.g., +/− about 5%).

Additionally, in order to determine the state of charge balance, the therapy system 100 can determine a peak-to-peak voltage quantity for each signal pulse. The peak-to-peak voltage quantity is divided by two and compared to the peak voltage measurement of each phase of the waveform. If the deviation exceeds a predetermined value, the therapy can be shut down.

Figure 29:
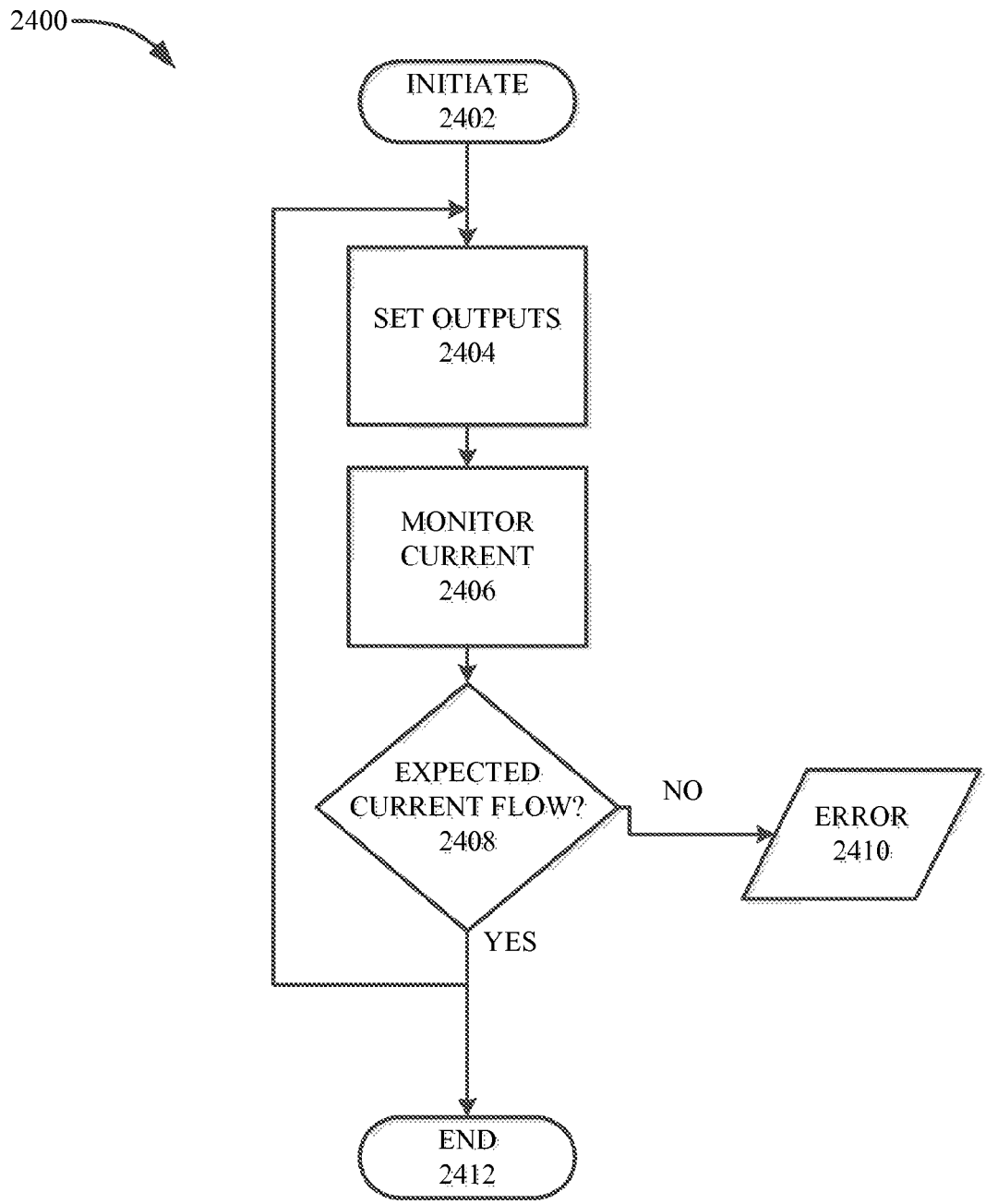
FIG. 29 is flow chart of an example embodiment showing the steps for conducting safety checks on an H-bridge circuit of a medical device.
Figure 30:
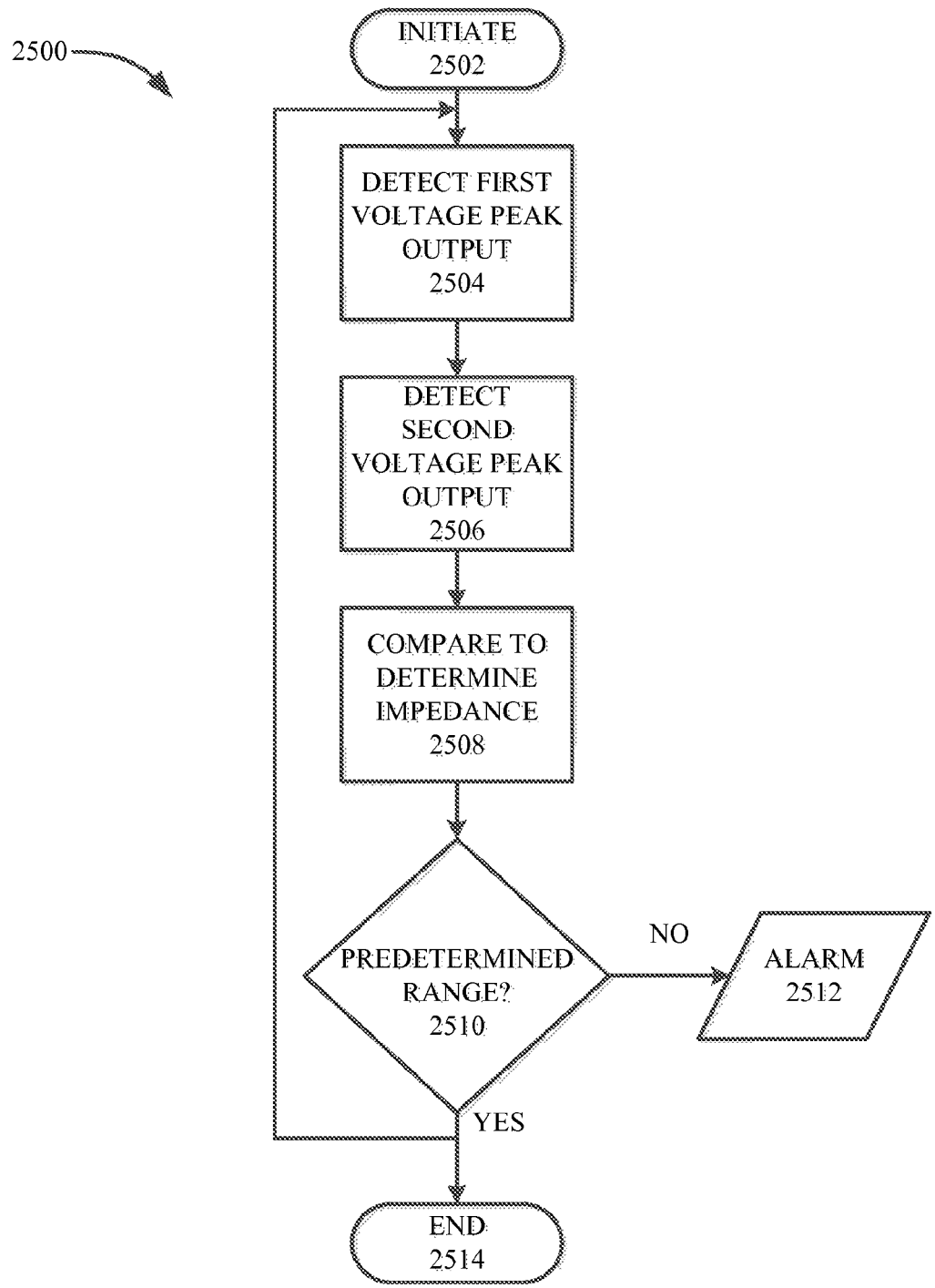
FIG. 30 is a flow chart of an example embodiment showing the steps for conducting an impedance measurement check on a medical device.
Figure 31:
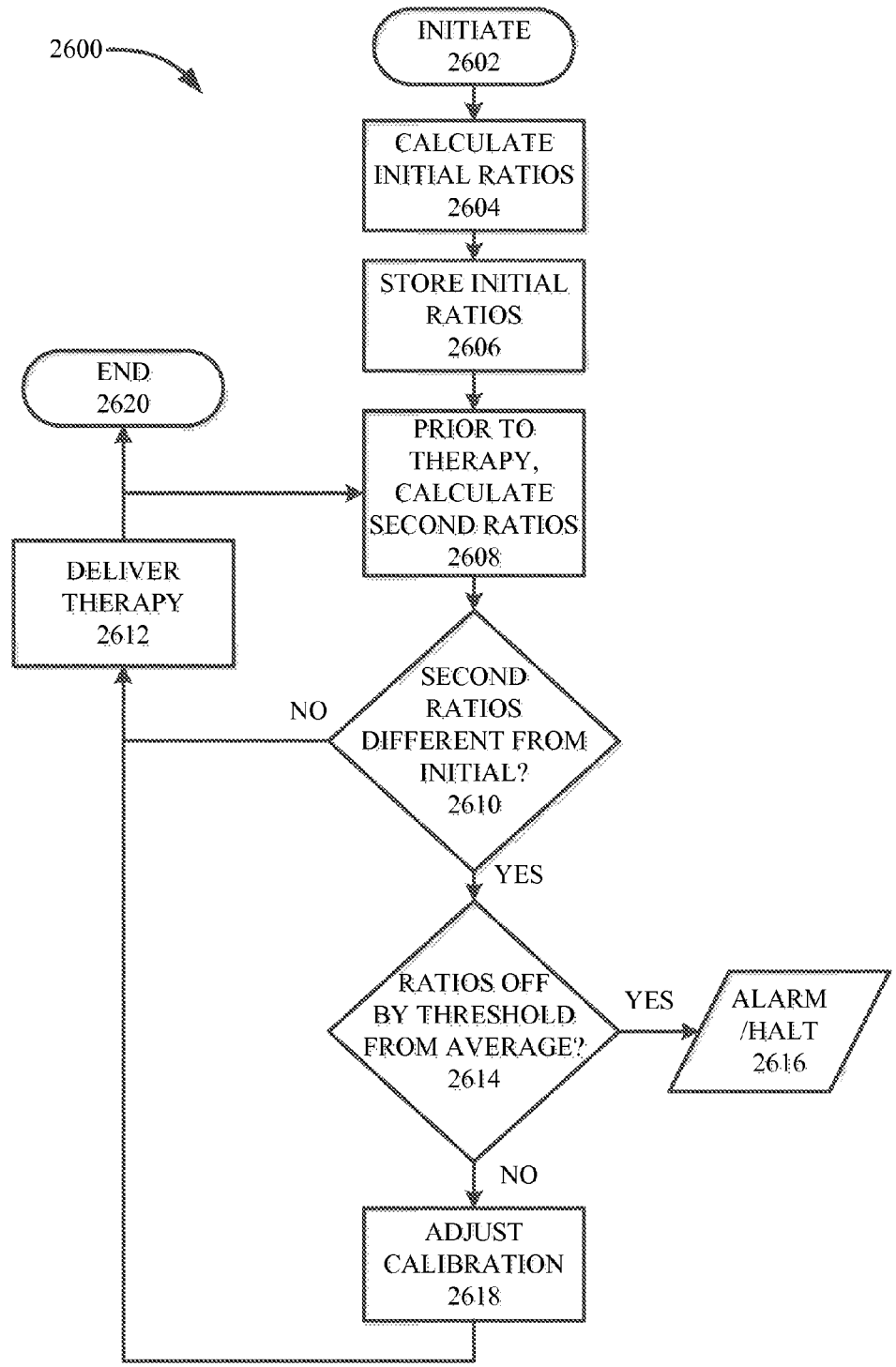
FIG. 31 is a flow chart of an example embodiment showing the steps for calibrating electrical signal output of a medical device.

Referring now to FIGS. 29-31, various test methods that can be employed within a system 100, and in particular a medical device 2000 as illustrated in FIGS. 25-28 are illustrated. In general, the test methods discussed herein represent algorithms that can be performed, either in whole or part, by a processing unit (e.g., CPU or other programmable circuit) periodically to ensure continued accurate and safe operation of the device/system. FIG. 29 describes an example method of performing safety checks of the H-bridge leading to the lead arrangement 108, while FIG. 30 describes an example method for monitoring impedance, and therefore detecting any potentially harmful DC offset effects occurring in the delivered therapy. FIG. 31 illustrates an example method for implementing a capacitive divider and thereby adjusting output current to the lead arrangement 108

Now referring to FIG. 29, a flow chart of an embodiment of the present disclosure showing a method 2400 for conducting safety checks on an H-bridge circuit of a medical device is illustrated. The method 2400 generally revolves around testing activation of the various switches available in an H-bridge circuit, such as the circuits 2132, 2134 of FIG. 26.

The method 2400 involves periodically initiating a sequence of tests of an H-bridge circuit (step 2402). This can occur, for example, prior to initiating operation of the device 2000, or periodically during operation or delivery of a therapy. The method 2400 involves, at that predetermined or periodic time for testing the circuit, transmitting a set of control signals input to switches in an H-bridge circuit (step 2404), for example, driving such signals from a microprocessor and/or FPGA, such as those illustrated in FIG. 25.

The method 2400 further includes, during each test (i.e., while certain switch inputs are set), monitoring a current flow across a sensing resistor electrically connected between a sensing connection of the H-bridge circuit and a ground (step 2406) but while not therapy is being delivered. In embodiments, in a therapy cycle therapy delivery signals are stopped, an H bridge safety check is conducted, and then therapy is resumed. A current flow through the sensing resistor indicates that both series switches, within at least one of the two pairs of series switches are active during that test, while absence of current indicates that at least one of the series switches is non-functional, as explained above with respect to FIG. 26. A current assessment operation determines whether a detected current flow is outside of an expected range of acceptable currents (operation 2408). If the current flow is outside of an expected range (e.g., a high current during the first type of status checks discussed above, or a low current during the second type of status checks discussed above), the system enters an alarm state (step 2410), and halts operation to prevent unintentional injury to the patient. If the current flow is within the predetermined range of acceptable current for the given test, operation either returns to reset the test inputs for testing a next subsequent combination of switches (step 2404), or the test completes (at end step 2412).

Overall, the sequence of tests is configured to test each switch connection of two pairs of series switches connected in parallel between a voltage supply and the sensing connection. In one embodiment, the method illustrated in FIG. 29 can be implemented by the circuitry shown in FIGS. 25-26. For example, the microprocessor 2002, configured to send and receive signals indicative of activity in the H-bridge circuit 2006 may periodically perform the sequence of tests on the H-bridge circuit 2006 during operation of the device 2000 to ensure proper operation of the H-bridge circuit 2006. In such embodiments, the FPGA 2004, configured to receive the signals sent by the microprocessor 2002 regarding a desired state, may control the current flow through the H-bridge circuit 2006 by setting the various switches included in the H-bridge circuit 2006. To accomplish this, the FPGA 2004 may control the voltage of the gate inputs of the H-bridge circuit based upon the signals sent by the microprocessor 2002. In either example, if the current flow through the sensing resistors 2014, 2016 is above a predetermined threshold current, either the microprocessor 2002 halts and/or aborts use of the medical device 2000, and in some embodiments, triggers an alarm.

In some embodiments, the sequence of tests can be executed either prior to operation, or periodically during operation of the device 2000. For example, in some embodiments, a sequence of tests of H-bridge circuitry can be executed approximately every four seconds during operation of the device. Other periods, or scheduled tests, could be used as well.

Now referring to FIG. 30, a method 2500 for conducting impedance measurement checks on a medical device is shown. The method 2500 can be executed by a device such as device 2000 of FIG. 25, and can be performed, for example, continually during delivery of a therapy. In particular, the impedance checks provided by the present disclosure can utilize capacitive dividers, such as those illustrated in FIGS. 26-27, for measuring impedance of a circuit, for example to determine the existence of a DC offset in a delivered electrical signal delivered as a therapy to a patient. A greater than expected DC offset, signifying less than adequate current flow through one or both of the electrical contacts, can affect the electrical simulation applied by the electrical contacts onto a patient.

In the embodiment shown, after initiation (step 2502), the method 2500 includes detecting a first voltage peak output between two electrical contacts of a medical device (step 2504). After this step, the process continues by detecting a second voltage peak output by the two electrical contacts of the device (step 2506). This second voltage peak output, based on the waveforms used in the therapy, has a magnitude approximately equal to but opposite in polarity from the first voltage peak output. These peaks can be, for example, the maximum peaks of the positive and negative portions of the waveform, such as points B1, B2 of FIG. 28. The difference between these peaks represents the DC offset of the circuit. By comparing the two voltage peaks, in particular by comparing the magnitudes of those peaks, at least a portion of an impedance (i.e., a capacitive portion) between the two electrical contacts is determined (step 2508). The impedance is then compared to a predetermine impedance range, such as a minimum or maximum acceptable impedance. If it is found that the determined impedance is outside a predetermined impedance range (step 2510), an alarm is generated indicating the presence of a direct current signal applied to the tissue of a patient (step 2512). However, if the determined impedance is within the predetermined range, the process will either begin again to confirm the impedance of the same electrical contacts, begin again to determine the impedance of two different electrical contacts (or the same two electrical contacts during delivery of a different therapy cycle; returning to step 2504) or end (step 2514). In some embodiments, this comparison can determine whether the DC offset exceeds 1 microamp; however, in alternative embodiments, other DC offsets may be deemed acceptable.

Referring to FIG. 30 generally, it is noted that in some embodiments, an improper DC offset can be calculated by determining the height difference between peaks A1/A2 and B1/B2, respectively, as illustrated in FIG. 27. In one embodiment, an impedance measurement device is used to calculate these height differences and ensure that the medical device is operational before each application of an electrical stimulus. In some embodiments, it is desirable to ensure that magnitudes of the peaks (e.g., comparing A1 to A2, and comparing B1 to B2) are within approximately 400 mV. However, in alternative embodiments, other thresholds could be used. In any event, to maintain a desired level of symmetry, peaks should be compared, as well as the duration of each pulse (e.g., the width of pulses C1, C2).

In varying embodiments, the method 2500 may include several other steps. For example, the process may begin again to detect a second positive and negative output voltage to determine a second portion of the impedance between the same electrical contacts. Further, in calculating the impedance, an electrical current of about 3 mA may be used. However, in alternative embodiments, this value may either be increased or decreased depending on various factors including the function of the medical device and the amount of electrical stimulus desired.

In still other embodiments, the process 2500 may include intermediary steps between detecting that the impedance is outside a predetermined range (step 2510) and generating the alarm (step 2512). For example, for purposes of accuracy, the process may include decreasing an operational voltage of the medical device and then detecting a second positive and negative voltage output by the same two electrical contacts of the medical device operating at the decreased operational voltage. After comparing the second voltage peaks to determine a second impedance, the second impedance may be compared to a predetermined range. If at this point the second impedance is determined to be outside the predetermined range, the process may include generating the alarm and halting use of the medical device. However, if the impedance or second impedance is determined to be within the predetermined range, the process may include restarting the medical device.

In one embodiment, the process 2500 illustrated in FIG. 30, can be implemented by a medical device, embodiments of which are shown in FIGS. 25-26. Specifically, the medical device of FIGS. 25-27 can be calibrated such that the voltage output between any two electrical connections 2124, 2126, 2128, 2130 produces the ideal waveform 2300, seen in FIG. 28. To do this, an impedance measurement device, such as capacitive dividers 2140, 2142, 2144, 2146 connected to a microprocessor, detect a negative and a positive voltage peak output between any two electrical connections 2124, 2126, 2128, 2130. By comparing the negative and positive voltage peaks, the impedance measurement device determines at least a portion of an impedance between the chosen connections, and ensures that the portion of the impedance is within a predetermined range of acceptable impedance values. In this way, the impedance measurement device confirms that the electrical stimulus applied to a vagal nerve of a patient is within a safe and appropriate range. If the portion of the impedance is not within the predetermined range, the impedance measurement device may trigger an alarm and/or halt usage of the medical device.

In varying embodiments of the present disclosure, the portion of the determined impedance may be the resistive portion or the capacitive portion of the impedance. Further, the sequence of tests conducted to ensure that impedance measurements conform to predetermined standards can occur at any time prior to application of electrical stimulus, for example in four second intervals, as programmed into the impedance measurement device, or as directed by the operator of the medical device. For instance, a programmable circuit, configured to execute program instructions, may be electrically coupled to the first and second electrical leads of the medical device. The programmable circuit, for example, the microprocessor 2002, can cause an impedance measurement device to perform the steps discussed above. In alternative embodiments, the programmable circuit may be an FPGA, such as FPGA 2004, or any other programmable circuitry capable to drive the operation of an impedance measurement device.

Referring now to FIG. 31, a flow chart of an example method 2600 showing the steps for calibrating electrical signal output of a medical device is illustrated. The method 2600 is useable in association with any of a variety of embodiments of the medical device, such as those illustrated in FIGS. 25-27. In particular, the method 800 provides for calibration of an output voltage by monitoring capacitor values in a capacitive divider.

The method 2600 is initiated (step 2602) upon initial operation of an implantable medical device, for example upon manufacturing of the device. The method 2600 includes calculating initial ratios between the capacitors in the capacitive divider for each electrode connection (i.e., each of the first and second tip and ring connections of FIG. 26, above) (step 2604). The initial ratios are calculated, for example, by using a known high voltage value from the a high voltage source, and detecting a voltage between two capacitors of the capacitor divider (e.g., as connected to a general purpose I/O pin of a microprocessor, as discussed above in connection with FIG. 27). This allows the initial ratios to be tested without applying a current through the electrode, because some or all of the H-bridge switches can remain disconnected during calibration. The method 2600 further includes storing the initial ratios in a memory, such as a memory associated with the microprocessor or FPGA of the medical device, for later reference (step 2606).

In some embodiments, calculation and storage of capacitive ratios can further include calculating and storing an average ratio for all of the capacitive dividers present within the device. If one or more of the capacitive ratios then diverges from that average number, either initially prior to use or after the device is implanted and a therapy is about to be delivered, it can be assumed that some malfunction occurred within the medical device (e.g., one or more of the capacitors failed).

In the embodiment shown, prior to actual delivery of a therapy, the method 2600 includes a second calculation of capacitive ratios for each of the electrode connections, or at least those used to deliver the therapy (step 2608). Those second ratios can then be compared to initial ratios prior to delivery of a therapy, to ensure that the correct current level is delivered (step 2610). If the second ratios are approximately the same as the initial ratios (i.e., they vary by less than a predetermined percentage, such as 5%), a therapy can be delivered (step 2612). If the ratios are off by some predetermined amount, a further assessment can be made, to determine whether any of the ratios diverges from an overall average of the capacitive ratios (step 2614). This comparison can be, for example, to the initial average determined and stored in steps 2604-2606, or to a current average of second ratios.

If one or more of the second ratios diverges from the overall average of ratios by at least a predetermined amount, an alarm is generated and operation of the medical device is halted (step 2616). The predetermined threshold can be set based on a number of parameters, for example based on a level of adjustability provided by the microprocessor or based on an expected threshold that would indicate failure of one or more of the capacitors in a capacitive divider. In some embodiments, the predetermined threshold is set at about 15% difference from the overall average capacitive divider ratio.

If none of the second ratios diverges from the overall average of ratios by greater than that preset, threshold amount, rather than halting operation, the microprocessor will calibrate outputs to the FPGA and/or voltage source to adjust the output current to be delivered on the electrode connections (step 2618), thereby providing a consistent output current for each electrode connection and across all electrode connections. Once the capacitive ratios are recalibrated, a therapy could be delivered (step 2612). Operation can terminate upon completion of the therapy (step 2620), or operation can loop back for recalibration and delivery of subsequent therapies during operation of the device.

Referring to FIGS. 29-31 overall, it is noted that, in addition to the steps/operations as shown can be performed in varying order, and also additional steps or operations could be performed. For example, an assessment operation for each of the initial ratios could be performed, analogous to step 2614. Additionally, in some other embodiments, status checks such as the recalibration procedure illustrated in FIG. 31 could be performed periodically rather than prior to each therapy delivery, for example every x minutes/seconds, or every x therapy deliveries.

In addition, relative to FIGS. 29-31 overall, it is noted that some of the logical operations of the various embodiments of the disclosure can be implemented as: (1) a sequence of computer implemented steps, operations, or procedures running on a programmable circuit within a computer, and/or (2) a sequence of computer implemented steps, operations, or procedures running on a programmable circuit within a directory system, database, or compiler.

In addition to the methods of FIGS. 29-31, the normal shutdown of the output module 161 shorts the electrodes together and connects them to ground through one of the current sources. Normally, this is a desirable and safe condition. However, certain failures could cause current to flow after shutdown, resulting in damage to the nerve. To eliminate this problem, an additional check can be made after normal shutdown has been completed. If current flow is detected, the leads are disconnected from each other (allowed to float) and the current sources are programmed to zero current.

7. Auto-Increment Therapy Delivery

For blocking therapy to be effective, energy delivery may need to be increased beyond the level that a patient perceives as acceptable at the initiation of therapy. The power of the therapy signals can be increased in small increments to enable the patient to acclimate to the more powerful therapy signals.

For example, the current of the therapy signal can be increased in steps of about 1 mA at weekly follow-up visits. Over time, patients may willingly accept multiple increments of 1 mA/week through periodic follow-up visits and programming sessions. For example, an initial setting of 3 mA may rise to at least 6 mA as a result of such follow-up sessions.

In certain embodiments of the therapy system 100, energy (i.e., power) delivery can be incrementally increased or decreased automatically over a pre-determined period of time. Advantageously, this automatic incremental increase can mitigate the need for frequent doctor office visits. This flexibility is especially convenient for patients who are located remote from the implanting bariatric center.

In an embodiment, the therapy system 100 automatically increases the current of the therapy signal by, for example, 0.25 mA every other day, cumulatively achieving the 1 mA/week incremental increase. In another embodiment, the therapy system 100 increases the current by about 0.125 mA per day. Initial studies have demonstrated such increment levels as acceptable.

The patient can retain the ability to turn therapy off at any time and return to the physician for re-evaluation. Alternatively, the patient can revert to previously acceptable therapy delivery levels (e.g., the therapy level of the previous day). For example, the patient can interact with the external charger 101 to issue such an instruction.

The physician can choose whether to activate the auto-increment therapy capability. The physician also can specify the date and/or time of therapy initiation and therapy parameters (e.g., including the starting and ending therapy parameters). The physician also may specify safety limits or tolerances for the therapy parameters. Additionally, the physician can specify the rate at which the therapy parameters are incremented over various time periods (e.g., about 0.5 mA/day for the first 7 days, then 0.125 mA/day over the following 24 days).

8. Predetermined Programs

One or more therapy programs can be stored in the memory of the external computer 107. The therapy programs include predetermined parameters and therapy delivery schedules. For example, each therapy program can specify an output voltage, a frequency, a pulse width, ramp-up rates, ramp-down rates, and an on-off cycle period. In an embodiment, the ramp-up rates and ramp-down rates can be individually and separately programmed.

In use, the physician may select any one of these therapy programs and transmit the selected therapy program to the implanted neuroregulator 104 (e.g., via the external charger 101) for storage in the memory of the neuroregulator 104. The stored therapy program then can control the parameters of the therapy signal delivered to the patient via the neuroregulator 104.

Typically, the parameter settings of the predetermined programs are set at the factory, prior to shipment. However, each of these parameters can be adjusted over a certain range, by the physician, using the computer 100 to produce selectable, customized, predetermined therapy programs. Using these selectable, customized therapy programs, the physician can manage the patient's care in an appropriate manner.

For example, when patients require more varied therapies, the neuroregulator 104 can store a therapy program including one or more combinations of multiple therapy modes sequenced throughout the day.

For example, referring to electrode configuration shown in FIG. 10, a single therapy program can include instructions to apply a blocking signal between electrode tips 212 (anterior vagal nerve) and 212a (posterior vagal nerve) from 8 a.m. to noon at 6 mA and 5 kHz; alternating between applying a blocking signal to posterior tip 212a to ring 218a and applying a blocking signal to anterior tip 212 to ring 218 from noon to 2 p.m. at 3 mA and 2.5 kHz; and applying a blocking signal from electrode tip 212 to electrode tip 212a from 2 p.m. from 2 p.m. to midnight at 6 mA and 5 kHz.

9. Operation Logs

In general, the neuroregulator 104 can have a time base to facilitate the delivery of therapy according to the treatment schedule. To determine this time base, the neuroregulator 104 can maintain one or more operating logs indicating the operations of the therapy system 100.

For example, the neuroregulator 104 maintains a time-and-date-stamped delivery log of the actual delivery of therapy. For example, the delivery log can include the time and date of initiation of each therapy episode, the time and date of completion of the therapy episode, the therapy parameters associated with the therapy episode. Both scheduled therapy and automatically-initiated therapy can be logged. The delivery log also can include a parameter to indicate whether the therapy episode was scheduled or automatically initiated.

Additionally, the neuroregulator 104 can maintain a time-and-date-stamped error log of all conditions that interfered with the delivery of therapy. For example, the error log can record all impedances measured, temperatures measured by the on-board temperature sensor, each instance in which the battery was charged by the external charger 101, each instance in which the battery reached its low-charge threshold, and each instance in which the battery reached its depleted threshold.

The delivery log and the error log are readable by the external computer 107 (e.g., a clinician programmer). In an embodiment, the delivery log and the error log each can accommodate up to about 3 months of data.

10. Detection of Food Passage Through the Esophagus

Neural blocking therapy can affect the rate at which the stomach empties and the level of intestinal motility. When applying neural blocking therapy for obesity control, it is desirable to determine the approximate times at which the patient ingests food (i.e., mealtimes) and the approximate quantity of food being consumed at each meal. Advantageously, with this information, the duty cycle of the therapy system 100 can be synchronized with the mealtimes. Additionally, the nature of the therapy can be adjusted in accordance with the quantity of food being consumed. For example, food detection is described in U.S. Pat. No. 5,263,480 to Wernicke et al, issued Nov. 23, 1993, the disclosure of which is hereby incorporated herein by reference.

In certain embodiments of the therapy system 100, the anterior and posterior vagal nerve electrodes 212, 212a can be positioned on the esophagus E adjacent to the junction between the esophagus E and the stomach. An impedance measurement between the anterior and posterior vagal nerve electrodes 212, 212a provides a measure of the presence of food in the esophagus E between the electrodes 212, 212a (e.g., see FIG. 11). The time integration of this impedance value provides a measure of the quantity of food consumed.

The impedance value between the electrodes 212, 212a can be measured by passing a low amplitude, sinusoidal signal (e.g., having a frequency of about 500-1000 Hz) between the electrodes 212, 212a. In an alternative embodiment, the impedance can be measured by passing the signal between the ring electrodes 218, 218a. In other embodiments, the dual bipolar lead/electrode configuration can operate as a quadripolar array.

In a quadripolar electrode array, two pairs of electrodes are typically secured in generally the same plane and normal to the length of the esophagus E. In such a configuration, a small signal applied across one pair of the electrodes (e.g., tip electrode 212, ring electrode 218) can be detected across the other pair (e.g., tip electrode 212a, ring electrode 218a). In general, changes in relative amplitude of the detected signal are proportional to changes in resistance of the signal path.

The impedance of the signal changes when food progresses down the esophagus E. This impedance change causes the amplitude of the detected signal to change, thereby providing an indication of the fact that food has passed, and giving an indication of the quantity of food. While a bipolar electrode pair may be used for both signal application and sensing across the esophagus E, it has the disadvantage of some interference as a result of polarization potentials.

More generally, this technology can be used to detect changes in the nature of the fluid within a vessel or lumen of the body. Such technology can be utilized in multiple applications. For example, this impedance measurement technology can be used to detect the presence of liquid/food in the distal esophagus to ascertain the presence of esophageal reflux. In another embodiment, this impedance measurement technology can be used in diagnosing eating abnormalities, such as bulimia.

In one embodiment, the time history of the transesophageal impedance measurement is recorded in the memory of the implanted module (e.g., in an operating log), for later telemetry to the external module, for review and analysis by the physician. With this information, the physician can preferentially choose the operating parameters of the system to best suit the eating habits of an individual patient.

In an alternative embodiment, the output of the transesophageal impedance measurement becomes a control input into CPU 154 of circuit 112 in neuroregulator 104 (FIG. 3). The therapy signal output of the neuroregulator 104 can be timed automatically to correspond to the timing and quantity of food consumed via a suitable algorithm.

11. Activity Monitoring System

The weight reduction resulting from the application of therapy described in this patent application is expected to produce an increased feeling of well-being in the patient, and possibly an increase in the amount of activity in which the patient is comfortable becoming involved.

In certain embodiments, the therapy system 100 monitors the activity of the patient. Generally, the therapy system 100 records the change in activity over the course of treatment. The therapy is applied to accomplish a goal (e.g., obesity reduction), and the activity level as a consequence of achieving the goal (e.g., weight loss) is then measured.

In an embodiment, this change in activity then can be mapped to the effects of the treatment. This mapping of the change in activity to the results of treatment can be personally advantageous to patients as well as advantageous to the medical community. For example, knowledge of the likely change, both in weight and in activity level, could be useful information for patients who are contemplating the implant and associated therapy.

In addition, such mapping would advantageously provide documented evidence of the positive effect of the weight control system to reimbursement groups. Additionally, from a medical/scientific perspective, it is known that weight loss is generally related to caloric intake, activity level, and metabolic rate. Increased quantification in the area of activity level would aid in developing a robust relationship among these factors.

There are a variety of methods which can be used for measuring activity level. Some of these models have been used as the basis for determining the preferred rate of implantable pacemakers and defibrillators. For example, a sensor of movement or acceleration (e.g., a gyroscope-based sensor), can provide an instantaneous measurement of activity level. Suitable hardware, software, and/or algorithm systems can then derive from these measurements the activity level averaged over a period of time (e.g., a 24 hr period).

An accelerometer also can be used to track patient activity. Other examples of activity sensing options include tracking the respiratory rate of the patient, by monitoring bio-impedance measurements (e.g., intrathoracic impedance), measuring a minute volume of, e.g., a compendium of respiratory rate and tidal volume, and monitoring blood pH, blood oxygen level, and blood pressure. In each case, the instantaneous value of the measurement can be integrated over a suitable time period.

Referring now to the present disclosure generally, the various program modules and operational steps can be implemented as routines, programs, components, data structures, and other types of structures that may perform particular tasks or that may implement particular abstract data types. Embodiments of the present disclosure can be implemented as a computer process (method), a computing system, or as an article of manufacture, such as a computer program product or computer readable media. The computer program product may be a computer storage media readable by a computer system and encoding a computer program of instructions for executing a computer process. Accordingly, embodiments of the present disclosure may be embodied in hardware and/or in software (including firmware, resident software, micro-code, etc.), within various computing systems, such as the microprocessor, FPGA, or other memory or logical devices such as those illustrated in FIG. 25, or other processing units and/or programmable circuits discussed herein. In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain or store the program for use by or in connection with the instruction execution system, apparatus, or device, but generally excludes propagated signals.

With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto. Any publications referred to herein are hereby incorporated by reference.

The invention claimed is:

1. A method of recharging an implantable neuroregulator containing a rechargeable battery comprising measuring a baseline temperature of the implantable neuroregulator at a predetermined time prior to a charging session;

measuring a rate of rise in temperature or a rise in temperature of the implantable neuroregulator from the baseline temperature during a charging session;

selecting a variable or constant rate of charge of the battery based on the rise of temperature or the rate of rise of the temperature of the implantable neuroregulator, wherein the variable or constant rate of charge is selected to not cause an increase in the rate of rise in temperature beyond a predetermined unsafe rate or the temperature of the implantable neuroregulator beyond a predetermined maximum safe temperature over the baseline temperature, wherein the constant or variable rate of charge is based on current or voltage during a selected charge interval;

determining the charge level of the battery, rate of rise in temperature, baseline temperature of the implantable neuroregulator, type of battery, and a constant or variable rate of charging by the implantable neuroregulator; and communicating from the implantable neuroregulator to an external charger that the implantable neuroregulator can accept battery charge energy, the level of energy, and the duration of the energy when the baseline temperature and the charge level of the battery are within predefined limits; and stopping charging when the rate of rise of temperature of the implantable device exceeds the predetermined unsafe rate, wherein the predetermined unsafe rate is 2°

C. per hour or greater or when the temperature of the implantable neuroregulator exceeds a predetermined maximum safe temperature over the baseline temperature.

2. A method of claim 1 further comprising:
receiving the communication at the external charger; generating the charging energy at the level requested and for the time requested by the implantable neuroregulator, and sending the charging energy to implantable neuroregulator only if requested to do so.

3. A method of claim 2, further comprising:
terminating charging when the implantable neuroregulator communicates that it will not accept charging energy or when the external charger is moved out of range.

4. A method of claim 3, wherein the implantable neuroregulator communicates that it will not accept charge when the battery indicates it is charged or when the temperature exceeds a predetermined maximum safe limit, or when the rate of temperature rise exceeds a predetermined limit.

5. The method of claim 1, wherein the variable rate of charge is selected.

\* \* \* \* \*